United States Patent
Yu et al.

(10) Patent No.: US 10,738,062 B2
(45) Date of Patent: Aug. 11, 2020

(54) CHROMANE-SUBSTITUTED TETRACYCLIC COMPOUNDS AND USES THEREOF FOR THE TREATMENT OF VIRAL DISEASES

(71) Applicant: Merck Sharp & Dohme Corp., Rahway, NJ (US)

(72) Inventors: Wensheng Yu, Edison, NJ (US); Joseph A. Kozlowski, Princeton, NJ (US); Ling Tong, Warren, NJ (US); Craig A. Coburn, Seattle, WA (US); Bin Hu, Shanghai (CN); Bin Zhong, Shanghai (CN); Jinglai Hao, Shanghai (CN); Dahai Wang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/326,043

(22) PCT Filed: Aug. 14, 2017

(86) PCT No.: PCT/US2017/046679
§ 371 (c)(1),
(2) Date: Feb. 15, 2019

(87) PCT Pub. No.: WO2018/035006
PCT Pub. Date: Feb. 22, 2018

(65) Prior Publication Data
US 2019/0185486 A1 Jun. 20, 2019

(30) Foreign Application Priority Data

Aug. 18, 2016 (WO) ............... PCT/CN2016/095881

(51) Int. Cl.
| | | |
|---|---|---|
| C07D 498/04 | (2006.01) | |
| A61K 45/06 | (2006.01) | |
| A61K 31/496 | (2006.01) | |
| A61K 31/5365 | (2006.01) | |
| A61P 31/14 | (2006.01) | |

(52) U.S. Cl.
CPC .......... *C07D 498/04* (2013.01); *A61K 31/496* (2013.01); *A61K 31/5365* (2013.01); *A61K 45/06* (2013.01); *A61P 31/14* (2018.01)

(58) Field of Classification Search
CPC .. A61K 31/496; A61K 31/5365; A61K 45/06; A61P 31/14; C07D 498/04
See application file for complete search history.

(56) References Cited

U.S. PATENT DOCUMENTS

| | | |
|---|---|---|
| 9,242,988 B2 | 1/2016 | Girijavallabhan et al. |
| 2012/0083483 A1 | 4/2012 | Coburn et al. |
| 2015/0335648 A1 | 11/2015 | Yu et al. |
| 2016/0045526 A1 | 2/2016 | Girijavallabhan et al. |

FOREIGN PATENT DOCUMENTS

| | | |
|---|---|---|
| WO | WO2009102568 A1 | 8/2009 |
| WO | 2010065674 A1 | 6/2010 |
| WO | WO2012/041014 A1 | 4/2012 |
| WO | 2014/110706 A1 | 7/2014 |

OTHER PUBLICATIONS

International Search Report and Written Opinion for PCT/CN2016/095881, dated May 24, 2017, 19 pages.
International Search Report and Written Opinion for PCT/US2017/046679, dated Oct. 24, 2017, 16 pages.
Tong, Ling et al, Structure—activity relationships of proline modifications around the tetracyclic-indole class of NS5A inhibitors, Bioorganic & Medicinal Chemistry Letters, 2016, 5354-5360, 26.
Yu, Wensheng et al, Discovery of Chromane Containing Hepatitis C Virus (HCV) NS5A Inhibitors with Improved Patency against Resistance-Associated Variants, Journal of Medicinal Chemistry, 2016, 10228-10243, 59.

*Primary Examiner* — Erich A Leeser
(74) *Attorney, Agent, or Firm* — Jeffrey P. Bergman; Catherine D. Fitch

(57) ABSTRACT

The present invention relates to novel Chromane-Substituted Tetracyclic Compounds of Formula (I) and pharmaceutically acceptable salts thereof, wherein A, A', $R^2$ $R^3$, $R^4$ and $R^5$ are as defined herein. The present invention also relates to compositions comprising a Chromane-Substituted Tetracyclic Compound, and methods of using the Chromane-Substituted Tetracyclic Compounds for treating or preventing HCV infection in a patient.

(I)

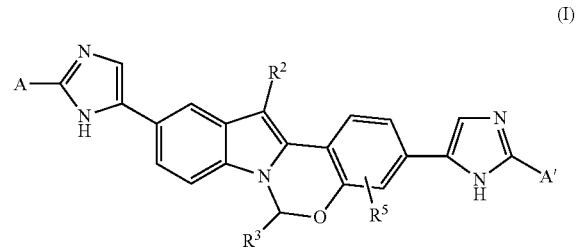

14 Claims, No Drawings
Specification includes a Sequence Listing.

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: PCR PRIMER

<400> SEQUENCE: 1
ccggctacct gcccattc                                                       18

<210> SEQ ID NO 2
<211> LENGTH: 22
<212> TYPE: DNA
<213> ORGANISM: Artificial Sequence
<220> FEATURE:
<223> OTHER INFORMATION: PCR PRIMERS

<400> SEQUENCE: 2
ccagatcatc ctgatcgaca ag                                                  22

<210> SEQ ID NO 3
<211> LENGTH: 24
<212> TYPE: DNA
```

```
<213> ORGANISM: Artificial Sequence
<220> FEATURE:
<223> OTHER INFORMATION: PCR PRIMERS

<400> SEQUENCE: 3
acatcgcatc gagcgagcac gtac                                              24

<210> SEQ ID NO 4
<211> LENGTH: 24
<212> TYPE: DNA
<213> ORGANISM: Artificial Sequence
<220> FEATURE:
<223> OTHER INFORMATION: PCR PRIMERS

<400> SEQUENCE: 4
cgcgtctcct ttgagctgtt tgca                                              24

<210> SEQ ID NO 5
<211> LENGTH: 15
<212> TYPE: DNA
<213> ORGANISM: Artificial Sequence
<220> FEATURE:
<223> OTHER INFORMATION: PCR PRIMERS

<400> SEQUENCE: 5
acggcgagcc cttgg                                                        15

<210> SEQ ID NO 6
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 6
tttctgctgt ctttgggacc t                                                 21

<210> SEQ ID NO 7
<211> LENGTH: 17
<212> TYPE: DNA
<213> ORGANISM: Artificial Sequence
<220> FEATURE:
<223> OTHER INFORMATION: PCT PRIMERS

<400> SEQUENCE: 7
atggacaggc gccctga                                                      17

<210> SEQ ID NO 8
<211> LENGTH: 20
<212> TYPE: DNA
<213> ORGANISM: Artificial Sequence
<220> FEATURE:
<223> OTHER INFORMATION: PCT PRIMERS

<400> SEQUENCE: 8
ttgatgggca gcttggtttc                                                   20

<210> SEQ ID NO 9
<211> LENGTH: 17
<212> TYPE: DNA
<213> ORGANISM: Artificial Sequence
<220> FEATURE:
<223> OTHER INFORMATION: PCR PRIMERS

<400> SEQUENCE: 9
cacgccatgc gctgcgg                                                      17
```

```
<210> SEQ ID NO 10
<211> LENGTH: 19
<212> TYPE: DNA
<213> ORGANISM: Artificial Sequence
<220> FEATURE:
<223> OTHER INFORMATION: PCR PRIMERS

<400> SEQUENCE: 10
tgcggaaccg gtgagtaca                                              19

<210> SEQ ID NO 11
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 11
gcgggtttat ccaagaaagg a                                           21

<210> SEQ ID NO 12
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 12
cggaattgcc aggacgaccg g                                           21
```

CHROMANE-SUBSTITUTED TETRACYCLIC COMPOUNDS AND USES THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US17/046679, filed Aug. 14, 2017, which claims priority to International Patent Application No. PCT/CN2016/095881, filed Aug. 18, 2016. Each of the aforementioned applications is incorporated by reference in its entirety.

FIELD OF THE INVENTION

The present invention relates to novel Chromane-Substituted Tetracyclic Compounds, compositions comprising a Chromane-Substituted Tetracyclic Compound, and methods of using the Chromane-Substituted Tetracyclic Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal.

Recent attention has been focused toward the identification of inhibitors of HCV NS5A. HCV NS5A is a 447 amino acid phosphoprotein which lacks a defined enzymatic function. It runs as 56 kD and 58 kD bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula

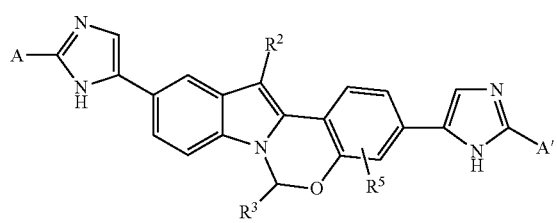

(I)

or a pharmaceutically acceptable salt thereof, wherein:
A is:

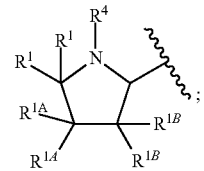

A' is:

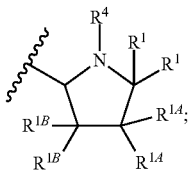

each occurrence of $R^1$ is independently selected from H, $C_1$-$C_6$ alkyl, $C_3$-$C_7$ cycloalkyl, $C_1$-$C_6$ haloalkyl, —O—$C_3$-$C_6$ alkyl, —N($R^9$)$_2$, —O—($C_1$-$C_6$ haloalkyl), and halo;

each occurrence of $R^{1A}$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;

each occurrence of $R^{1B}$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl) and halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —$CH_2$— or —$CH_2CH_2$—;

$R^2$ is selected from H, $C_1$-$C_6$ alkyl, $C_3$-$C_7$ cycloalkyl, phenyl and halo;

$R^3$ is selected from:

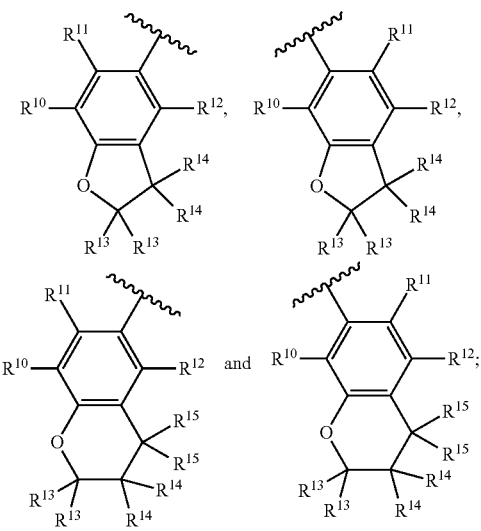

each occurrence of $R^4$ is independently selected from —C(O)—C($R^7$)$_2$NHC(O)O—$R^8$ and —C(O)—C($R^7$)$_2$—N($R^6$)$_2$ $R^5$ represents up to 3 optional substituents, each independently selected from halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, $C_6$-$C_{10}$ aryl, benzyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

each occurrence of $R^6$ is independently selected from H, $C_1$-$C_6$ alkyl and $C_3$-$C_7$ cycloalkyl, wherein two $R^6$ groups, together with the nitrogen atom to which they are attached, can combine to form a 4 to 8-membered monocyclic heterocycloalkyl;

each occurrence of $R^7$ is independently selected from H, $C_1$-$C_6$ alkyl, $C_1$-$C_6$ haloalkyl, phenyl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^9$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^7$ groups, that are attached to a common carbon atom, together with the common carbon atom to which they are attached, can combine to form a spirocyclic $C_3$-$C_7$ cycloalkyl group;

each occurrence of $R^8$ is independently selected from $C_1$-$C_6$ alkyl, $C_3$-$C_7$ cycloalkyl and $C_6$-$C_{10}$ aryl;

each occurrence of $R^9$ is independently selected from H, $C_1$-$C_6$ alkyl, $C_3$-$C_7$ cycloalkyl and $C_6$-$C_{10}$ aryl;

$R^{10}$ is selected from H, $C_1$-$C_6$ alkyl, $C_3$-$C_7$ cycloalkyl and halo;

$R^{11}$ is selected from H, $C_1$-$C_6$ alkyl, $C_3$-$C_7$ cycloalkyl and halo;

$R^{12}$ is selected from H, $C_1$-$C_6$ alkyl, $C_3$-$C_7$ cycloalkyl and halo;

each occurrence of $R^{13}$ is independently selected from H, $C_1$-$C_6$ alkyl and $C_3$-$C_7$ cycloalkyl, or both $R^{13}$ groups and the common carbon atom to which they are each attached, can combine to form a spirocyclic $C_3$-$C_7$ cycloalkyl group;

each occurrence of $R^{14}$ is independently selected from H, $C_1$-$C_6$ alkyl, $C_3$-$C_7$ cycloalkyl and halo; or both $R^{14}$ groups and the common carbon atom to which they are each attached, join to form a spirocyclic $C_3$-$C_7$ cycloalkyl group; or an $R^{14}$ group and $R^{13}$ group, together with the carbon atoms to which they are each attached, join to form a fused $C_3$-$C_7$ cycloalkyl group; or an $R^{14}$ group and $R^{15}$ group, together with the carbon atoms to which they are each attached, can combine to form a fused $C_3$-$C_7$ cycloalkyl group; and each occurrence of $R^{15}$ is independently selected from H, $C_1$-$C_6$ alkyl, $C_3$-$C_7$ cycloalkyl and halo, or both $R^{15}$ groups and the common carbon atom to which they are each attached, can combine to form a spirocyclic $C_3$-$C_7$ cycloalkyl group.

The Compounds of Formula (I) (also referred to herein as the "Chromane-Substituted Tetracyclic Compounds") and pharmaceutically acceptable salts thereof can be useful, for example, for inhibiting HCV viral replication or replicon activity, and for treating or preventing HCV infection in a patient. Without being bound by any specific theory, it is believed that the Chromane-Substituted Tetracyclic Compounds inhibit HCV viral replication by inhibiting HCV NS5A.

Accordingly, the present invention provides methods for treating or preventing HCV infection in a patient, comprising administering to the patient an effective amount of at least one Chromane-Substituted Tetracyclic Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Chromane-Substituted Tetracyclic Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. Unless otherwise indicated, a cycloalkyl group is unsubstituted. An illustrative example of such a cycloalkyl group (also referred to herein as a "cycloalkanoyl" group) includes, but is not limited to, cyclobutanoyl:

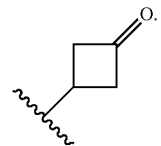 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkenyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and unless specified ohterwise, either available bond on a heteroarylene ring can connect to either group flanking the heteroarylene group. For example, the group "A-heteroarylene-B," wherein the heteroarylene group is:

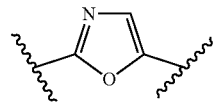 [SMILES: *c1cnc(*)o1]

is understood to represent both:

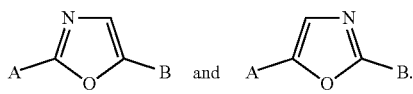

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. Unless otherwise indicated, a heterocycloalkyl group is unsubstituted. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

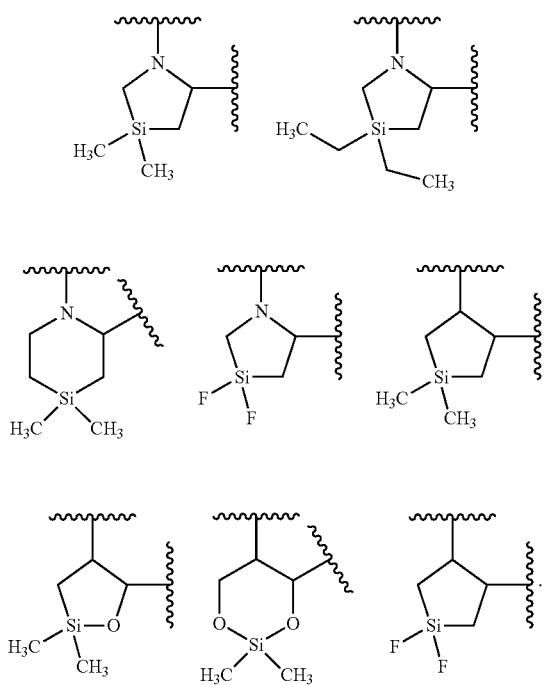

A ring carbon atom of a heterocycloalkyl group may be functionalized as a carbonyl group. An illustrative example of such a heterocycloalkyl group is:

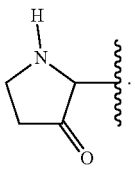 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. A ring carbon atom of a heterocycloalkenyl group may be functionalized as a carbonyl group. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. Unless otherwise indicated, a heterocycloalkenyl group is unsubstituted.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^1$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Chromane-Substituted Tetracyclic Compound or a pharmaceutically acceptable salt or solvate of the compound. The transformation may occur by various mechanisms (e.g., by metabolic or chemical processes), such as, for example, through hydrolysis in blood.

For example, if a Chromane-Substituted Tetracyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$ alkylcarbamoyl-$(C_1-C_2)$alkyl and piperidino-, pyrrolidino- or morpholino$(C_2-C_3)$alkyl, and the like.

Similarly, if a Chromane-Substituted Tetracyclic Compound contains an alcohol functional group, a prodrug can be formed by the replacement of the hydrogen atom of the alcohol group with a group such as, for example, $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino $(C_1-C_4)$alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a Chromane-Substituted Tetracyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1-C_{10}$)alkyl, ($C_3-C_7$) cycloalkyl, benzyl, a natural α-aminoacyl, —C(OH)C(O)O$Y^1$ wherein $Y^1$ is H, ($C_1-C_6$) alkyl or benzyl, —C(O$Y^2$)$Y^3$ wherein $Y^2$ is ($C_1-C_4$) alkyl and $Y^3$ is ($C_1-C_6$)alkyl; carboxy ($C_1-C_6$)alkyl; amino($C_1-C_4$)alkyl or mono-N- or di-N,N—($C_1-C_6$)alkylaminoalkyl; —C($Y^4$)$Y^5$ wherein $Y^4$ is H or methyl and $Y^5$ is mono-N- or di-N,N—($C_1-C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Chromane-Substituted Tetracyclic Compounds can form salts which are also within the scope of this invention. The term "salt(s)", as employed herein, denotes acidic salts formed with inorganic and/or organic acids, as well as basic salts formed with inorganic and/or organic bases. In addition, when a Chromane-Substituted Tetracyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Chromane-Substituted Tetracyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Chromane-Substituted Tetracyclic Compounds may be atropisomers (e.g., substituted biaryls) and are considered as part of this invention. Enantiomers can also be directly separated using chiral chromatographic techniques.

It is also possible that the Chromane-Substituted Tetracyclic Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Chromane-Substituted Tetracyclic Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

When a substituent on a chiral carbon atom is depicted as a racemate (by using a straight line bond to a chiral center), it is to be understood that both the alpha and beta configurations of said substituent group are to be considered part of the present invention. For example, the compound of the present invention, which is drawn as follows:

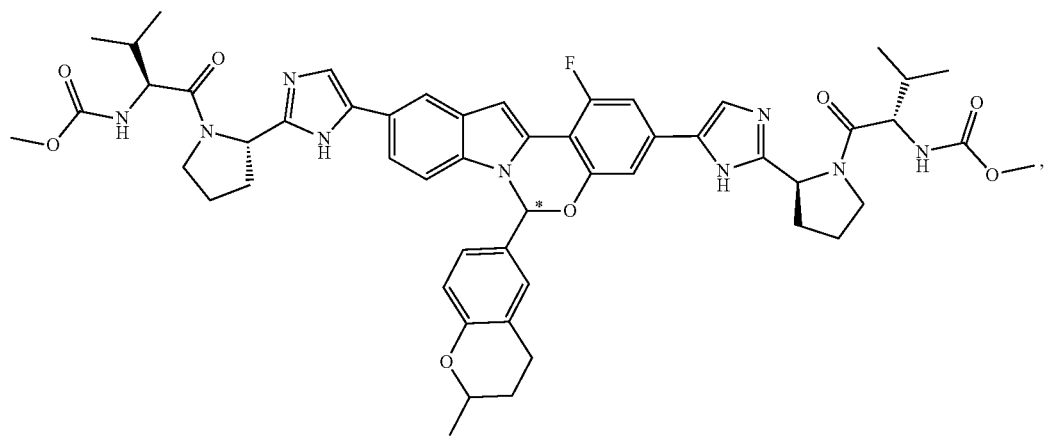

is understood to encompass both diastereomers at the indicated chiral center, the structures of which are as follows:

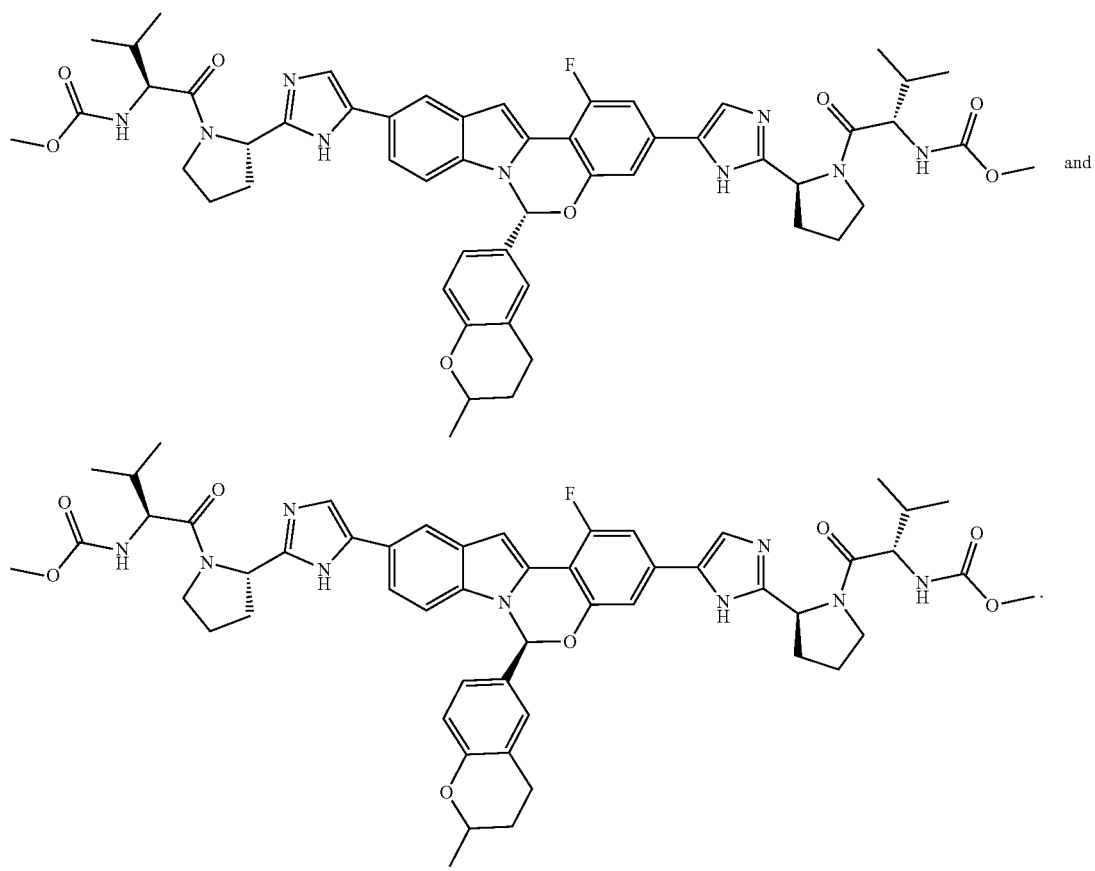

In the Examples section below, compounds of the present invention that have been purified into pure diastereomers are sometimes depicted in racemic form but identified as "Isomer 1" and "Isomer 2." In this instance, the absolute stereochemistry of each isolated diastereomer has not been determined and the Isomer 1 and Isomer 2 designations are used to represent each individual purified diastereomer.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Chromane-Substituted Tetracyclic Compounds, and of the salts, solvates, hydrates, esters and prodrugs of the Chromane-Substituted Tetracyclic Compounds, are intended to be included in the present invention.

The following abbreviations are used below and have the following meanings: Ac is acyl; Aq is aqueous; $BF_3.OEt$ is boron trifluoride etherate; BOC or Boc is tert-butyloxycarbonyl; $Boc_2O$ is Boc anhydride; n-BuPACl$_2$ is admantyl n-butylphosphine dichloride; t-Bu is tertiary butyl; t-BuOK is potassium tert-butoxide; n-BuLi is n-butyllithium; Celite is the tradename for diatomaceous earth; conc. is concentrated; $Cp_2TiCl_2$ is di(cyclopentadienyl)titanium(IV) dichloride; DAST is diethylaminosulfur trifluoride; DCM is dichloromethane; DDQ is 2,3-dichloro-5,6-dicyano-1,4-benzoquinone; Deoxofluor is bis(2-methoxyethyl)aminosulfur trifluoride; DIAD is diisopropylazodicarboxylate; DIBAL is diisobutylaluminum hydride; DIPEA is diisopropylethylamine; DMA is dimethylacetamide; DME is dimethoxyethane; DMF is N,N-dimethylformamide; dppf is diphenylphosphinoferrocene; DMSO is dimethylsulfoxide; ESI is electrospray ionization; EtOAc is ethyl acetate; EtOH is ethanol; HATU is O-(7-azabenzotriazol-1-yl)-N,N,N',N'-tetramethyluronium hexafluorophosphate; HPLC is high performance liquid chromatography; KOAc is potassium acetate; LCMS is liquid chromatography/mass spectrometry; LiHMDS is lithium hexamethyldisilazide; MeCN is acetonitrile; Me is methyl; MeLi is methyllithium; MeOH is methanol; MS is mass spectrometry; Na$_2$EDTA is disodium ethylenediaminetetraacetate; NMP is N-methylpyrrolidinone; PCR is polymerase chain reaction; Pd$_2$(dba)$_3$ is tris(dibenzylideneacetone)dipalladium(O); Pd(dppf)$_2$Cl$_2$ is [1,1'-Bis(diphenylphosphino)ferrocene]dichloro palladium (II); Ph is phenyl; PIFA is phenyliodine bis(trifluoroacetate); RT-PCR is reverse transcription polymerase chain reaction; SFC is supercritical flow chromatography; TFA is trifluoroacetic acid; THF is tetrahydrofuran; TLC is thin-layer chromatography; TsOH is p-toluenesulfonic acid; XPhos is 2-dicyclohexylphosphino-2',4',6'-triisopropylbiphenyl; and ZnEt$_2$ is diethyl zinc.

The Compounds of Formula (I)

The present invention provides Chromane-Substituted Tetracyclic Compounds of Formula (I):

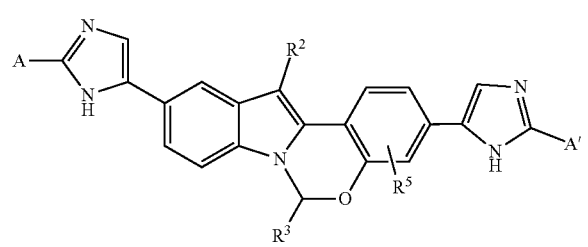

(I)

and pharmaceutically acceptable salts thereof, wherein A, A', $R^2$, $R^3$ and $R^5$ are defined above for the Compounds of Formula (I).

In one embodiment, for the compounds of formula (I), A and A' are each a 5-membered heterocycloalkyl group.

In another embodiment, for the compounds of formula (I), A and A' are each independently selected from:

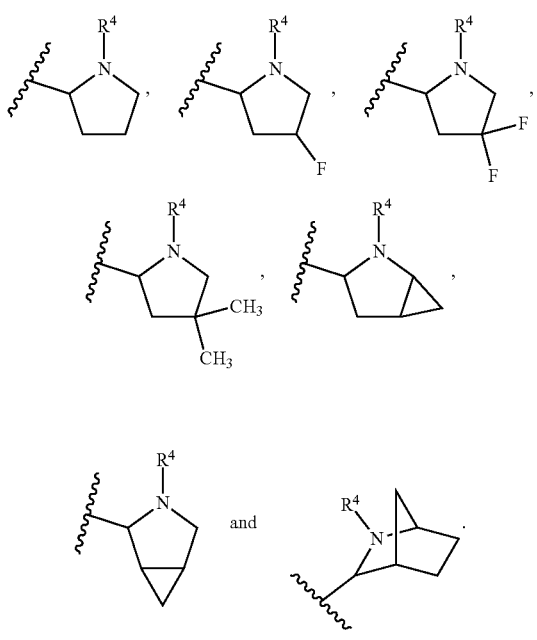

In another embodiment, for the compounds of formula (I), A and A' are each independently selected from:

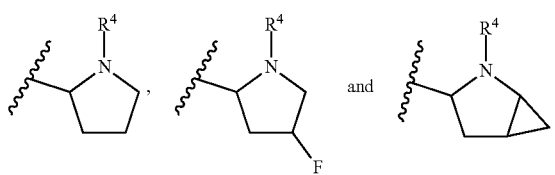

In one embodiment, for the compounds of formula (I), A and A' are each independently selected from:

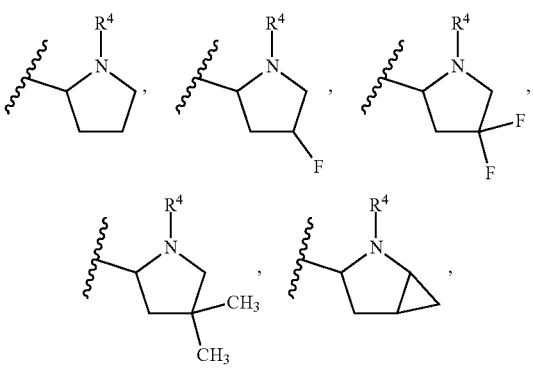

-continued

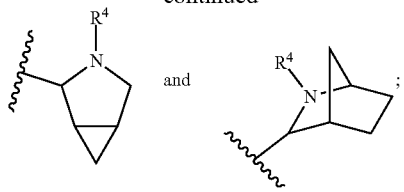

and each occurrence of R⁴ is independently —C(O)CH(R⁷)NHC(O)OCH₃, wherein R⁷ is selected from: isopropyl, —CF(CH₃)₂,

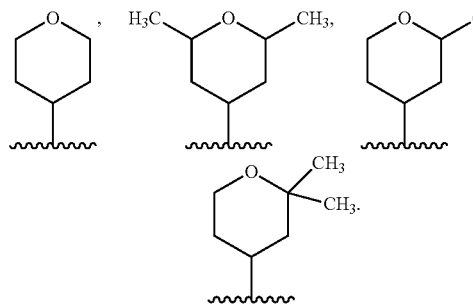

In another embodiment, for the compounds of formula (I), A and A' are each independently selected from:

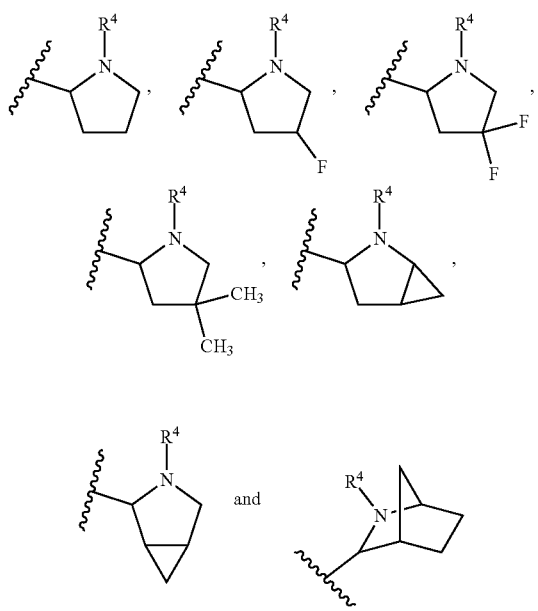

and each occurrence of R⁴ is:

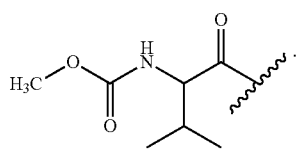 [SMILES: *C(=O)C(NC(=O)OC)C(C)C]

In another embodiment, for the compounds of formula (I), A and A' are each independently selected from:

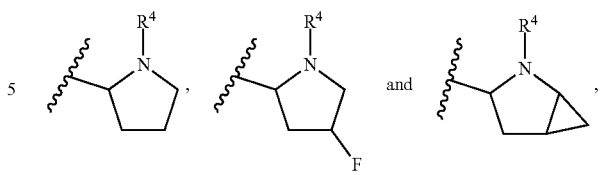

each occurrence of R⁴ is independently —C(O)CH(R⁷)NHC(O)OCH₃, wherein R⁷ is selected from: isopropyl, —CF(CH₃)₂, —CH(CH₃)OCH₂CH₃,

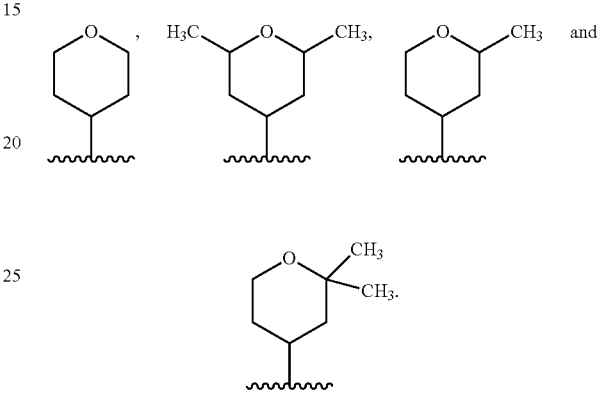

In one embodiment, for the compounds of formula (I), each occurrence of R⁴ is independently —C(O)CH(R⁷)NHC(O)OCH₃.

In another embodiment, for the compounds of formula (I), each occurrence of R⁴ is independently —C(O)CH(R⁷)NHC(O)OCH₃, and each occurrence of R⁷ is independently selected from C₁-C₆ alkyl, C₁-C₆ haloalkyl and 4 to 6-membered monocyclic heterocycloalkyl, wherein said 4 to 6-membered monocyclic heterocycloalkyl group can be optionally substituted with up to five C₁-C₆ alkyl groups or said 4 to 6-membered monocyclic heterocycloalkyl group can be optionally substituted on a ring carbon atom with a spirocyclic C₃-C₆ cycloalkyl group.

In one embodiment, for the compounds of formula (I), each occurrence of R⁴ is independently —C(O)CH(R⁷)NHC(O)OCH₃, wherein R⁷ is selected from: isopropyl, —CF(CH₃)₂, —CH(CH₃)OCH₂CH₃,

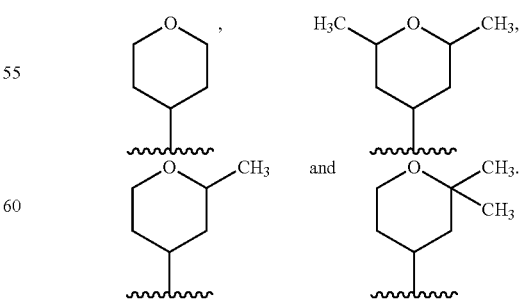

In one embodiment, the compound of formula (I) has the formula (Ia):

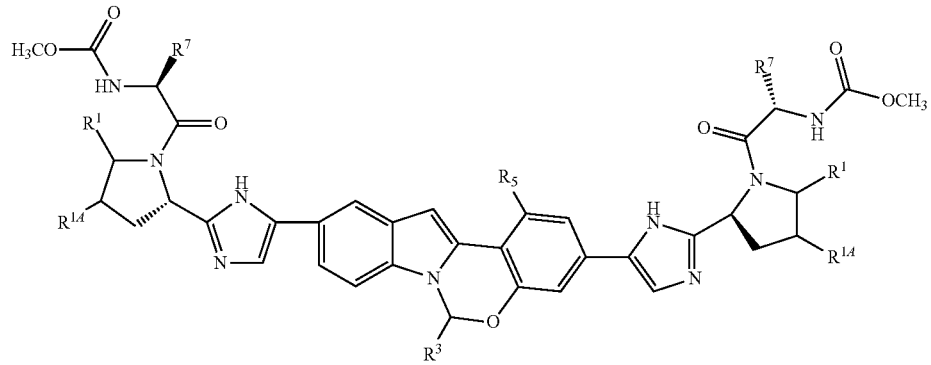

(Ia)

or a pharmaceutically acceptable salt thereof,
wherein:
each $R^1$ is H;
each $R^{14}$ is independently H or F, or an $R^{14}$ group and an $R^1$ group that are attached to same ring, together with the ring carbon atoms to which they are attached, can combine to form a fused cyclopropyl group;
$R^3$ is selected from:

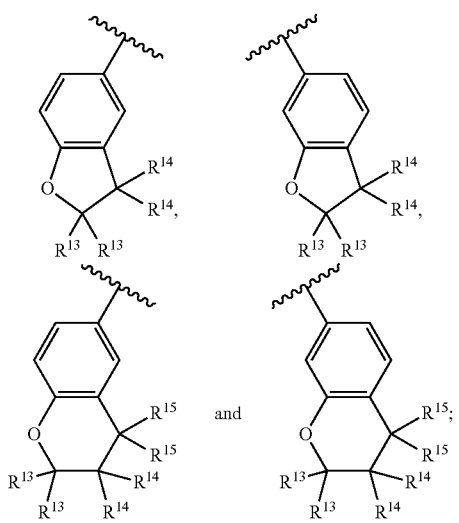

$R^5$ is H, F or methyl;
each occurrence of $R^7$ is independently selected from $C_1$-$C_6$ alkyl, $C_1$-$C_6$ haloalkyl, phenyl and 4 to 6-membered monocyclic heterocycloalkyl, wherein said 4 to 6-membered monocyclic heterocycloalkyl group can be optionally substituted with up to 2 groups, each independently selected from $C_1$-$C_6$ alkyl;
each occurrence of e is independently selected from H and $C_1$-$C_6$ alkyl, or both $R^{13}$ groups and the common carbon atom to which they are each attached, join to form a spirocyclic $C_3$-$C_7$ cycloalkyl group;
each occurrence of $R^{14}$ is independently selected from H, halo and $C_1$-$C_6$ alkyl; or both $R^{14}$ groups and the common carbon atom to which they are each attached, join to form a spirocyclic $C_3$-$C_7$ cycloalkyl group; or an $R^{14}$ group and $R^{13}$ group, together with the carbon atoms to which they are each attached, join to form a fused $C_3$-$C_7$ cycloalkyl group; or an $R^{14}$ group and $R^{15}$ group, together with the carbon atoms to which they are each attached, join to form a fused $C_3$-$C_7$ cycloalkyl group; and
each occurrence of $R^{15}$ is independently selected from H, $C_1$-$C_6$ alkyl and halo, or both $R^{15}$ groups and the common carbon atom to which they are each attached, join to form a spirocyclic $C_3$-$C_7$ cycloalkyl group.

In one embodiment, for compounds of formula (Ia), each occurrence of $R^1$ is H.

In one embodiment, for compounds of formula (Ia), each occurrence of $R^{14}$ is independently H or F.

In another embodiment, for compounds of formula (Ia), one or both $R^1$ groups combine with the adjacent $R^{14}$ group to form a fused cyclopropyl group.

In one embodiment, for compounds of formula (Ia), each occurrence of $R^7$ is independently selected from: isopropyl, —CF(CH$_3$)$_2$, —CH(CH$_3$)OCH$_2$CH$_3$,

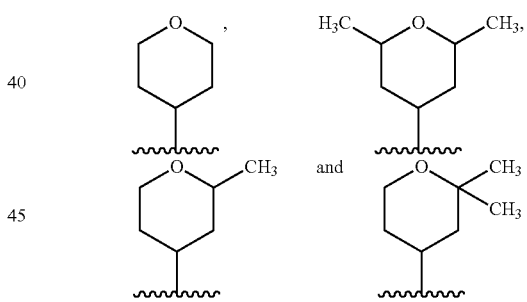

In another embodiment, for the compounds of formula (Ia), each occurrence of $R^7$ is independently selected from: isopropyl, —CF(CH$_3$)$_2$, —CH(CH$_3$)OCH$_2$CH$_3$,

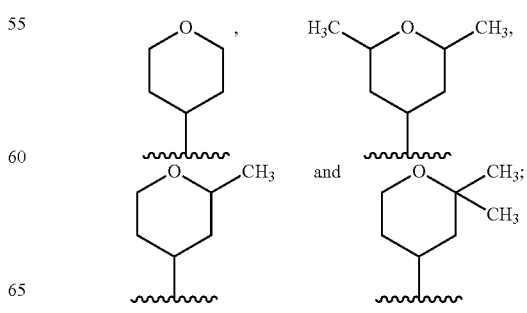

and

R³ is selected from:

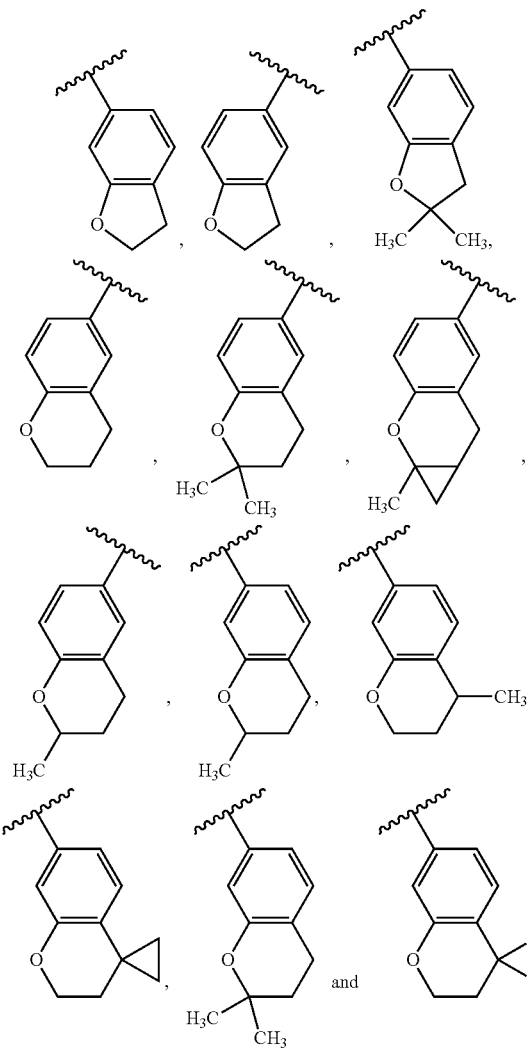

In another embodiment, for the compounds of formula (Ia), R⁵ is H, F or methyl; each occurrence of R⁷ is independently selected from: isopropyl, —CF(CH₃)₂, —CH(CH₃)OCH₂CH₃,

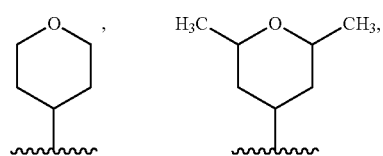

and

R³ is selected from:

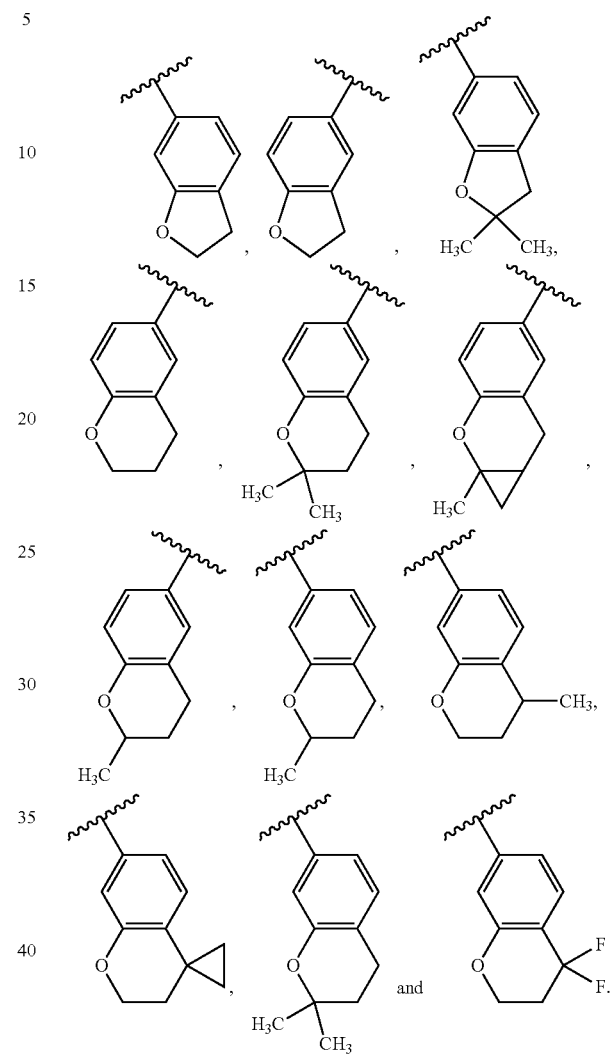

In one embodiment, for the compounds of formula (I) or (Ia), R² is H

In another embodiment, for the compounds of formula (I) or (Ia), R² is halo.

In another embodiment, for the compounds of formula (I) or (Ia), R² is $C_1$-$C_6$ alkyl.

In one embodiment, for the compounds of formula (I) or (Ia), R³ is selected from:

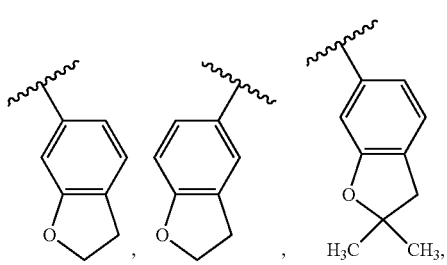

-continued

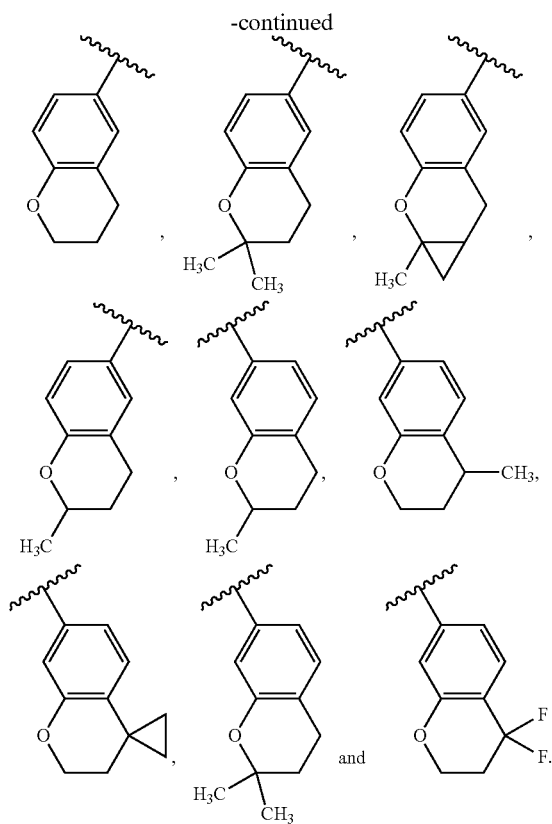

In one embodiment, for the compounds of formula (I) or (Ia), $R^5$ is absent.

In another embodiment, for the compounds of formula (I) or (Ia), $R^5$ is F.

In another embodiment, for the compounds of formula (I) or (Ia), $R^5$ is $C_1$-$C_6$ alkyl.

In still another embodiment, for the compounds of formula (I) or (Ia), $R^5$ is methyl.

In one embodiment, variables A, A', $R^2$, $R^3$ and $R^5$ for the Compounds of Formula (I) are selected independently of each other.

In another embodiment, the Compounds of Formula (I) are in substantially purified form.

In one embodiment, variables $R^1$, $R^{1-4}$, $R^5$ and $R^7$ for the Compounds of Formula (Ia) are selected independently of each other.

In another embodiment, the Compounds of Formula (Ia) are in substantially purified form.

Other embodiments of the present invention include the following:

(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HCV antiviral agents, immunomodulators, and anti-infective agents.

(n) The pharmaceutical composition of (m), wherein the HCV antiviral agent is an antiviral selected from the group consisting of HCV protease inhibitors and HCV NS5B polymerase inhibitors.

(o) A pharmaceutical combination that is (i) a pharmaceutically acceptable salt of a Compound of Formula (I) and (ii) a second therapeutic agent selected from the group consisting of HCV antiviral agents, immunomodulators, and anti-infective agents; wherein the pharmaceutically acceptable salt of the Compound of Formula (I) and the second therapeutic agent are each employed in an amount that renders the combination effective for inhibiting HCV replication, or for treating HCV infection and/or reducing the likelihood or severity of symptoms of HCV infection.

(p) The combination of (o), wherein the HCV antiviral agent is an antiviral selected from the group consisting of HCV protease inhibitors and HCV NS5B polymerase inhibitors.

(q) A method of inhibiting HCV replication in a subject in need thereof which comprises administering to the subject an effective amount of a pharmaceutically acceptable salt of a Compound of Formula (I).

(r) A method of treating HCV infection and/or reducing the likelihood or severity of symptoms of HCV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HCV antiviral agents, immunomodulators, and anti-infective agents.

(t) The method of (s), wherein the HCV antiviral agent is an antiviral selected from the group consisting of HCV protease inhibitors and HCV NS5B polymerase inhibitors.

(u) A method of inhibiting HCV replication in a subject in need thereof which comprises administering to the subject the pharmaceutical composition of (l), (m) or (n) or the combination of (o) or (p).

(v) A method of treating HCV infection and/or reducing the likelihood or severity of symptoms of HCV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HCV antiviral agents, immunomodulators, and anti-infective agents.

(y) The pharmaceutical composition of (x), wherein the HCV antiviral agent is an antiviral selected from the group consisting of HCV protease inhibitors and HCV NS5B polymerase inhibitors.

(z) A pharmaceutical combination that is (i) a Compound of Formula (I) and (ii) or a pharmaceutically acceptable salt thereof, a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(aa) The combination of (z), wherein the HCV antiviral agent is an antiviral selected from the group consisting of HCV protease inhibitors and HCV NS5B polymerase inhibitors.

(bb) A method of inhibiting HCV replication in a subject in need thereof which comprises administering to the subject an effective amount of a Compound of Formula (I) or a pharmaceutically acceptable salt thereof.

(cc) A method of treating HCV infection and/or reducing the likelihood or severity of symptoms of HCV infection in a subject in need thereof which comprises administering to the subject an effective amount of a Compound of Formula (I) or a pharmaceutically acceptable salt thereof.

(dd) The method of (cc), wherein the Compound of Formula (I) or pharmaceutically acceptable salt thereof, is administered in combination with an effective amount of at least one second therapeutic agent selected from the group consisting of HCV antiviral agents, immunomodulators, and anti-infective agents.

(ee) The method of (dd), wherein the HCV antiviral agent is an antiviral selected from the group consisting of HCV protease inhibitors and HCV NS5B polymerase inhibitors.

(ff) A method of inhibiting HCV replication in a subject in need thereof which comprises administering to the subject the pharmaceutical composition of (w) (x) or (y) or the combination of (z) or (aa).

(gg) A method of treating HCV infection and/or reducing the likelihood or severity of symptoms of HCV infection in a subject in need thereof which comprises administering to the subject the pharmaceutical composition of (w) (x) or (y) or the combination of (z) or (aa).

The present invention also includes a compound of the present invention for use (i) in, (ii) as a medicament for, or (iii) in the preparation of a medicament for: (a) medicine; (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-94, as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis.

Scheme 1 shows methods useful for making the compounds of formula G3, which are useful intermediates for making the Compounds of Formula (I).

Scheme 1

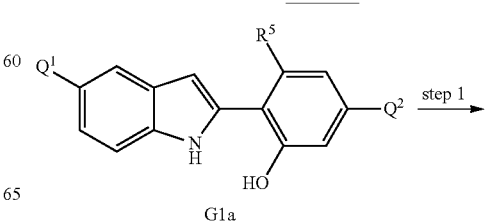

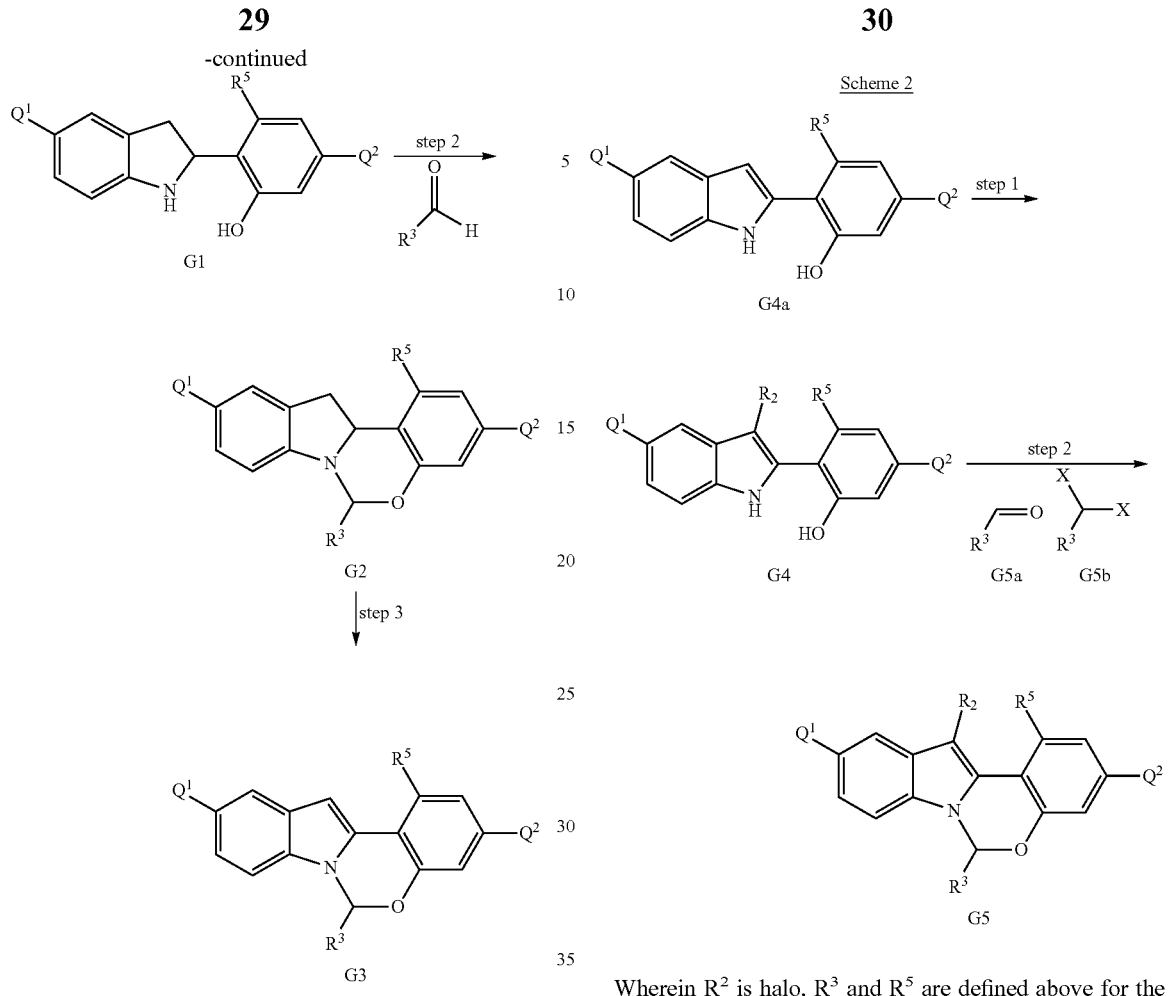

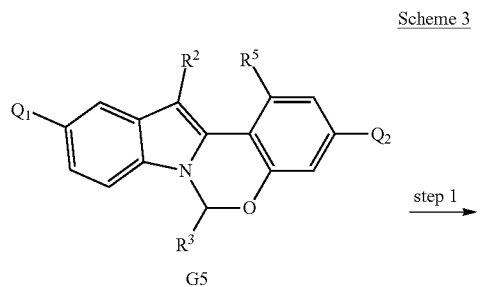

Wherein $R^3$ and $R^5$ are defined above for the Compounds of Formula (I) and $Q^1$ and $Q^2$ are each independently halo, hydroxyl, or a protected hydroxyl group, such as a methoxy or benzyloxy group.

An indole compound of formula G1a (which can be prepared as described in International Publication No. WO 2012/040923) can be treated with tin in concentrated HCl/EtOH solution to provide compounds of formula G1. A compound of formula G1 can be reacted with an aldehyde of formula $R^3$CHO in the presence of an acid to provide tetracyclic compounds of formula G2. Compounds of formula G2 can then be oxidized to provide the tetracyclic compounds of formula G3.

Scheme 2 shows methods useful for making the compounds of formula G5, which are useful intermediates for making the Compounds of Formula (I).

Wherein $R^2$ is halo, $R^3$ and $R^5$ are defined above for the Compounds of Formula (I), X is halo, and $Q^1$ and $Q^2$ are each independently halo, hydroxyl, or a protected hydroxyl group, such as a methoxy or benzyloxy group.

A compound of formula G4a (which can be prepared as described in International Publication No. WO 2012/040923) can be halogenated to provide the compounds of formula G4, wherein $R^2$ is halo. A compound of formula G4 can then be converted to the compounds of formula G5 via reaction with an aldehyde of formula G5a in the presence of an acid, or alternatively, by reaction with a dihalo compound of formula G5b in the presence of a base. The $R^2$ group of the compounds of formula G5 can be further elaborated using methods well-known in the art of organic synthesis to make the entire scope of variable $R^2$.

Scheme 3 shows methods useful for making the compounds of formula G12, which are useful intermediates for making the Compounds of Formula (I).

-continued
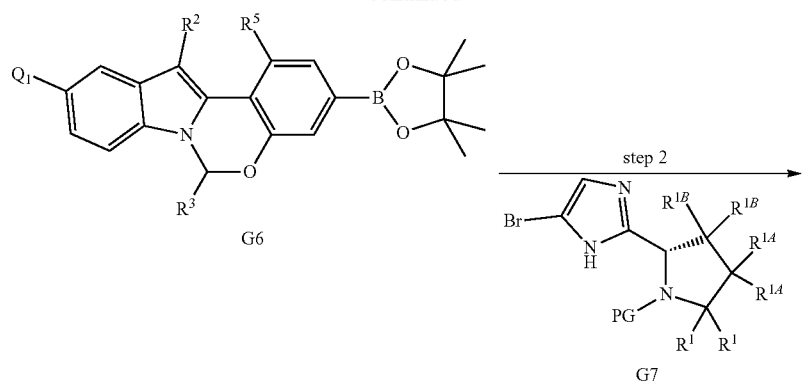
G6
step 2
G7
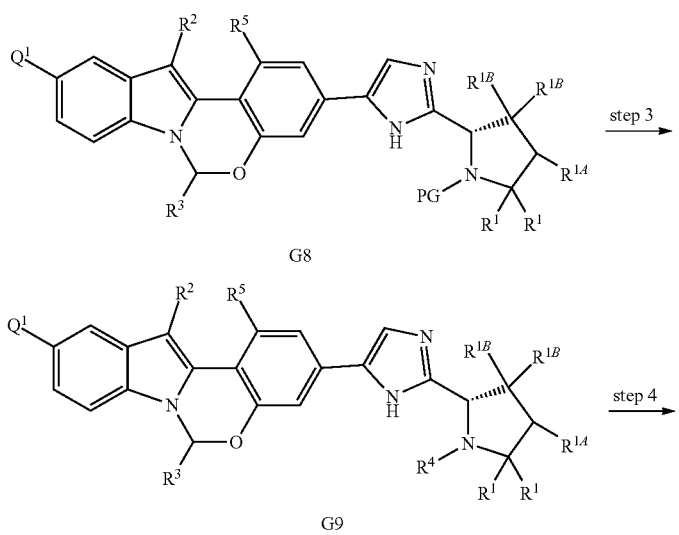
G8
step 3
G9
step 4
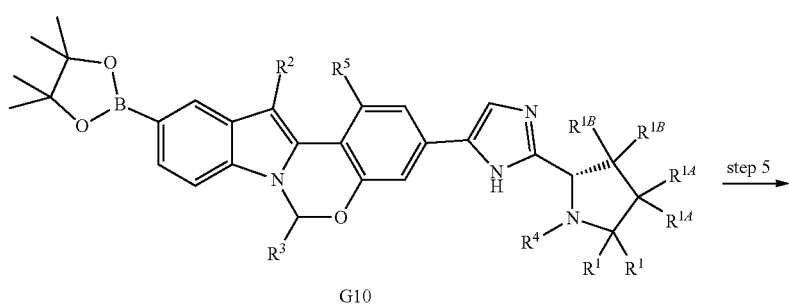
G10
step 5
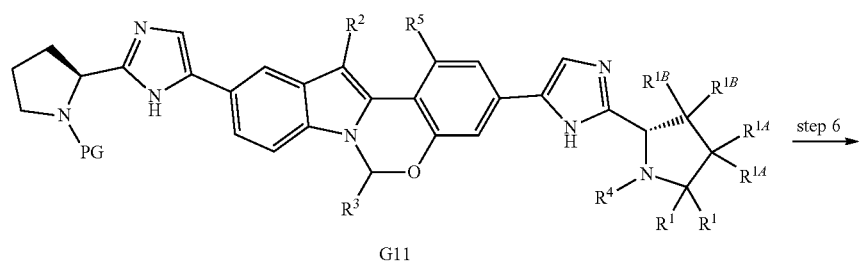
G11
step 6

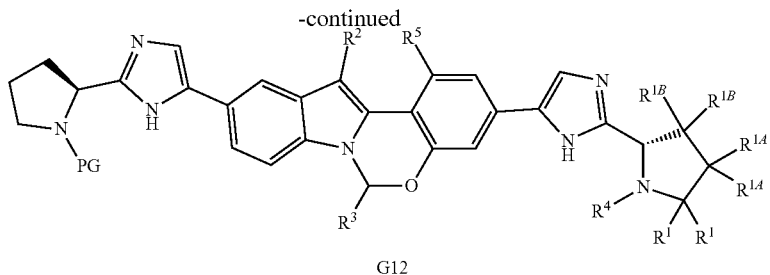

G12

Wherein $R^2$, $R^3$, $R^4$ and $R^5$ are defined above for the Compounds of Formula (I), PG is a secondary amino protecting group, and $Q^1$ and $Q^2$ are each independently halo, hydroxyl, or a protected hydroxyl group, such as a methoxy or benzyloxy group.

A compound of formula G5 can be reacted with bis(pinacolato)diboron to provide the compounds of formula G6. A compound of formula G6 can then undergo a Pd-mediated coupling with a bromo compound of formula G7 (prepared as described in International Publication No. WO 2012/040923) to provide the compounds of formula G8. Compounds of formula G8 can then be deprotected and subjected to an amide coupling with a desired cap compound to provide a compound of formula G9. A compound of formula G9 is then subjected to a Pd-mediated coupling with bis(pinacolato)diboron to provide the boronic ester compounds of formula G10. A compound of formula G10 can then undergo a Pd-mediated coupling with a bromo compound of formula G7 (prepared as described in International Publication No. WO 2012/040923) to provide the compounds of formula G11. Compounds of formula G11 can then be deprotected and subjected to an amide coupling with a desired cap compound to provide a compound of formula G12. Diastereoisomers of the synthetic intermediates and final products can be separated using SFC or HPLC with chiral columns.

Scheme 4 shows methods useful for making the compounds of formula G18, which correspond to the Compounds of Formula (I).

Scheme 4

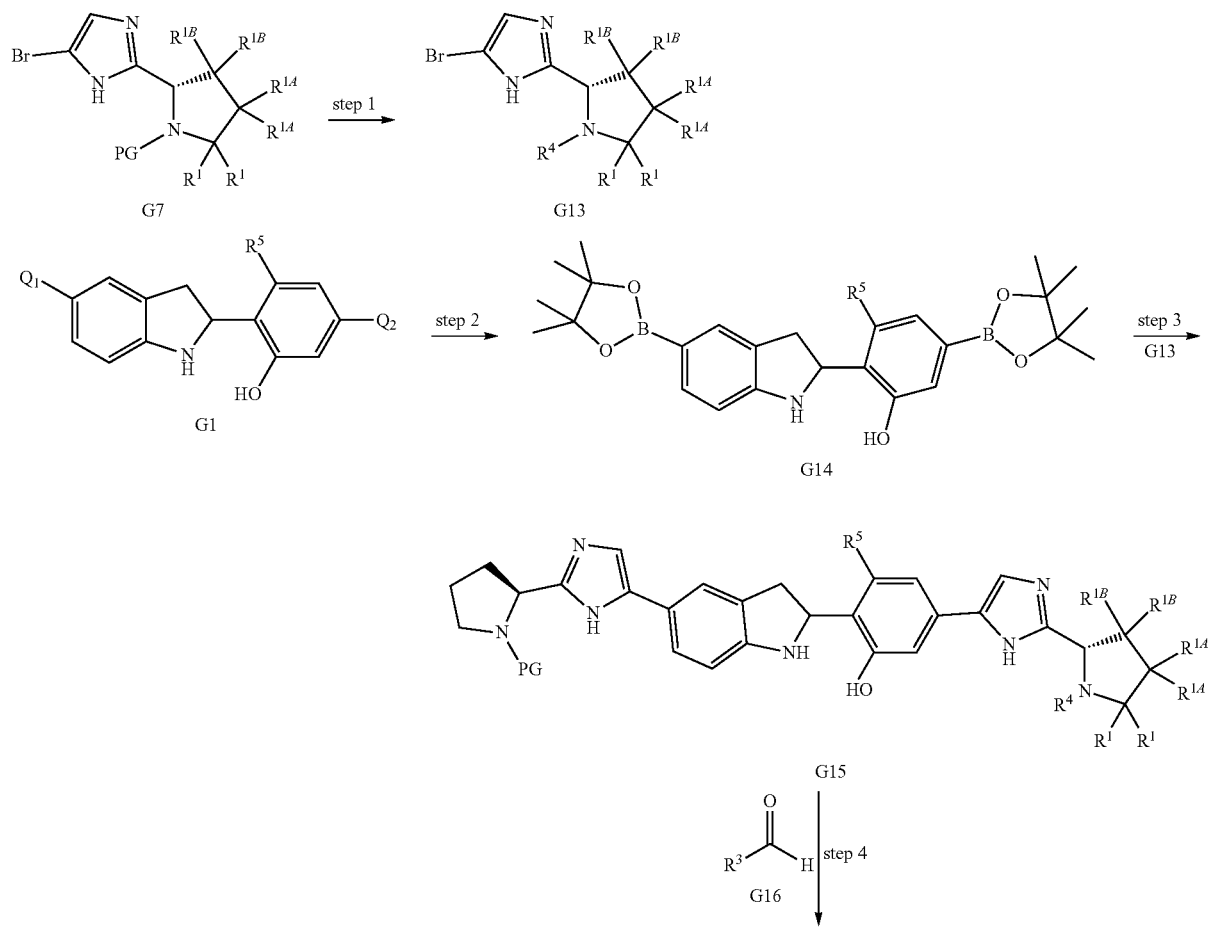

-continued

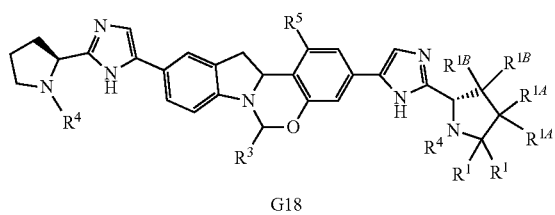

G18

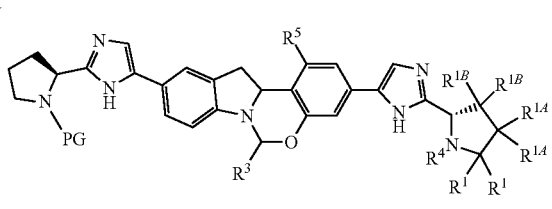

G17

Wherein $R^3$, $R^4$ and $R^5$ are defined above for the Compounds of Formula (I), PG is a secondary amino protecting group, and $Q^1$ and $Q^2$ are each independently halo, hydroxyl, or a protected hydroxyl group, such as a methoxy or benzyloxy group.

A compound of formula G7 can be deprotected and subjected to an amide coupling with a desired cap compound to provide an intermediate bromoimidazole compound of formula G13. A compound of formula G1 can be converted to compound of formula G14 via a Pd-mediated coupling reaction with bis(pinacolato)diboron. The compound of formula G14 can then be subjected to a Pd-mediated coupling with a compound of formula G13 to provide a compound of formula G15. The compound of formula G15 can then be converted a compound of formula G17 via reaction with an aldehyde of formula G16 in the presence of an acid. The compound of formula G17 can then be subjected to an oxidative cyclization to provide the tetracyclic compounds of formula G18. The distereoisomers of G18 can be separated using, for example, SFC and employing chiral columns.

One skilled in the art of organic synthesis will recognize that the synthesis of fused tetracyclic cores contained in Compounds of Formula (I) may require protection of certain functional groups (i.e., derivatization for the purpose of chemical compatibility with a particular reaction condition). Suitable protecting groups for the various functional groups of these Compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the fused tetracyclic cores of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

The preparation of multicyclic intermediates useful for making the fused tetracyclic ring systems of the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The starting materials used and the intermediates prepared using the methods set forth in Schemes 1-4 may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

The following intermediates, which are useful for making the compounds of the present invention, can be made using methods described in International Patent Publication Nos. WO2014110705 and WO2014110706.

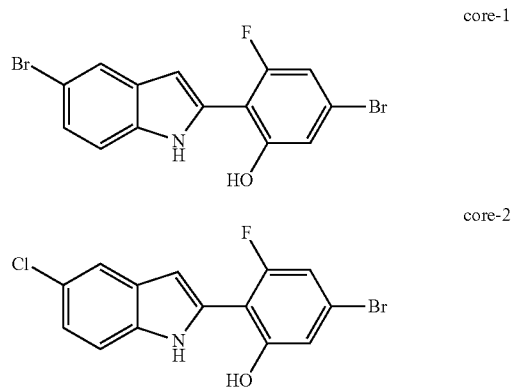

-continued
core-3
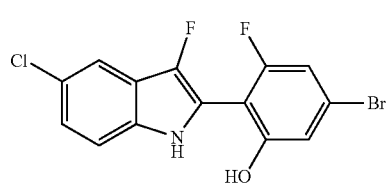
core-4
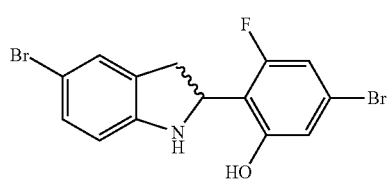
core-5
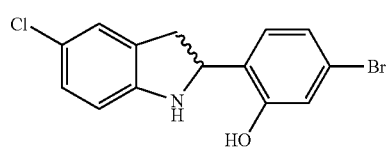
core-6
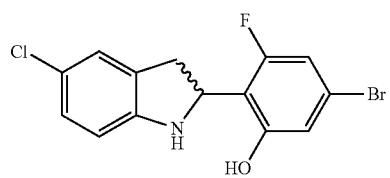
core-7
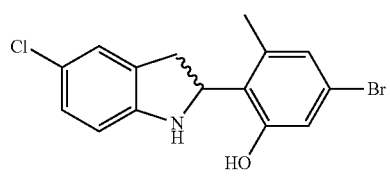
cap-1
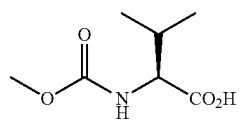
cap-2
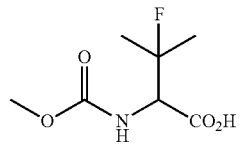
cap-3
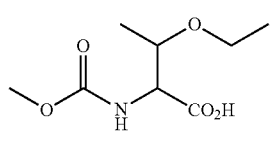
cap-4
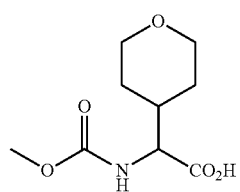
-continued
cap-5
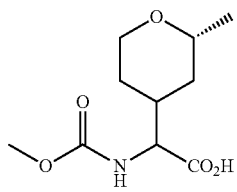
cap-6
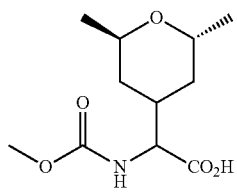
cap-7
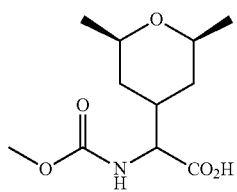
cap-8
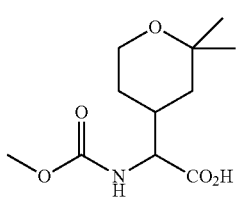
cap-9
cap-10
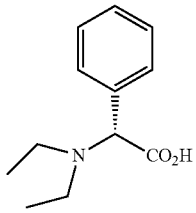
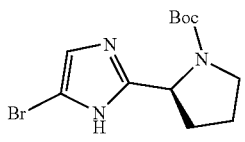
Br-imidazole-1
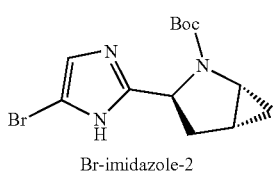
Br-imidazole-2

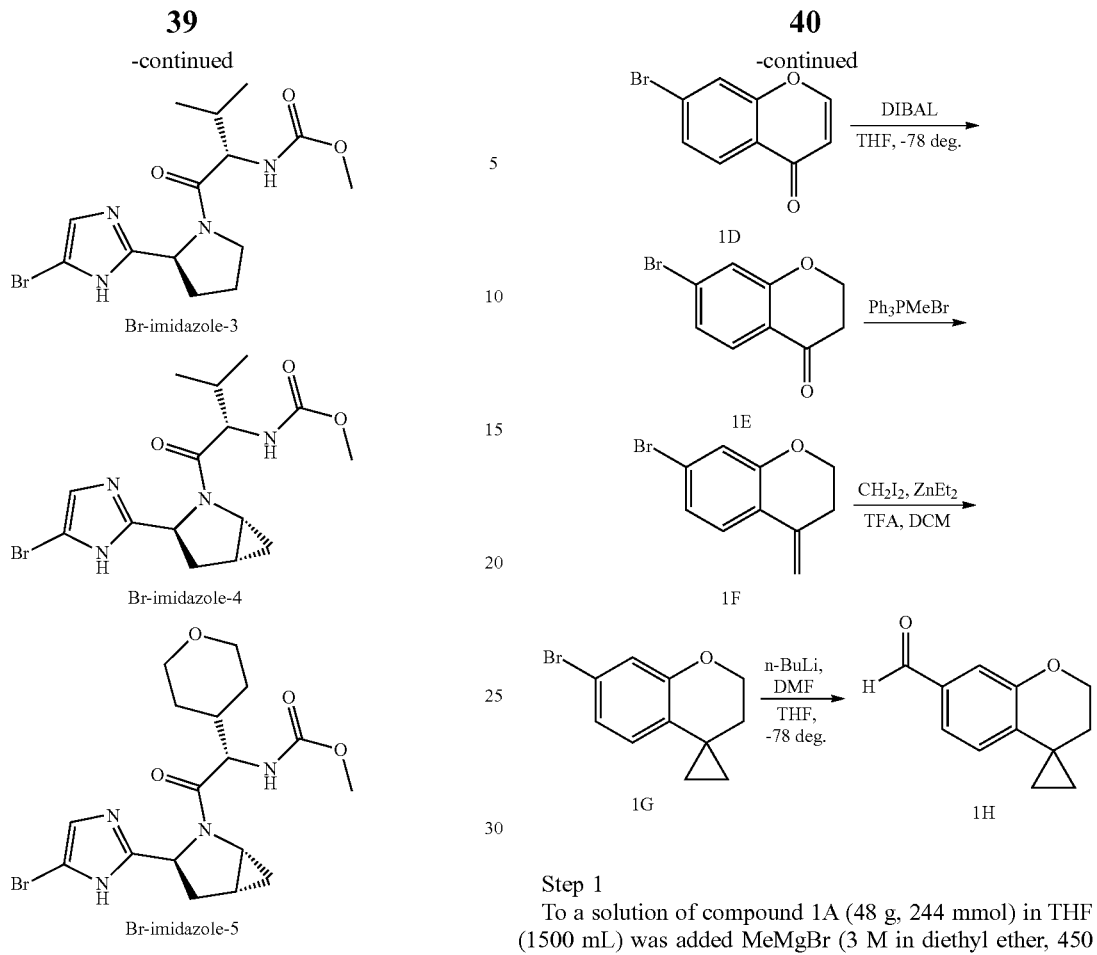

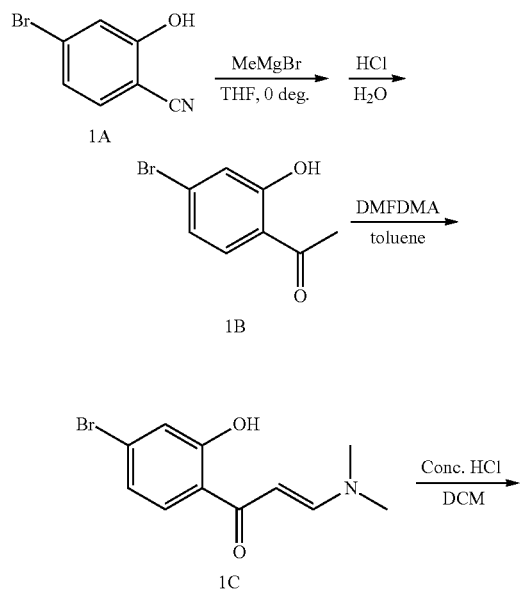

Example 1

Preparation of Intermediate Compound 1H

Step 1

To a solution of compound 1A (48 g, 244 mmol) in THF (1500 mL) was added MeMgBr (3 M in diethyl ether, 450 mL, 1350 mmol) dropwise under nitrogen at −40° C. for 30 minutes. The mixture was allowed to stir at −40° C. for 1 hour, then at room temperature for 16 hours. Water (1000 mL) and conc. HCl (200 mL) were added and stirred at room temperature for 24 hours, then extracted with ethyl acetate. The organic extract was washed with saturated NaHCO$_3$, brine, dried over sodium sulfate, filtered and concentrated in vacuo to provide compound 1B as a solid. $^1$H-NMR (CDCl$_3$, 400 MHz): δ 12.32 (s, 1H), 7.55 (d, J=8.4 Hz, 1H), 7.15 (s, 1H), 7.01 (d, J=8.4 Hz, 1H), 2.59 (s, 3H).

Step 2

To a solution of compound 1B (48 g, 224 mmol) in dry toluene (500 mL) was added N,N-dimethylformamide (53.3 g, 448 mmol) at room temperature. The mixture was heated to reflux and allowed to stir at this temperature for 16 hours, then cooled, and filtered. The collected solid was washed with toluene to provide compound 1C as a solid. The filtrate was concentrated in vacuo, and the residue obtained was purified using flash column chromatography on silica gel (petroleum ether:ethyl acetate=5:1) to provide additional amount of compound 1C as a solid. $^1$H-NMR (CDCl$_3$, 400 MHz): δ 7.85 (d, J=12.0 Hz, 1H), 7.50 (d, J=8.8 Hz, 1H), 7.26 (s, 1H), 7.09 (s, 1H), 6.92 (d, J=8.8 Hz, 1H), 5.66 (d, J=12.0 Hz, 1H), 3.18 (s, 3H), 2.95 (s, 3H).

Step 3

To a solution of compound 1C (37 g, 137.5 mmol) in dichloromethane (400 mL) was added conc. HCl (115 mL, 1.375 mole) at room temperature. The mixture was stirred at reflux for 2 hours, and extracted with dichloromethane. The organic extract was washed with saturated NaHCO$_3$, brine, dried over sodium sulfate, filtered and concentrated in vacuo to provide compound 1D as a solid, which was used without further purification. $^1$H-NMR (CDCl$_3$, 400 MHz): δ 8.04 (d, J=8.8 Hz, 1H), 7.80 (d, J=6.4 Hz, 1H), 7.63 (s, 1H), 7.50 (d, J=8.8 Hz, 1H), 6.32 (d, J=6.4 Hz, 1H).

Step 4

To a solution of compound 1D (32.6 g, 145.5 mmol) in THF (600 mL) was added DIBAL (1 M in toluene, 437 mL, 437 mmol) dropwise under nitrogen at −78° C. for 30 minutes. The mixture was allowed to stir at −78° C. for 1 hour, then the reaction mixture was poured into 500 mL of 1 M aq. HCl, and extracted with ethyl acetate. The organic extract was washed with brine, dried over sodium sulfate, filtered and concentrated in vacuo. The residue obtained was purified using flash column chromatography on silica gel (petroleum ether:ethyl acetate=20:1 to provide compound 1E as a solid. $^1$H-NMR (CDCl$_3$, 400 MHz): δ 7.72 (d, J=8.0 Hz, 1H), 7.13-7.17 (m, 2H), 4.52 (t, J=6.4 Hz, 1H), 2.79 (d, J=6.4 Hz, 1H).

Step 5

To a solution of methyltriphenylphosphonium bromide (40.45 g, 111.31 mmol) in THF (500 mL) was added n-BuLi (2.5 M in hexane, 45.3 mL, 111.31 mmol) dropwise at 0° C. under nitrogen. The resulting reaction was allowed to stir at 0° C. for 1 hours and then a solution of compound 1E (21.34 g, 94.62 mmol) in THF (100 mL) was added. The mixture was allowed to stir at 0° C. for 1 hour, then at room temperature for another 1 hour. The reaction was quenched by addition of aq. NH$_4$Cl, and extracted with ethyl acetate. The organic extract was washed with brine, dried over sodium sulfate, filtered and concentrated in vacuo, and the residue obtained was purified using flash column chromatography on silica gel (petroleum ether:ethyl acetate=50:1 to provide compound 1F as an oil. $^1$H-NMR (CDCl$_3$, 400 MHz): δ 7.38 (d, J=8.8 Hz, 1H), 6.97-6.99 (m, 2H), 5.47 (s, 1H), 4.89 (s, 1H), 4.20 (t, J=5.6 Hz, 2H), 2.64 (t, J=5.6 Hz, 2H).

Step 6

CH$_2$I$_2$ (17.17 g, 66 mmol) was added dropwise to a stirred solution of ZnEt$_2$ (1 M in hexane, 33 mL, 33 mmol) in dichloromethane (33 mL) at −78° C. under nitrogen, and the mixture was allowed to stir at 0° C. for 15 minutes resulting in the formation of a precipitate. TFA (3.77 mL, 33 mmol) was added to the mixture resulting in the rapid formation of a homogeneous solution which was allowed to stir at 0° C. for 15 minutes. A solution of compound 1F (3.7 g, 16.5 mmol) in dichloromethane (10 mL) was then added and the resulting reaction was allowed to stir at room temperature for 16 hours. Saturated Na$_2$EDTA (70 mL) was then added and the resulting reaction was vigorously stirred for 5 minutes, then diluted with dichloromethane (100 mL) and saturated NaHCO$_3$ (100 mL). The aqueous layer was extracted with dichloromethane, and the organic extract was washed with brine, dried over sodium sulfate, filtered and concentrated in vacuo. The residue obtained was purified using flash column chromatography on silica gel (petroleum ether:ethyl acetate=50:1) to provide compound 1G as a solid. $^1$H-NMR (CDCl$_3$, 400 MHz): δ 6.89-6.94 (m, 2H), 6.47 (d, J=8.4 Hz, 1H), 4.25 (t, J=5.2 Hz, 2H), 1.82 (t, J=5.2 Hz, 2H), 1.00 (t, J=5.2 Hz, 2H), 0.82 (t, J=5.2 Hz, 2H).

Step 7

To a solution of compound 1G (0.77 g, 3.24 mmol) in THF (13 mL) was added n-BuLi (2.5 M in hexane, 2 mL, 5 mmol) dropwise at −78° C. under nitrogen. The mixture was allowed to stir at −78° C. for 5 minutes. The reaction was diluted with DMF (1 ml, 13 mmol), then allowed to stir at −78° C. for and additional 1 hour. The reaction was quenched by addition aq. NH$_4$Cl, and extracted with ethyl acetate. The organic extract was washed with brine, dried over sodium sulfate, filtered and concentrated in vacuo, and the residue obtained was purified using pre-TLC (petroleum ether:ethyl acetate=20:1) to provide compound 1H as an oil. MS (ESI) m/z: 189.0 [M+H]$^+$.

Example 2

Preparation of Intermediate Compound 2D and 2E

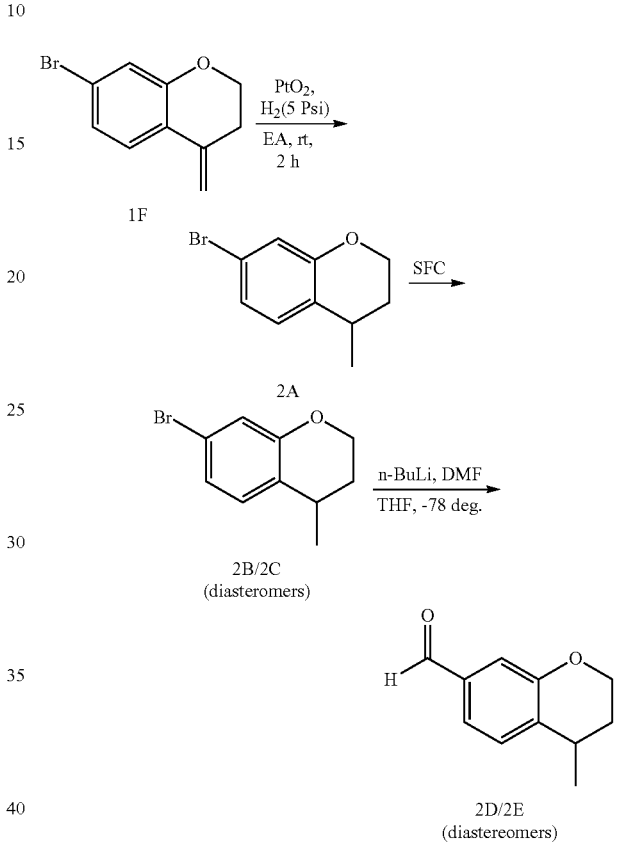

Step 1

A solution of compound 1F (3.2 g, 14.3 mmol) and PtO$_2$ (3.2 g) in ethyl acetate (50 mL) was allowed to stir under hydrogen balloon at room temperature for 2 hours, then the reaction mixture was filtered and concentrated in vacuo. The residue obtained was purified using flash column chromatography on silica gel (petroleum ether:ethyl acetate=100:1) to provide compound 2A as an oil. $^1$H-NMR (CDCl$_3$, 400 MHz): δ 6.93-6.99 (m, 3H), 4.10-4.20 (m, 2H), 2.83-2.91 (m, 1H), 2.00-2.08 (m, 1H), 1.67-1.72 (m, 1H), 1.65-1.66 (m, 3H).

Step 2

Compound 2A was separated using SFC to provide two diastereomers 2B and 2C. Column: Chiralpak AS-H 250×20 mm I.D., 5 um Mobile phase: 40% of IPA/NH$_4$OH in CO$_2$, Flow rate: 50 mL/min, Wavelength: 340 nm. The stereochemistry of 2B and 2C were assigned arbitrarily.

Step 3

To a solution of compound 2B (1 g, 4.42 mmol) in THF (10 mL) was added n-BuLi (2.5 M in hexane, 5.3 mL, 13.27 mmol) dropwise at −78° C. under nitrogen. The mixture was allowed to stir at −78° C. for 10 minutes, then DMF (2 ml, 26.55 mmol) was added and the resulting reaction was allowed to stir at −78° C. for 1 hour. The reaction was quenched by addition aq. NH$_4$Cl, and extracted with ethyl acetate. The organic extract was washed with brine, dried over sodium sulfate, filtered and concentrated in vacuo to provide compound 2D as an oil, which was used without further purification.

Compound 2E was prepared from compound 2C using the methodology described in Step 3 immediately above.

Example 3

Preparation of Intermediate Compound 3B

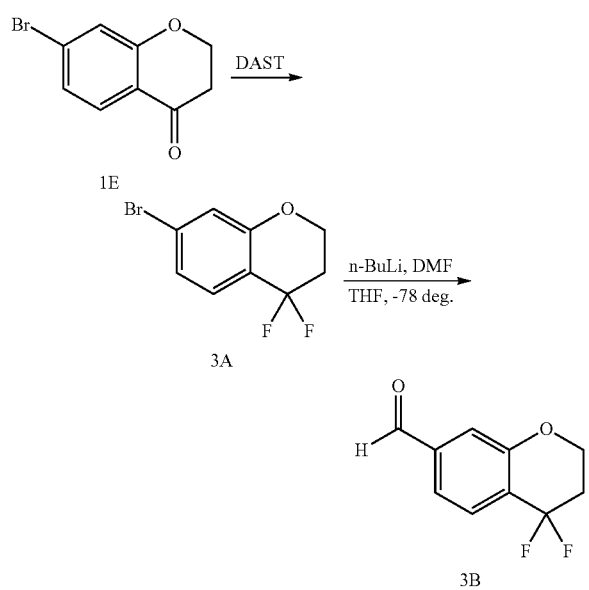

Step 1

Deoxofluor (10 mL, 50 mmol) was added to a solution of compound 1E (1.13 g, 5 mmol) in DCM (2 mL) and EtOH (0.1 mL) in a sealed tube. The reaction was heated to 40° C. and allowed to stir at this temperature for 24 hours. The reaction mixture was then poured into ice-water and basified to pH 9 using aqueous Na$_2$CO$_3$. The basified solution was extracted with DCM, and the organic extract was washed with brine, dried over sodium sulfate, filtered and concentrated in vacuo. The residue obtained was purified using flash column chromatography on silica gel eluted with petroleum ether to provide compound 3A as an oil. $^1$H-NMR (CDCl3, 400 MHz): δ 7.42 (d, J=8.4 Hz, 1H), 7.11 (d, J=8.8 Hz, 1H), 7.06 (s, 1H), 4.34 (t, J=5.6 Hz, 2H), 2.39-2.49 (m, 2H).

Step 2

To a solution of compound 3A (0.7 g, 2.8 mmol) in THF (10 mL) at −78° C. was added n-BuLi (2.5 M in hexane, 3.5 mL, 8.75 mmol) dropwise under nitrogen. The reaction was allowed to stir at −78° C. for 5 minutes, then DMF (1.4 mL, 18.2 mmol) was added. The resultant mixture was allowed to stir at −78° C. for 1 hour, then the reaction was quenched by addition aq. NH$_4$Cl, and extracted with ethyl acetate. The organic extract was washed with brine, dried over sodium sulfate, filtered and concentrated in vacuo, and the residue obtained was purified using flash column chromatography on silica gel (petroleum ether:ethyl acetate=20:1) to provide compound 3B as an oil. $^1$H-NMR (CDCl3 400 MHz): δ 9.96 (s, 1H), 7.74 (d, J=8.0 Hz, 1H), 7.50 (d, J=8.0 Hz, 1H), 7.37 (s, 1H), 4.40 (t, J=6.0 Hz, 2H), 2.45-2.54 (m, 2H).

Example 4

Preparation of Intermediate Compound 4C

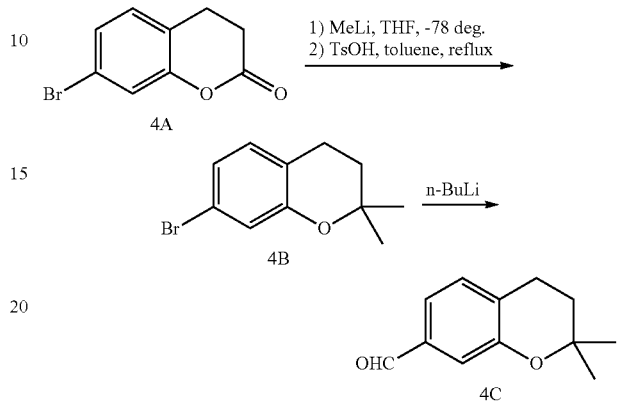

Step 1

To a solution of compound 4A (2.26 g, 10 mmol) in THF (30 mL) at 0° C. was added MeLi (1.6 M in ether, 15.6 mL, 25 mmol) dropwise under nitrogen. The mixture was allowed to stir at room temperature for 3 hours, then re-cooled to 0° C. using an ice bath, and aq. 1M HCl (2.5 mL) was added dropwise. The layers were separated, and the aqueous layer was extracted with ethyl acetate. The organic extract was washed with brine, dried over sodium sulfate, filtered and concentrated in vacuo. The residue obtained was dissolved in toluene (30 mL), TsOH—H$_2$O (95 mg, 0.5 mmol) was added, and the mixture was stirred at reflux for 16 hours in a Dean-Stark apparatus. The reaction mixture was then concentrated in vacuo, and the resulting residue obtained was purified using flash column chromatography on silica gel (petroleum ether:ethyl acetate=300:1 to provide compound 4B as an oil.

Step 2

To a solution of compound 4B (590 mg, 2.46 mmol) in THF (10 mL) at −78° C. was added n-BuLi (2.5 M in hexane, 3 mL, 7.5 mmol) dropwise under nitrogen. The mixture was allowed to stir at −78° C. for 10 minutes, then DMF (1.2 mL, 15.6 mmol) was added. The resultant mixture was allowed to stir at −78° C. for 1 hour, then the reaction was quenched by addition of 1N aq. HCl, then extracted with ethyl acetate. The organic extract was washed with brine, dried over sodium sulfate, filtered and concentrated in vacuo, and the residue obtained was purified using flash column chromatography on silica gel (petroleum ether:ethyl acetate=20:1) to provide compound 4C as an oil. MS (ESI) m/z: 191.0 [M+H]$^+$.

Example 5

Preparation of Intermediate Compound 5H

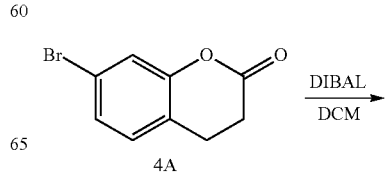

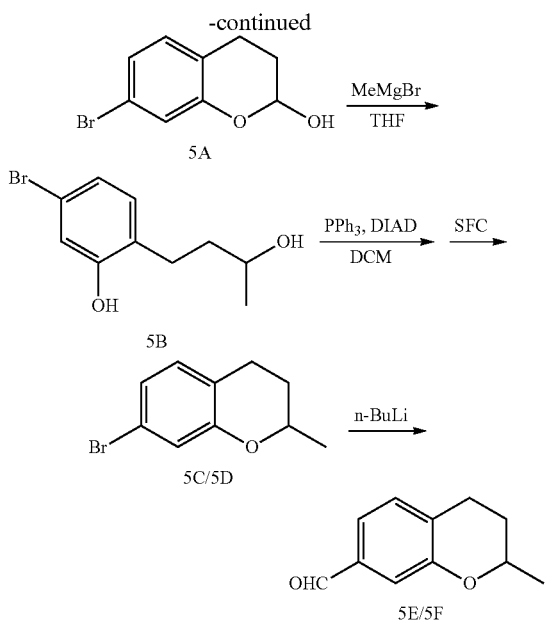

Step 1

To a solution of compound 4A (16 g, 70.8 mmol) in DCM (200 mL) at −78° C. was added DIBAL (1 M in toluene, 85 mL, 85 mmol) dropwise under nitrogen over a period of 15 minutes. The mixture was allowed to stir at −78° C. for 2 hours, then was poured into 200 mL of 1 M aq. HCl, and extracted with ethyl acetate. The organic extract was washed with brine, dried over sodium sulfate, filtered and concentrated in vacuo, and the residue obtained was purified using flash column chromatography on silica gel (petroleum ether: ethyl acetate=20:1 to provide compound 5A as a solid. $^1$H-NMR (CDCl$_3$, 400 MHz): δ6.81-6.98 (m, 3H), 5.54 (S, 1H), 2.79-2.99 (m, 1H), 2.49-2.64 (m, 1H), 1.85-2.01 (m, 2H).

Step 2

To a solution of compound 5A (11.5 g, 50.4 mmol) in THF (200 mL) at 0° C. was added MeMgBr (3 M in Et$_2$O, 50.4 mL, 151 mmol) dropwise under nitrogen. The mixture was allowed to stir at 0° C. for 20 minutes. The resultant mixture was allowed to warm to room temperature and stirred for 2 hours. The reaction was then quenched by addition 1N aq. HCl, extracted with ethyl acetate. The organic extract was washed with brine, dried over sodium sulfate, filtered and concentrated in vacuo, and the residue obtained was purified using flash column chromatography on silica gel (petroleum ether:ethyl acetate=10:1) to provide compound 5B as a solid. $^1$H-NMR (CDCl$_3$, 400 MHz): δ 6.89-7.06 (m, 3H), 3.69-3.79 (m, 1H), 2.77-2.87 (m, 1H), 2.59-2.62 (m, 1H), 1.61-1.83 (m, 2H), 1.16-1.25 (m, 3H).

Step 3

To a solution of compound 5B (8.2 g, 33.6 mmol) and PPh$_3$ (9.69 g, 37 mmol) in DCM (150 mL) at 0° C. was added DIAD (7.3 mL, 37 mmol) dropwise. The mixture was allowed to stir at 0° C. for 1 hour, then the reaction was quenched by addition of ice water, and extracted with DCM. The organic extract was washed with brine, dried over sodium sulfate, filtered and concentrated in vacuo, and the residue obtained was purified using flash column chromatography on silica gel (petroleum ether) to provide a mixture of isomeric compounds 5C and 5D as an oil, which was separated using SFC to provide isolated compounds 5C and 5D. Condition of SFC: Column: AD-3 (150×4.6 MM), Co-solvent: MeOH (0.05% DEA, 5-40%), flow rate: 25 mL/min.

Step 4

To a solution of compound 5C (1.108 g, 4.9 mmol) in THF (50 mL) at −78° C. was added n-BuLi (2.5 M in hexane, 6 mL, 15 mmol) dropwise under nitrogen. The mixture was allowed to stir at −78° C. for 10 minutes, then DMF (2.3 mL, 30 mmol) was added. The resultant mixture was allowed to stir at −78° C. for 1 hour, then the reaction was quenched by addition of aq. NH$_4$Cl, and extracted with ethyl acetate. The organic extract was washed with brine, dried over sodium sulfate, filtered and concentrated in vacuo, and the residue obtained was purified using flash column chromatography on silica gel (petroleum ether:ethyl acetate=20:1 to provide compound 5E as an oil.

Compound 5F was prepared from compound 5D using the methodology described in Step 4 immediately above.

Example 6

Preparation of Intermediate Compound 6E

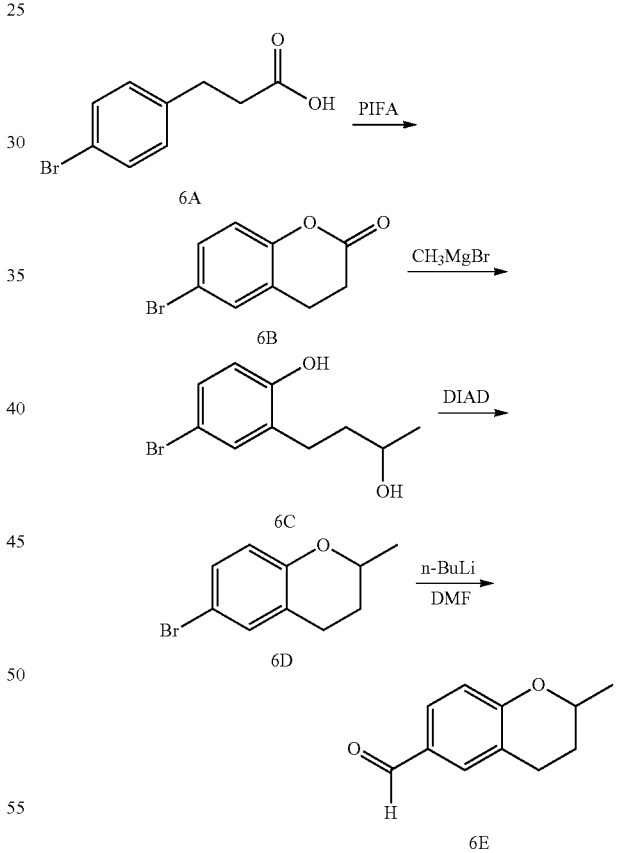

Step 1

To a mixture of compound 6A (70.2 g, 308 mmol) and BF$_3$.OEt$_2$ (66 g, 462 mmol) in TFA, was added PIFA (198.6 g, 462 mmol) dropwise. The mixture was allowed to stir at 40° C. for 45 hours, and then TFA was removed in vacuo. The mixture was poured into H$_2$O, and extracted with ethyl acetate. The organic extract was washed with NaHCO$_3$ solution and brine, dried over Na$_2$SO$_4$, filtered and concentrated in vacuo. The residue obtained was purified using flash column chromatography (petroleum ether:ethyl acetate=20:1~10:1) to provide compound 6B.

Step 2

To a mixture of compound 6B (3.41 g, 14.956 mmol) in THF at 0° C. was added CH₃MgBr (32.9 mmol). The mixture was allowed to stir at 0~20° C. for 16 hours, and then the mixture was quenched with NH₄Cl, and extracted with ethyl acetate. The organic extract was washed with H₂O and brine, dried over Na₂SO₄, filtered and concentrated in vacuo. The residue obtained was purified using flash column chromatography (petroleum ether:ethyl acetate=20:1~5:1) to provide compound 6C.

Step 3

To a mixture of compound 6C (3.05 g, 12.5 mmol) in and PPh₃ (4.912 g, 18.75 mmol) in DCM, then DIAD (4.84 g, 18.75 mmol) was added dropwise at 0° C. The mixture was allowed to stir at 0~20° C. for 2 hours, then the reaction was quenched with H₂O, extracted with ethyl acetate. The organic extract was washed with H₂O and NaCl, dried over Na₂SO₄. After filtration and concentration, the residue obtained was purified using flash column chromatography (petroleum ether:ethyl acetate=2001~30:1) to provide compound 6D.

Step 4

To a mixture of compound 6D (2.7 g, 11.947 mmol) in THF was added n-BuLi (13.75 mmol) at −78° C. The mixture was allowed to stir at −78° C. for 5 min, and then DMF (1.3 g, 18 mmol) was added dropwise. After stirring for 30 minutes, reaction mixture was quenched with NH₄Cl, extracted with ethyl acetate. The organic extract was washed with H₂O and brine, dried over Na₂SO₄. After filtration and concentration, the residue obtained was purified using flash column chromatography (petroleum ether:ethyl acetate=100:1~30:1) to provide racemic compound 6E. (ESI) m/z: 177.1 [M+H]⁺.

Example 7

Preparation of Intermediate Compound 7D

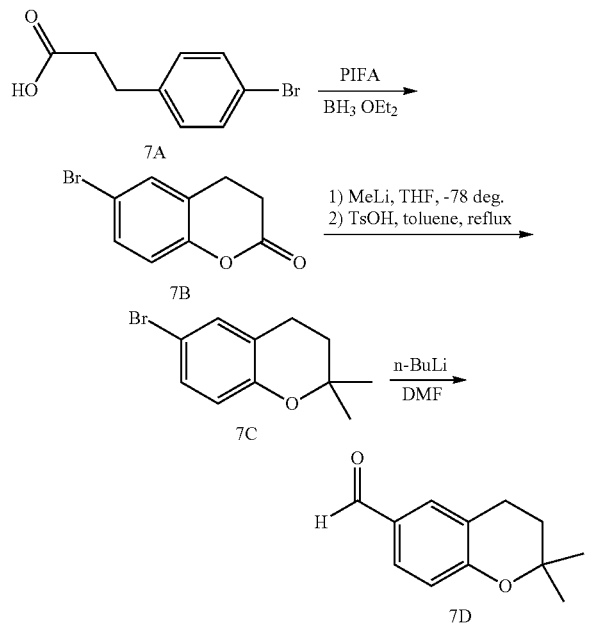

Step 1

To a solution of compound 7A (37 g, 162.28 mmol) and PIFA (104.67 g, 243.42 mmol) in TFA (500 mL) was added BF₃.OEt₂ (34.57 g, 243.42 mmol) dropwise at room temperature under nitrogen. The mixture was allowed to stir at 40-60° C. for 48 hours, then concentrated in vacuo. The residue obtained was dissolved in ethyl acetate, basified to pH 13 using aq. NaOH, and filtered. The filtrate was extracted with ethyl acetate and the organic extract was washed with brine, dried over sodium sulfate, and concentrated in vacuo. The residue obtained was purified using flash column chromatography on silica gel (petroleum ether:ethyl acetate=10:1 to provide compound 7B as a solid. MS (ESI) m/z: 227.1 [M+H]⁺

Step 2

To a solution of compound 7B (1.12 g, 5 mmol) in THF (10 mL) at 0° C. was added MeLi (1.6 M in ether, 7.8 mL, 12.5 mmol) dropwise under nitrogen. The mixture was allowed to stir at room temperature for 16 hours, re-cooled to 0° C. using an ice bath, and aq. 1M HCl (2.5 mL) was added dropwise. The layers were separated, and the aqueous layer was extracted with ethyl acetate. The organic extract was washed with brine, dried over sodium sulfate, filtered and concentrated in vacuo. The residue obtained was dissolved in toluene (20 mL), TsOH.H₂O (19 mg, 0. mmol) was added, and the mixture was refluxed for 16 hours in a Dean-Stark apparatus. After removed of the solvent in vacuo, the residue obtained was purified using flash column chromatography on silica gel (petroleum ether:ethyl acetate=100:1 to provide compound 7C as an oil. ¹H-NMR (CDCl₃, 400 MHz): δ 7.07-7.09 (m, 2H), 6.57 (d, J=8.4 Hz, 1H), 2.66 (t, J=6.8 Hz, 2H), 1.70 (t, J=6.8 Hz, 2H), 1.24 (s, 6H).

Step 3

To a solution of compound 7C (390 mg, 1.64 mmol) in THF (10 mL) was added n-BuLi (2.5 M in hexane, 1.96 mL, 4.92 mmol) dropwise at −78° C. under nitrogen. The mixture was allowed to stir at −78° C. for 10 minutes. Then DMF (0.76 ml, 9.83 mmol) was added. The resultant mixture was allowed to stir at −78° C. for 1 hour. The reaction was quenched by addition aq. NH₄Cl, extracted with ethyl acetate. The organic extract was washed with brine, dried over sodium sulfate, filtered and concentrated in vacuo, and the residue obtained was purified using pre-TLC eluting with petroleum ether:ethyl acetate=20:1 to provide compound 7D as an oil. ¹H-NMR (CDCl₃, 400 MHz): δ 9.76 (s, 1H), 7.54-7.56 (m, 2H), 6.79 (d, J=8.8 Hz, 1H), 2.77 (t, J=6.4 Hz, 2H), 1.78 (t, J=6.4 Hz, 2H), 1.30 (s, 6H).

Example 8

Preparation of Intermediate Compound 8C

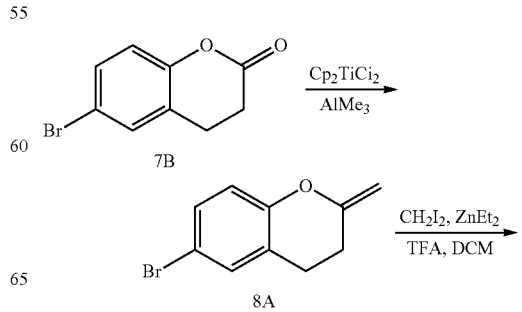

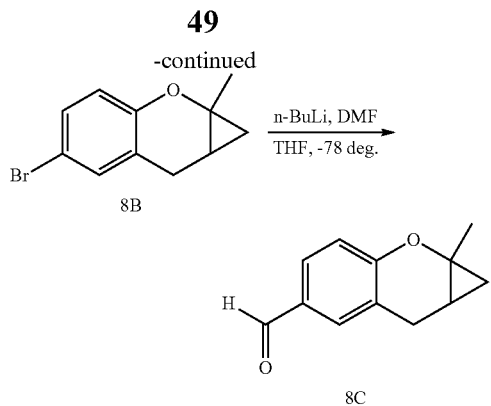

Step 1

A trimethylaluminum solution (2.0 M in toluene, 20 mL, 40 mmol) at 0° C. was added dropwise to $Cp_2TiCl_2$ (5 g, 20 mmol) under nitrogen. After the addition, the resulting solution was allowed to stir at room temperature for 24 hours, then was cooled in a dry ice-acetone bath. A solution of compound 7B (4.48 g, 20 mmol) in THF (20 mL) was added dropwise by syringe to the cooled stirring solution over 5-10 minutes. After the addition, the reaction mixture was allowed to warm to room temperature and stirred for 30 minutes. 50 drops of aq 1M NaOH was added over 10 minutes, and stirring continued until gas evolution essentially ceased. The reaction mixture was filtered, and concentrated in vacuo, and the residue obtained was purified using flash column chromatography on silica gel (petroleum ether) to provide compound 8A as an oil. $^1$H-NMR (CDCl$_3$, 400 MHz): δ 7.17-7.24 (m, 2H), 6.75 (d, J=8.8 Hz, 1H), 4.56 (s, 1H), 4.16 (s, 1H), 2.76 (t, J=6.8 Hz, 2H), 2.54 (t, J=6.8 Hz, 2H).

Step 2

$CH_2I_2$ (12.44 g, 46.4 mmol) was added dropwise to a −78° C. stirred solution of $ZnEt_2$ (1 M in hexane, 23.2 mL, 23.2 mmol) in dichloromethane (23 mL) under nitrogen, and the mixture was allowed to stir at 0° C. for 15 minutes resulting in the formation of a white precipitate. TFA (2.646 g, 23.2 mmol) was added to the mixture resulting in the rapid formation of a homogeneous solution which was allowed to stir at 0° C. for 15 minutes. A solution of compound 8A (2.6 g, 11.6 mmol) in dichloromethane (10 mL) was then added and the resultant mixture was allowed to stir at room temperature for 16 hours. Saturated $Na_2$EDTA (50 mL) was then added, and the resultant mixture was vigorously stirred for 5 minutes, then diluted with dichloromethane (100 mL) and saturated aq. $NaHCO_3$ (100 mL). The aqueous layer was extracted with dichloromethane and the organic extract was washed with brine, dried over sodium sulfate, filtered and concentrated in vacuo. The residue obtained was purified using flash column chromatography on silica gel (petroleum ether) to provide compound 8B as a solid. $^1$H-NMR (CDCl$_3$, 400 MHz): δ 7.11-7.16 (m, 2H), 6.65 (d, J=8.4 Hz, 1H), 3.08-3.13 (m, 1H), 2.86-2.90 (m, 1H), 1.54 (s, 3H), 1.20-1.25 (m, 1H), 0.92-0.95 (m, 1H), 0.54-0.58 (m, 1H).

Step 3

To a solution of compound 8B (0.8 g, 3.36 mmol) in THF (20 mL) at −78° C. was added n-BuLi (2.5 M in hexane, 4 mL, 10 mmol) dropwise under nitrogen. The mixture was allowed to stir at −78° C. for 5 minutes, then DMF (1.54 mL, 20 mmol) was added. The resultant mixture was allowed to stir at −78° C. for 1 hour and the reaction was quenched by addition aq. $NH_4Cl$, and extracted with ethyl acetate. The organic extract was washed with brine, dried over sodium sulfate, filtered and concentrated in vacuo, and the residue obtained was purified using flash column chromatography on silica gel (petroleum ether:ethyl acetate=100:1 to provide compound 8C as an oil. $^1$H-NMR (CDCl$_3$, 400 MHz): δ 9.75 (s, 1H), 7.50-7.57 (m, 2H), 6.82 (d, J=8.4 Hz, 1H), 3.11-3.16 (m, 1H), 2.95-2.99 (m, 1H), 1.54 (s, 3H), 1.23-1.28 (m, 1H), 0.88-0.94 (m, 1H), 0.58-0.62 (m, 1H).

Example 9

Preparation of Compounds 1 and 2

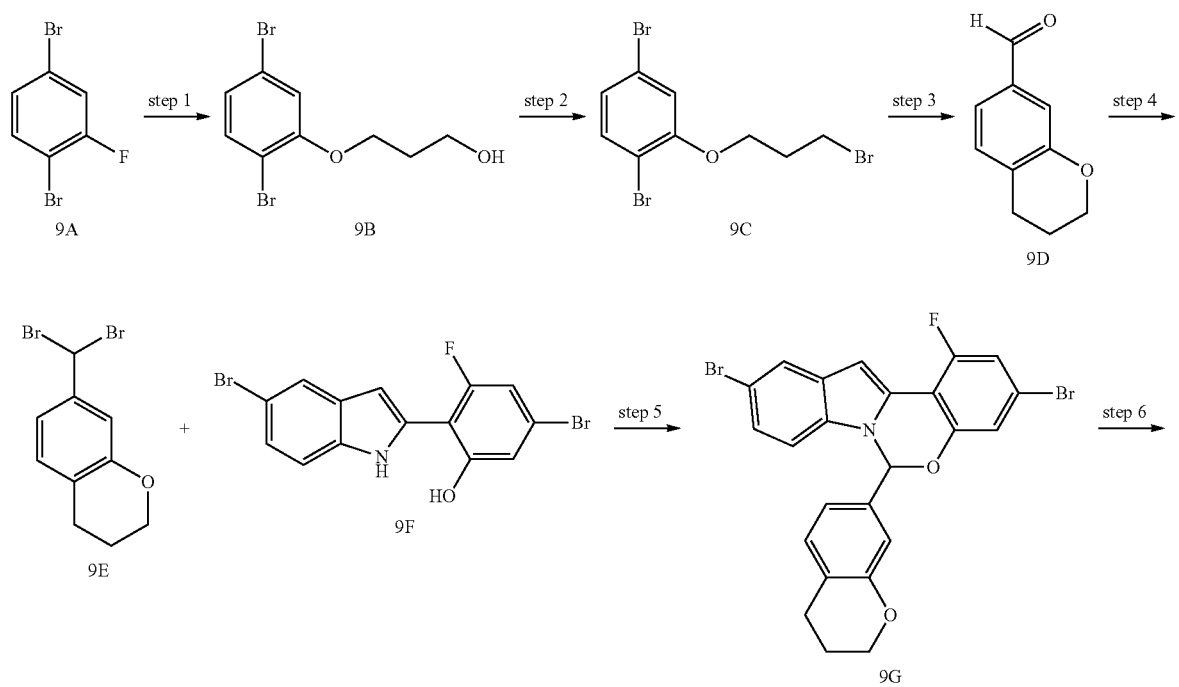

-continued
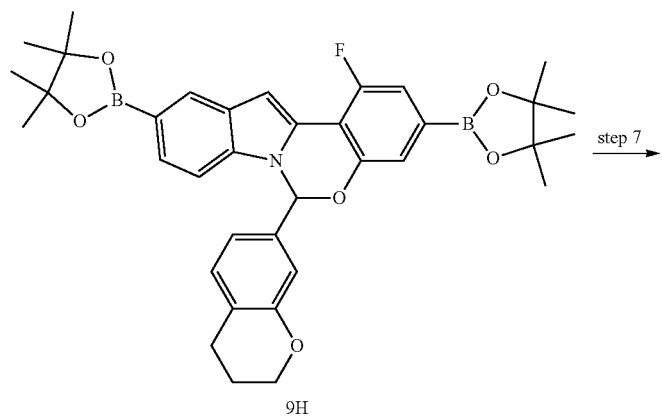
9H
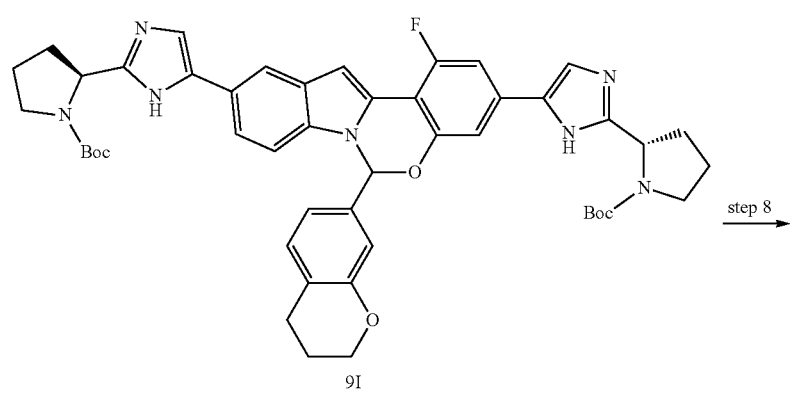
9I
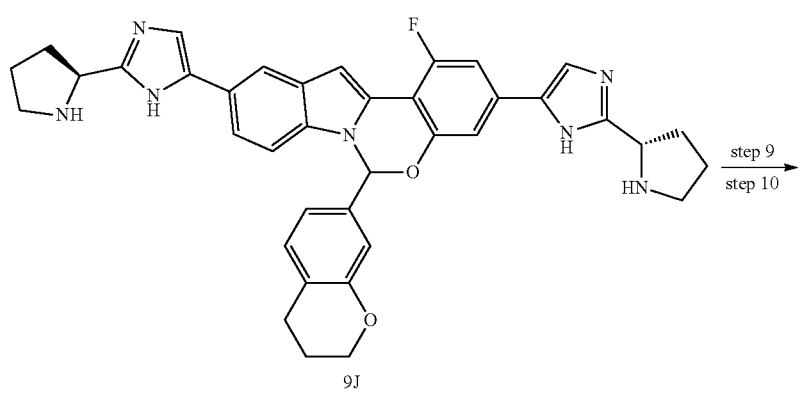
9J
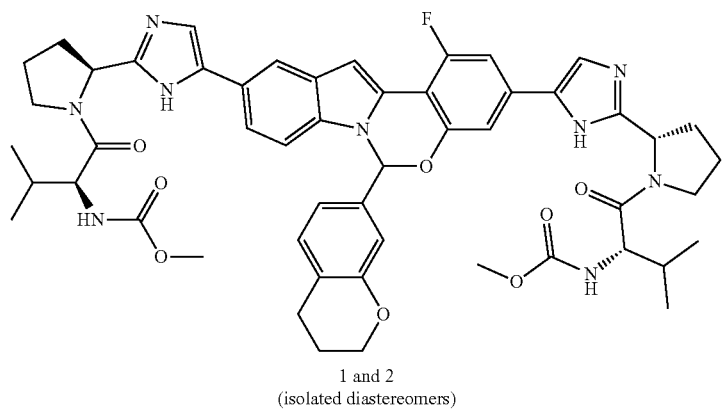
1 and 2
(isolated diastereomers)

Step 1

To a mixture of compound 9A (20 g, 78.7 mmol), ethylene glycol (110 mL) and NMP (10 mL) was added t-BuOK (31.2 g, 280 mmol) slowly. The mixture was heated to 100° C. overnight. The mixture was poured into ice water, and extracted with ethyl acetate. The organic extract was washed with brine, dried and concentrated in vacuo. The residue obtained was purified using flash column chromatography on silica gel to provide 9B as an oil. MS (ESI): m/e 311 [M+H]$^+$.

Step 2

To a solution of compound 9B (17 g, 54.8 mmol) in toluene (200 mL) was added PBr$_3$ (7.4 g, 27.4 mmol) below 0° C., and the mixture was heated to 100° C. for 2 hours. TLC showed the compound 2 was consumed up. The mixture was poured into ice-water and extracted with ethyl acetate. The organic phase was washed with NaHCO$_3$ and brine, dried over Na$_2$SO$_4$, and concentrated in vacuo. Purification using flash column chromatography on silica gel provided compound 9C as an oil. $^1$H-NMR (CDCl$_3$) δ: 7.35-7.37 (d, J=8.4 Hz, 1H), 7.01-7.02 (m, 1H), 6.95-6.98 (m, 1H), 4.11-4.14 (t, J=5.6 Hz, 2H), 3.63-3.66 (t, J=6.4 Hz), 2.32-2.38 (m, 2H).

Step 3

To a solution of compound 9C (16.6 g, 50.6 mmol) in dry THF (300 mL) was added n-BuLi (20 mL, 2.5 M, 50.6 mmol) at −78° C. dropwise, and stirred at this temperature for 30 minutes. Then, another batch of n-BuLi (20 mL, 2.5 M, 50.6 mmol) was added dropwise. After stirring for 15 minutes, a solution of DMF (7.3 g, 100 mmol) in THF (20 mL) was added dropwise. The mixture was warmed back to RT slowly and stirred for 30 minutes. A saturated aqueous NH$_4$Cl was added to quench the reaction. The mixture was extracted with ethyl acetate. The organic phase was washed with brine, dried over Na$_2$SO$_4$, and concentrated in vacuo. Purification using flash column chromatography on silica gel provided 9D as a solid. $^1$H-NMR (CDCl$_3$) δ: 9.85 (s, 1H), 7.30-7.32 (m, 1H), 7.23-7.24 (m, 1H), 7.13-7.15 (m, 1H), 4.17-4.20 (t, J=5.2 Hz, 2H), 1.98-2.03 (m, 2H).

Step 4

To a solution of triphenyl phosphite (11.3 g, 43.2 mmol) in dry DCM (150 mL) was added dropwise bromine (6.87 g, 43.2 mmol) at −15° C. After 30 minutes, a solution of compound 9D (3.5 g, 21.6 mmol) in DCM (15 mL) was added dropwise. The reaction mixture was allowed to stir at room temperature overnight.

The mixture was concentrated in vacuo, and the residue obtained was purified using flash column chromatography on silica gel to provide 9E as a solid. $^1$H-NMR (CDCl$_3$) δ: 6.98-7.01 (m, 3H), 6.54 (s, 1H), 4.16-4.19 (t, J=5.2 Hz, 2H), 2.76-2.79 (t, J=6.4 Hz, 2H), 1.95-2.01 (m, 2H).

Step 5

A mixture of compound 9E (862 mg, 2.24 mmol), 9F (760 mg, 2.5 mmol), and K$_2$CO$_3$ (10 mmol) in 11 mL of DMF was heated to 100° C. for 3 hours. The mixture was concentrated in vacuo, and dissolved with DCM and water. The aqueous phase was extracted with DCM. The combined organic phase was washed with brine, dried over Na$_2$SO$_4$ and concentrated in vacuo. The residue obtained was purified using flash column chromatography on silica gel to provide compound 9G. $^1$H-NMR (CDCl$_3$, 400) δ: 7.79 (s, 1H), 7.20-7.22 (m, 1H), 7.07 (s, 1H), 6.97-7.01 (m, 3H), 6.90-6.92 (m, 1H), 6.39-6.45 (m, 1H), 6.39 (s, 1H), 4.08-4.11 (t, J=4.8 Hz, 1H), 2.68-2.71 (t, J=6.4 Hz, 2H), 1.90-1.95 (m, 2H).

Step 6

To a solution of compound 9G (900 mg, 1.7 mmol) in 1,4-dioxane was added bis pinacolato borate (2.0 mmol) and Pd(dppf)Cl$_2$ (0.09 mmol) and KOAc (5.1 mmol). The reaction mixture was allowed to stir under N$_2$ and heated to 110° C. for about 15 hours. The reaction mixture was then concentrated in vacuo, and the residue obtained was purified using flash column chromatography on silica gel to provide compound 9H. MS (ESI): m/z 624 [M+H]$^+$.

Step 7

A suspension of compound 9H (1140 mg, 1.83 mmol), Br-imidazole-1 (2.2 mmol), Pd(dppf)$_2$Cl$_2$ (0.1 mmol), Na$_2$CO$_3$ (5.5 mmol) and in THF/H$_2$O (10:1, 10 mL) was refluxed at 75° C. overnight under N$_2$. The mixture was then filtered, and the filtrate was washed with water (50 mL) and extracted with ethyl acetate (100 mL), and the organic extract was washed with brine, dried over anhydrous sodium sulfate. and concentrated in vacuo. The residue obtained was purified using flash column chromatography on silica gel (petroleum ether/ethyl acetate=8:1 to 5:1) to provide compound 9I. MS (ESI) m/e (M+H$^+$): 842.

Step 8

Compound 9I (400 mg, 0.48 mmol) was added into a solution of HCl/CH$_3$OH (5 mL, 3M) and the resulting reaction was allowed to stir at room temperature for 3 hours. The reaction mixture was then concentrated in vacuo to provide compound 9J, which was used without further purification. MS (ESI) m/z (M+H$^+$): 642.

Step 9

To a mixture of compound 9J (355 mg, 0.45 mmol), cap-1 (0.99 mmol) and DIPEA (3.6 mmol) in DMF (5 mL) was added HATU (1.0 mmol). The resulting mixture was allowed to stir at room temperature until LCMS showed that the starting material was completely consumed. The reaction mixture was then directly purified using preparative HPLC to provide a racemic mixture of compounds 1 and 2. $^1$H-NMR (MeOD 400 MHz) δ: 7.90-7.96 (m, 1H), 7.80-7.81 (m, 1H), 7.41-7.45 (m, 1H), 7.25-7.37 (m, 3H), 7.09-7.19 (m, 3H), 6.88-6.92 (m, 1H), 6.43-6.59 (m, 1H), 6.28 (s, 1H), 5.15-5.24 (m, 2H), 4.19-4.23 (m, 2H), 4.02-4.09 (m, 4H), 3.94-3.95 (m, 2H), 3.64 (s, 6H), 2.64-2.65 (m, 2H), 2.52-2.55 (m, 2H), 2.01-2.26 (m, 8H), 1.85-1.89 (m, 2H), 0.97-0.94 (m, 12H). MS (ESI) m/z (M+H$^+$): 956.5.

Step 10

A racemic mixture of Compounds 1 and 2 was separated using chiral SFC to provide pure diastereomers 1 and 2. SFC: Column: Chiralpak AS-H, 250×20 mm, 5 µm, Mobile phase: 40% of EtOH (0.05% DEA) in CO$_2$, Flow rate: 50 mL/min, wavelength: 220 nm.

1: $^1$H-NMR (MeOH-d$_4$, 400 MHz) δ: 7.99 (s, 1H), 7.84 (s, 1H), 7.40-7.44 (m, 2H), 7.22-7.27 (m, 3H), 7.14-7.15 (m, 1H), 6.90-6.92 (m, 1H), 6.43-6.45 (m, 1H), 6.30 (s, 1H), 5.16-5.25 (m, 2H), 4.18-4.23 (m, 2H), 4.02-4.07 (m, 4H), 3.83-3.88 (m, 2H), 3.64 (s, 6H), 2.63-2.67 (m, 2H), 2.50-2.54 (m, 2H), 2.24-2.26 (m, 2H), 2.13-2.19 (m, 4H), 2.01-2.08 (m, 2H), 1.85-1.87 (m, 2H). MS (ESI) m/z (M+H$^+$): 956.5.

2: $^1$H-NMR (MeOH-d$_4$, 400 MHz) δ: 7.92 (s, 1H), 7.81 (s, 1H), 7.69 (s, 1H), 7.41-7.46 (m, 2H), 7.25-7.28 (m, 2H), 7.14 (m, 1H), 7.08-7.09 (m, 1H), 6.88-6.90 (m, 1H), 6.40-6.42 (m, 2H), 6.29 (s, 1H), 5.17-5.23 (m, 2H), 4.20-4.24 (m, 2H), 4.00-4.08 (m, 4H), 3.85-3.89 (m, 2H), 3.63 (s, 6H), 2.62-2.64 (m, 2H), 2.48-2.57 (m, 2H), 2.21-2.32 (m, 2H), 2.05-2.17 (m, 6H), 0.86-0.96 (m, 12H). MS (ESI) m/z (M+H$^+$): 956.6.

Example 10

Preparation of Compounds 3-6

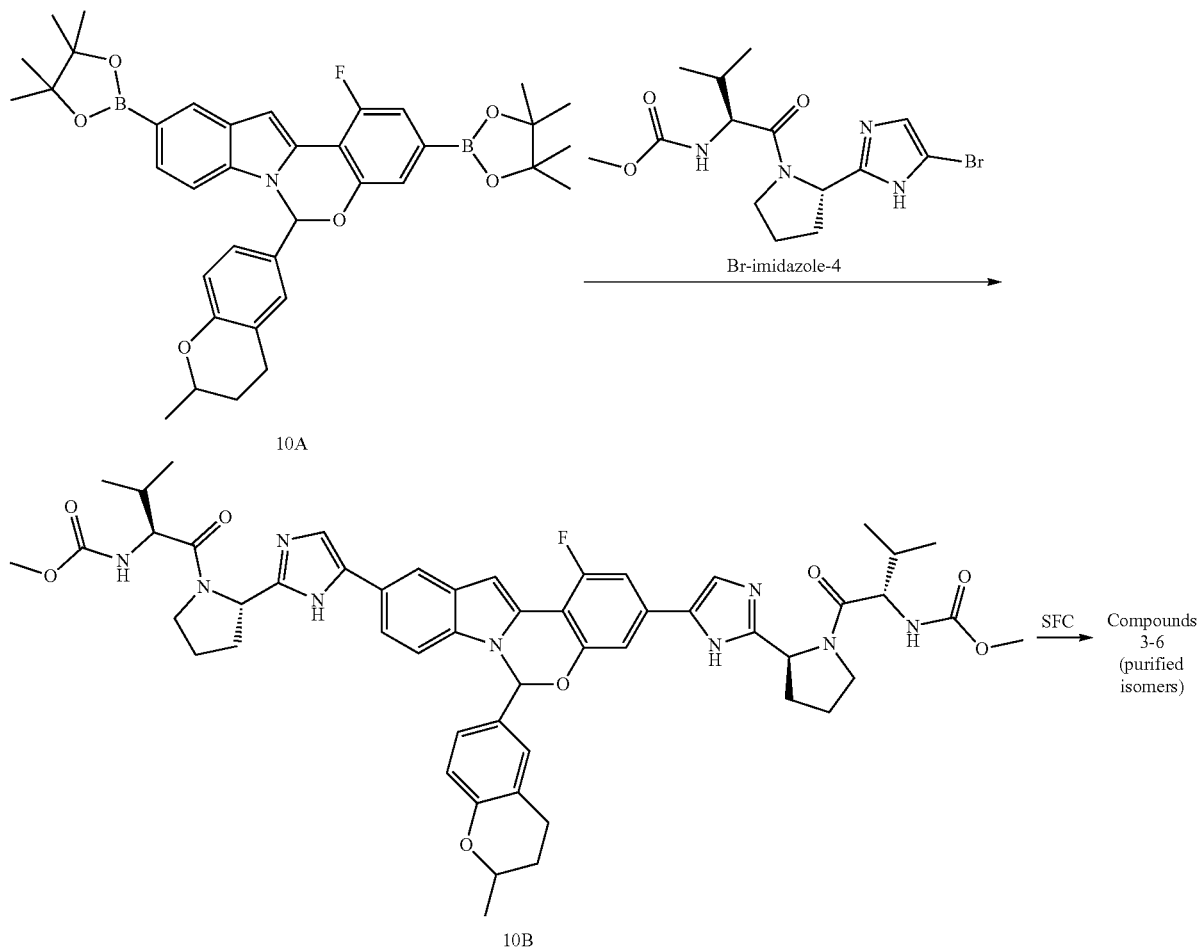

Step 1

A suspension of compound 10A (made using the methodology described in Example 9 to provide intermediate compound 911, 500 mg, 0.79 mmol), Br-imidazole-4 (600 mg, 1.6 mmol), Pd(dppf)$_2$Cl$_2$ (60 mg, 0.08 mmol) and Na$_2$CO$_3$ (400 mg, 3.6 mmol) in THF/H$_2$O (10:1, 70 mL) was allowed to stir at reflux for about 15 hours under N$_2$. The reaction mixture was filtered, and the filtrate was washed with water (100 mL) and extracted with ethyl acetate (200 mL). The organic extract washed with brine, dried over anhydrous sodium sulfate, filtered, and concentrated in vacuo. The residue obtained was purified using HPLC (acidic) to provide 10B as a mixture of four isomers.

Step 2

Isomeric mixture 10B was resolved using chiral SFC to provide the four purified diastereomers as compounds 3-6. Conditions: Chiralpak AS-H 250×20 mm, 5 μm Mobile phase: 40% of EtOH (0.05% DEA) in CO$_2$, Flow rate: 50 mL/min, wavelength: 220 nm.

3: $^1$H-NMR (MeOH-d$_4$, 400 MHz) δ: 8.00 (s, 1H), 7.85 (s, 1H), 7.73 (s, 1H), 7.434-7.135 (m, 6H), 6.79-6.74 (m, 2H), 6.64-6.62 (d, 1H), 5.26-5.17 (m, 2H), 4.24-4.20 (m, 2H), 4.10-4.04 (m, 3H), 3.88-3.84 (m, 2H), 3.65-3.65 (m, 6H), 2.70-2.51 (m, 4H), 2.25-1.93 (m, 7H), 1.02-1.51 (m, 1H), 1.37-1.30 (m, 3H), 0.94-0.87 (m, 12H). MS (ESI) m/z: 970.7 [M+H]$^+$:

4: $^1$H-NMR (MeOH-d$_4$, 400 MHz) δ: 7.94 (s, 1H), 7.70 (s, 2H), 7.42-7.27 (m, 3H), 7.15-7.11 (m, 3H), 6.76-6.73 (m, 2H), 6.62-6.60 (d, 1H), 5.24-5.16 (m, 2H), 4.20 (m, 2H), 4.08-4.03 (m, 3H), 3.85 (m, 2H), 3.63 (m, 6H), 2.76-2.67 (m, 1H), 2.57-2.43 (m, 3H), 2.24-1.91 (m, 9H), 1.58-1.48 (m, 1H), 1.29-1.28 (m, 3H), 0.99-0.88 (m, 12H). MS (ESI) m/z: 970.7 [M+H]$^+$.

5: $^1$H-NMR (MeOH-d$_4$, 400 MHz) δ: 7.95 (s, 1H), 7.78 (s, 1H), 7.71 (s, 1H), 7.43-7.28 (m, 3H), 7.17-7.14 (m, 3H), 6.76-6.71 (m, 2H), 6.62-6.59 (d, 1H), 5.24-5.15 (m, 2H), 4.23-4.19 (m, 2H), 4.07-4.02 (m, 3H), 3.87-3.85 (m, 2H), 3.63 (m, 6H), 2.68-2.46 (m, 4H), 2.24-1.9 (m, 9H), 1.59-1.52 (m, 1H), 1.29-1.28 (m, 3H), 0.93-0.86 (m, 12H). MS (ESI) m/z: 970.7 [M+H]$^+$.

6: $^1$H-NMR (MeOH-d$_4$, 400 MHz) δ: 7.98 (s, 1H), 7.86 (s, 1H), 7.72 (s, 1H), 7.41-7.27 (m, 3H), 7.22-7.10 (m, 3H), 6.77-6.74 (m, 2H), 6.64-6.61 (d, 1H), 5.24-5.16 (m, 2H), 4.23-4.18 (m, 2H), 4.07-4.03 (m, 3H), 3.87-3.83 (m, 2H), 3.64 (m, 6H), 2.73-2.51 (m, 4H), 2.24-1.92 (m, 9H), 1.57-1.53 (m, 1H), 1.30-1.28 (m, 3H), 0.93-0.86 (m, 12H). MS (ESI) m/z: 970.7 [M+H]$^+$.

The following compounds of the present invention were made using the methods described in the Example above, and substituting the appropriate reagents and/or reactants:

| | Structure | Isomer | Observed [M + H]+ |
|---|---|---|---|
| 7 | 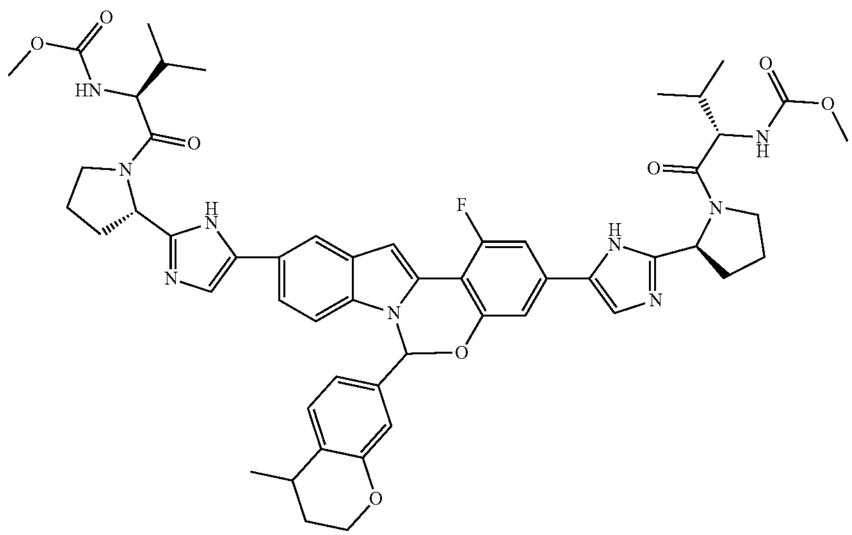 | Isomer 1 | 970.5 |
| 8 | | Isomer 2 | 970.5 |
| 9 | | Isomer 3 | 970.6 |
| 10 | | Isomer 4 | 970.6 |
| 11 | 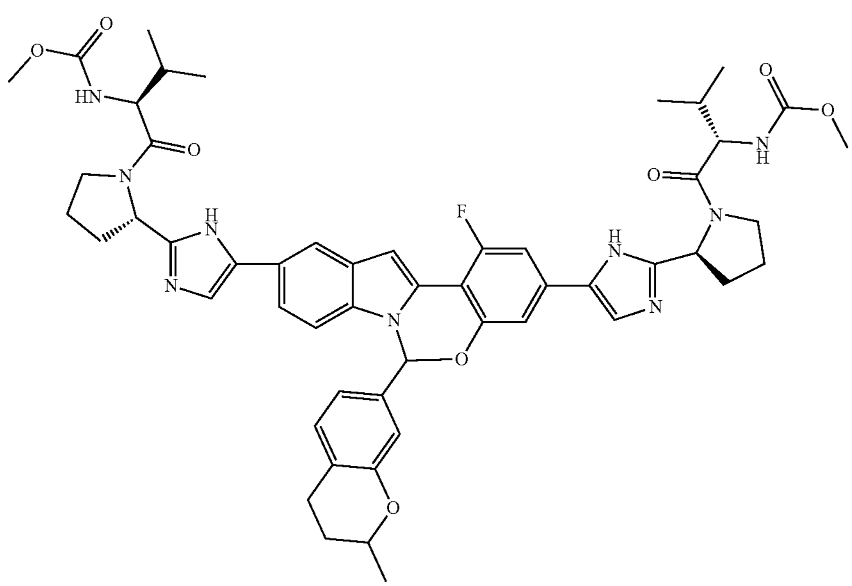 | Isomer 1 | 970.5 |
| 12 | | Isomer 2 | 970.5 |
| 13 | | Isomer 3 | 970.5 |
| 14 | | Isomer 4 | 970.5 |

-continued

| | Structure | Isomer | Observed [M + H]+ |
|---|---|---|---|
| 15 16 | | Isomer 1 Isomer 2 | 982.4 982.5 |
| 17 18 | | Isomer 1 Isomer 2 | 984.5 984.5 |

-continued
| | Structure | Isomer | Observed [M + H]+ |
|---|---|---|---|
| 19 20 | 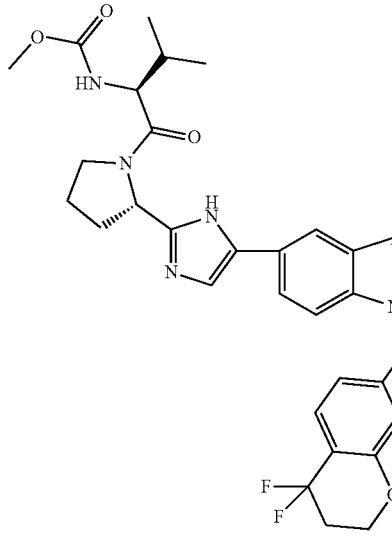 | Isomer 1 Isomer 2 | 92.4 92.4 |
| 21 22 | 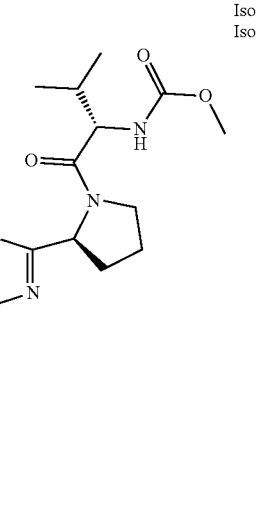 | Isomer 1 Isomer 2 | 84.6 84.6 |

-continued
| | Structure | Isomer | Observed [M + H]+ |
|---|---|---|---|
| 23 24 | 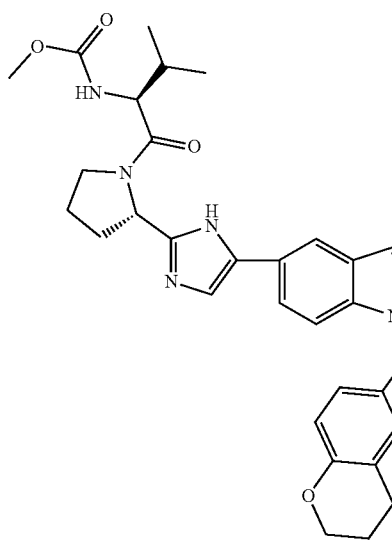 | Isomer 1 Isomer 2 | 56.9 56.9 |
| 25 26 | 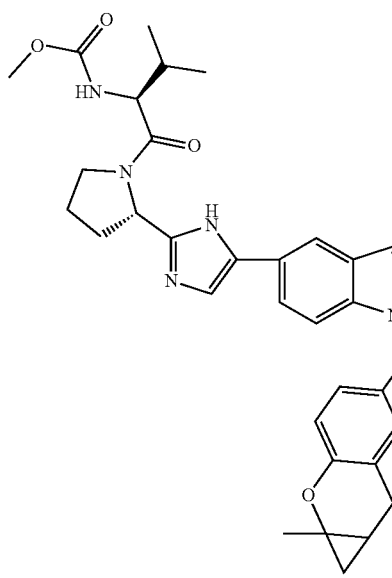 | Isomer 1 Isomer 2 | 82.5 82.5 |

|  | Structure | Isomer | Observed [M + H]+ |
|---|---|---|---|
| 27 28 | 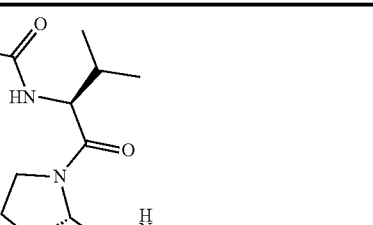 | Isomer 1 Isomer 2 | 70.5 70.5 |
Example 10
Preparation of Compounds 29-30
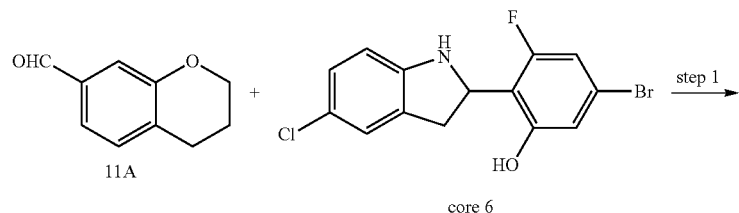
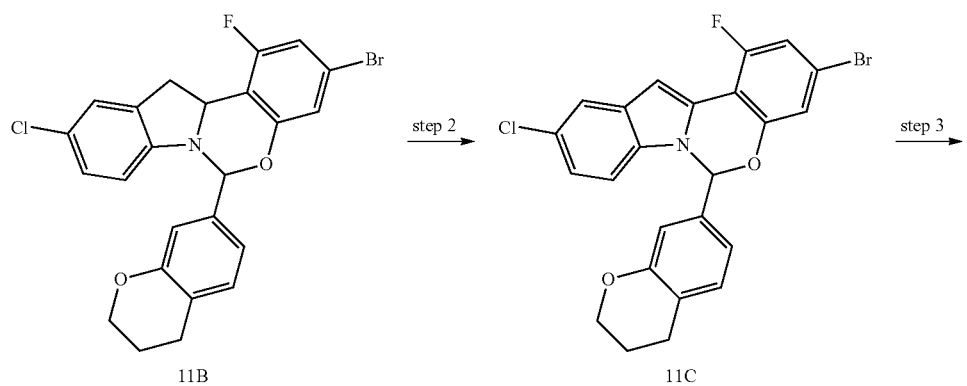

67 68
-continued
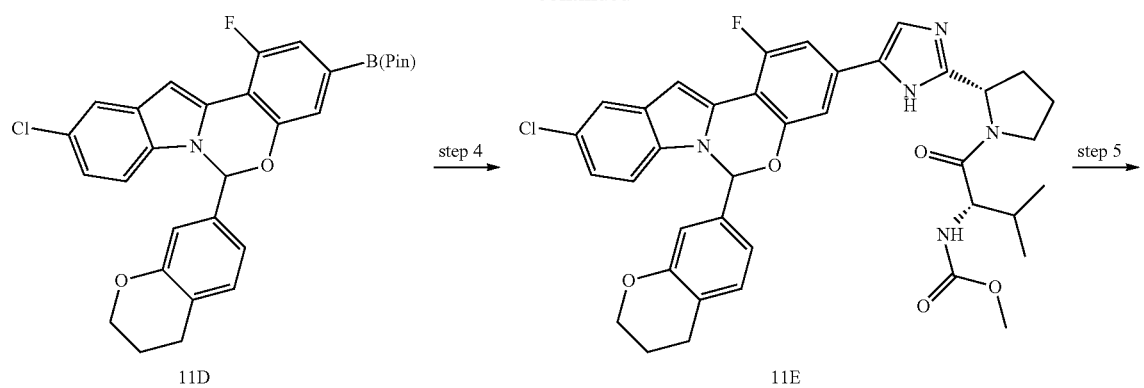
11D → step 4 → 11E → step 5 →
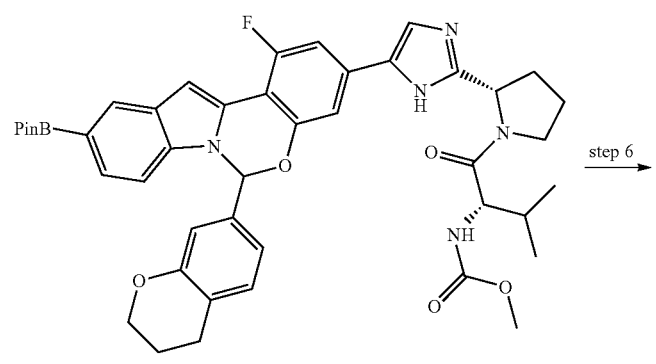
11F → step 6 →
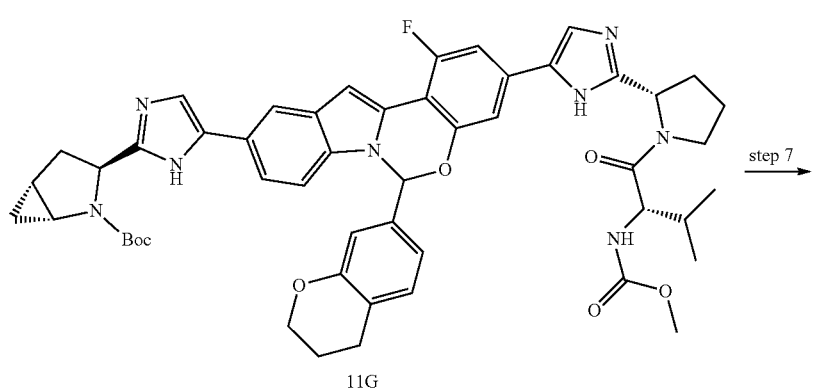
11G → step 7 →
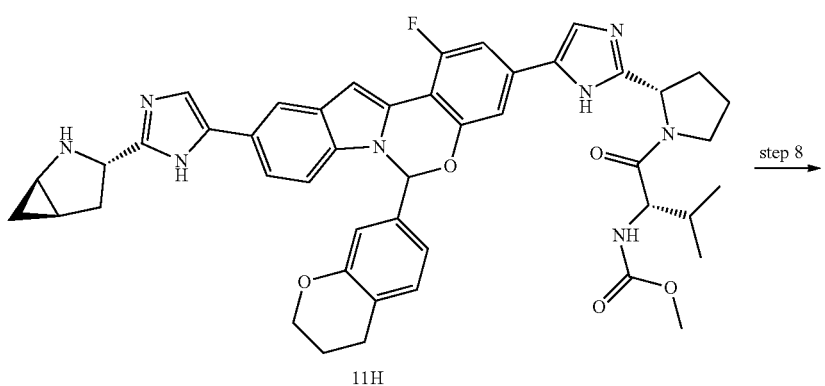
11H → step 8 →

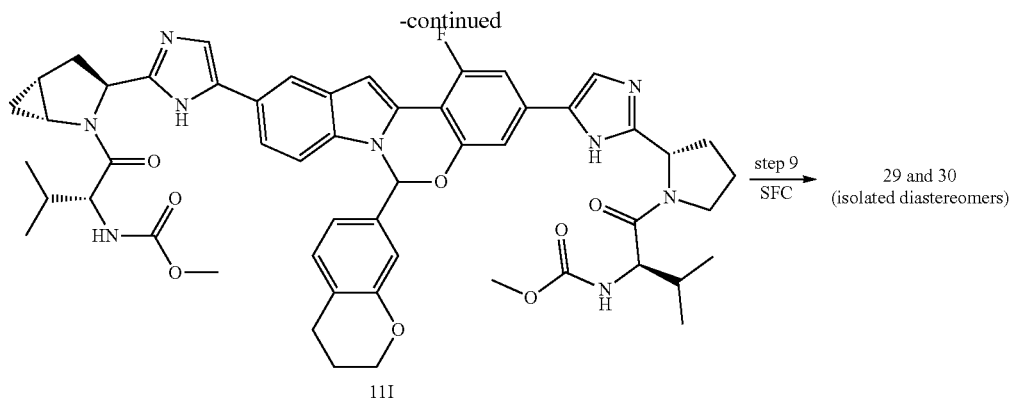

Step 1

To a mixture of compound 11A (20 g, 0.12 mole) and core 6 (38 g, 0.12 mole) in anhydrous CH$_3$CN (400 mL) was added TFA (0.1 mL) at room temperature. The mixture was agitated for 6 hours at room temperature and the solid formed was collected by filtration and washed with CH$_3$CN to provide compound 11B.

Step 2

To a solution of compound 11B (48 g, 98.6 mmol) in dry toluene (450 mL) was added DDQ (33.6 g, 0.15 mole). The reaction was allowed to stir at reflux for 2 hours, then concentrated in vacuo and the resulting residue was diluted with EtOAc. The resulting solution was washed with saturated NaS$_2$O$_3$ aqueous and brine, dried over Na$_2$SO$_4$, filtered and concentrated in vacuo. The residue obtained was washed with MeOH, filtered and the collected solid was dried in vacuo to provide compound 11C (45 g, 93% yield).

Step 3

To a solution of compound 11C (21.3 g, 44 mmol) in 1,4-dioxane (350 mL) was added bis pinacolato borate (13.4 g, 52.7 mmol) and Pd(dppf)Cl$_2$ (3.2 g, 4.4 mmol) and KOAc (8.6 g, 87.8 mmol). The reaction mixture was allowed to stir under N$_2$ and heated to 110° C. for about 15 hours. The reaction mixture was then concentrated in vacuo, and the residue obtained was purified using flash column chromatography on silica gel to provide compound 11D (22 g, 94% yield).

Step 4

A suspension of compound 11D (22 g, 41.4 mmol), Cap 7 (17 g, 45 mmol), Pd(dppf)Cl$_2$ (3 g, 4.1 mmol) and Na$_2$CO$_3$ (8.8 g, 82.7 mmol) in THF—H$_2$O (150-60 mL) was stirred at reflux for 15 hours under N$_2$. The reaction mixture was then filtered, and the filtrate was washed with water and extracted with ethyl acetate. The organic extract was washed with brine, dried over anhydrous sodium sulfate, filtered, and concentrated in vacuo. The residue obtained was purified using flash column chromatography on silica gel to provide 11E (24.1 g, 83.6% yield).

Step 5

To a solution of compound 11E (24.1 g, 34.6 mmol) in 1,4-dioxane (300 mL) was added bis pinacolato borate (10.5 g, 41.2 mmol), X-phos (3.3 g, 6.9 mmol) and Pd$_2$(dba)$_3$ (3.2 g, 3.4 mmol) and KOAc (6.8 g, 69.2 mmol). The reaction mixture was allowed to stir at reflux under N$_2$ for about 15 hours. The reaction mixture was then concentrated in vacuo, and the residue obtained was purified using flash column chromatography on silica gel (petroleum ether:ethyl acetate=1:1) to provide the compound 11F (22 g, 80.6% yield).

Step 6

A suspension of compound 11F (3 g, 3.8 mmol), Br-imidazole-2 (1.37 g, 4.18 mmol), Pd(dppf)Cl$_2$ (278 mg, 2.38 mmol) and Na$_2$CO$_3$ (807 mg, 7.6 mmol) in THF—H$_2$O (25-10 mL) was allowed to stir at reflux under N$_2$ for about 15 hours. The reaction mixture was then filtered, and the filtrate was washed with water and extracted with ethyl acetate. The organic extract was washed with brine, dried over anhydrous sodium sulfate, filtered, and concentrated in vacuo. The residue obtained was purified using flash column chromatography on silica gel to provide 11G (1.9 g, 55% yield).

Step 7

A mixture of compound 11G (910 mg, 1 mmol) in HCl—MeOH (10 mL) was allowed to stir at 25° C. for 30 minutes, and was then concentrated in vacuo to provide the crude compound 11H (810 mg, 100% yield).

Step 8

To a solution of (R)-2-((methoxycarbonyl)amino)-3-methylbutanoic acid (173 mg, 1 mmol) and DIPEA (358 mg, 2 mmol) in DMF (10 mL) was added HATU (380 mg, 1 mmol). The mixture was allowed to stir at 25° C. for 20 minutes, then compound 11H (810 mg, 1 mmol) was added. The reaction was allowed to stir at 25° C. for 30 minutes, then filtered. The reaction mixture was directly purified using prep-HPLC to provide a racemic mixture of diastereomers 29 and 30 (520 mg, 53.7% yield).

Step 9

A racemic mixture of diastereomers 29 and 30 was resolved using chiral SFC to provide pure diastereomers 29 and 30. Conditions: Chiralpak AS-H 250×20 mm, 5 μm Mobile phase: 40% of EtOH (0.05% DEA) in CO$_2$, Flow rate: 50 mL/min, wavelength: 220 nm.

29: $^1$H-NMR (MeOH-d$_4$, 400 MHz) δ: 8.01 (s, 1H), 7.88 (s, 1H), 7.71 (s, 1H), 7.48-7.45 (m, 2H), 7.33-7.12 (m, 4H), 6.90-6.88 (d, 1H, J=8), 6.42-6.40 (m, 1H), 6.29 (s, 1H), 5.19-5.10 (m, 2H), 4.54-4.52 (m, 1H), 4.22-4.20 (m, 1H), 4.03-4.00 (m, 3H), 3.92-3.73 (m, 2H), 3.64-3.63 (m, 6H), 2.66-2.64 (m, 3H), 2.53-2.45 (m, 2H), 2.26-2.00 (m, 6H), 1.87-1.84 (m, 2H), 1.08-0.86 (m, 14H). MS (ESI): m/z 968.5 [M+H]$^+$.

30: MS (ESI): m/z 968.5 [M+H]$^+$.

The following compounds were prepared using the methods described above and by substituting the appropriate reagents and/or reactants:

| ID | Structure | Isomer information | Observed [M + H]+ |
|---|---|---|---|
| 31 32 | 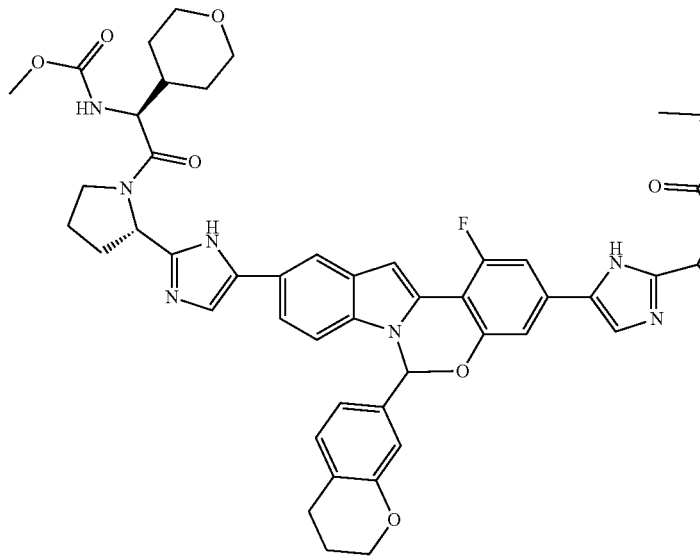 | Isomer 1 Isomer 2 | 998.5 998.5 |
| 33 34 | 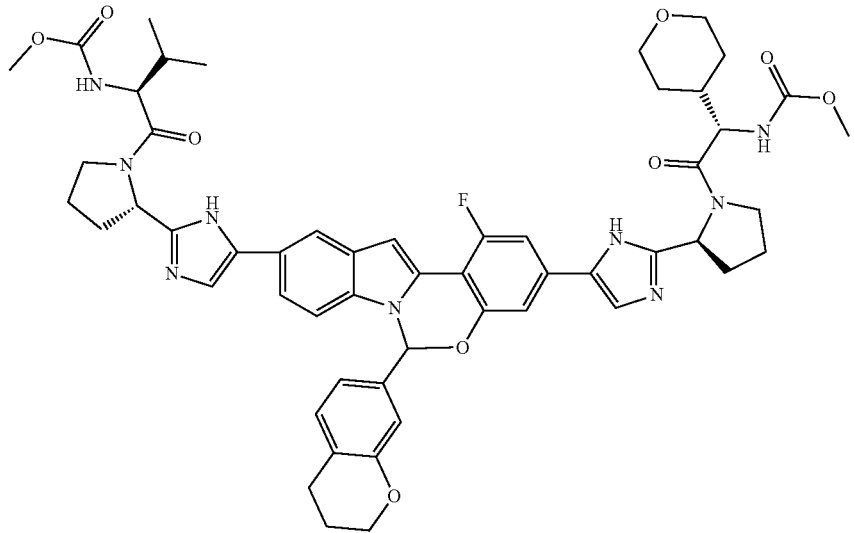 | Isomer 1 Isomer 2 | 998.5 998.6 |

-continued
| ID | Structure | Isomer information | Observed [M + H]+ |
|---|---|---|---|
| 35 | | Isomer 1 | 998.7 |
| 36 | 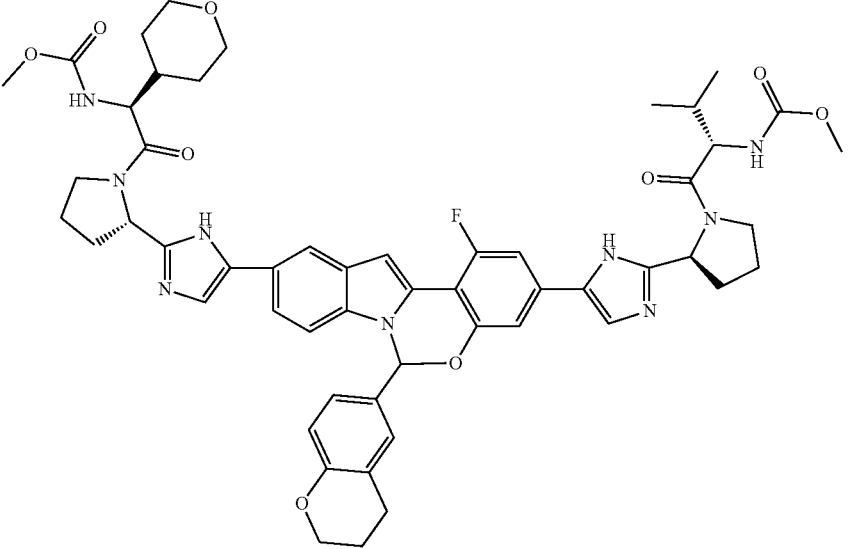 | Isomer 2 | 998.7 |
| 37 | | Isomer 1 | 990.4 |
| 38 | 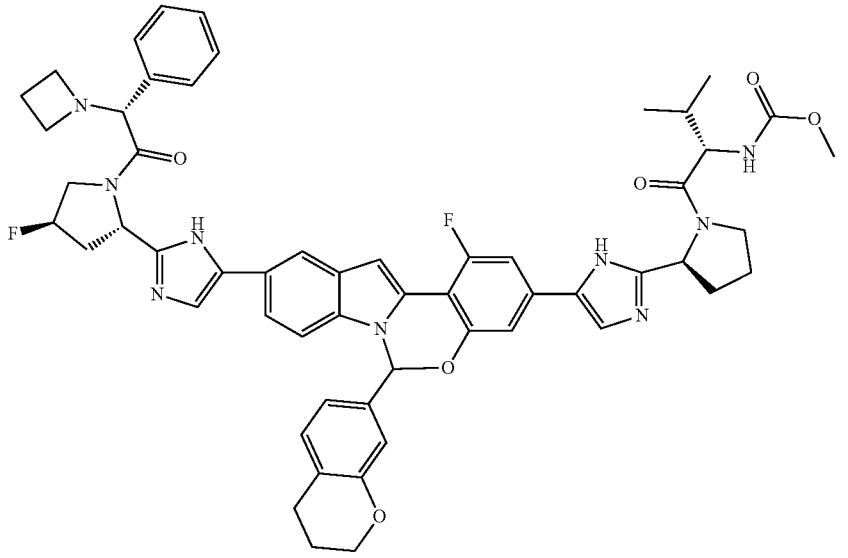 [SMILES: COC(=O)N[C@H](C(=O)N1CCC[C@H]1c1ncc(-c2cc(F)c3c(c2)OC(c2ccc4c(c2)OCCC4)n2c-3cc3cc(-c4cnc([C@@H]5C[C@@H](F)CN5C(=O)[C@@H](c5ccccc5)N5CCC5)[nH]4)ccc32)[nH]1)C(C)C] | Isomer 2 | 990.4 |

| ID | Structure | Isomer information | Observed [M + H]+ |
|---|---|---|---|
| 39 | | Isomer 1 | 986.5 |
| 40 | | Isomer 2 | 986.9 |
| 41 | | Isomer 1 | 974.5 |
| 42 | | Isomer 2 | 974.5 |
| 43 | | Isomer 3 | 974.5 |
| 44 | | Isomer 4 | 974.5 |

-continued

| ID | Structure | Isomer information | Observed [M + H]+ |
|---|---|---|---|
| 45 | | Isomer 1 | 968.5 |
| 46 | | Isomer 2 | 968.5 |
| 47 | | Isomer 1 | 954.4 |
| 48 | | Isomer 2 | 954.4 |
| 49 | | Isomer 1 | 950.5 |
| 50 | | Isomer 2 | 950.5 |

-continued
| ID | Structure | Isomer information | Observed [M + H]+ |
|---|---|---|---|
| 51 52 | 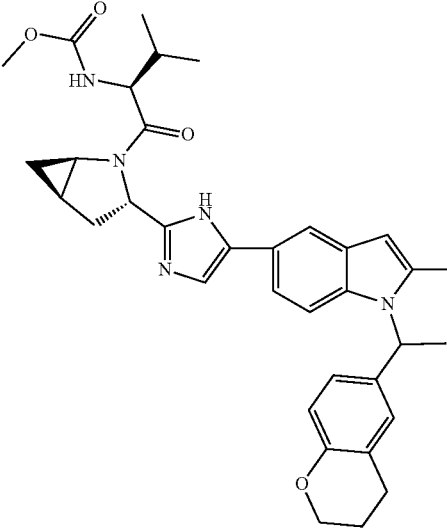 | Isomer 1 Isomer 2 | 950.5 950.5 |
| 53 54 | 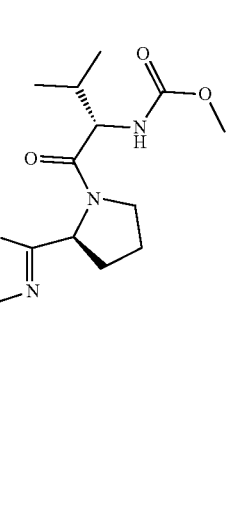 | Isomer 1 Isomer 2 | 1042.6 1042.6 |

-continued

| ID | Structure | Isomer information | Observed [M + H]+ |
|---|---|---|---|
| 55 | | Isomer 1 | 1040.6 |
| 56 | | Isomer 2 | 1040.6 |
| 57 | | Isomer 1 | 1040.6 |
| 58 | | Isomer 2 | 1040.6 |
| 59 | | Isomer 3 | 1040.7 |
| 60 | | Isomer 4 | 1040.6 |

| ID | Structure | Isomer information | Observed [M + H]+ |
|---|---|---|---|
| 61 | | Isomer 1 | 1040.6 |
| 62 | | Isomer 2 | 1040.6 |
| 63 | | Isomer 3 | 1040.6 |
| 64 | | Isomer 4 | 1040.9 |
| 65 | | Isomer 1 | 1038.5 |
| 66 | | Isomer 2 | 1038.5 |

-continued
| ID | Structure | Isomer information | Observed [M + H]+ |
|---|---|---|---|
| 67 | | Isomer 1 | 1038.9 |
| 68 | | Isomer 2 | 10.388 |
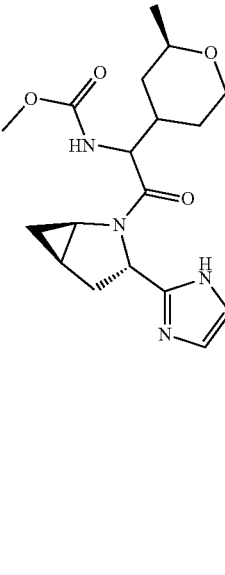
| 69 | | Isomer 1 | 1038.5 |
| 70 | | Isomer 2 | 1038.5 |
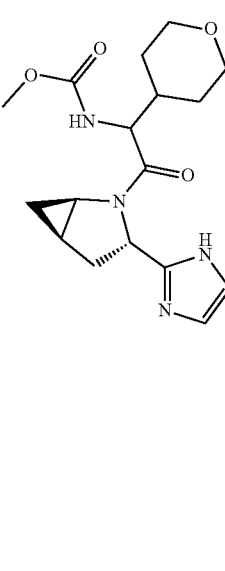

-continued

| ID | Structure | Isomer information | Observed [M + H]+ |
|---|---|---|---|
| 71 | | Isomer 1 | 1026.6 |
| 72 | | Isomer 2 | 1026.2 |
| 73 | | Isomer 1 | 1026.8 |
| 74 | | Isomer 2 | 1026.8 |

-continued

| ID | Structure | Isomer information | Observed [M + H]+ |
|---|---|---|---|
| 75 | | Isomer 1 | 1026.4 |
| 76 | | Isomer 2 | 1026.4 |
| 77 | | Isomer 1 | 1026.5 |
| 78 | | Isomer 2 | 1026.6 |

-continued

| ID | Structure | Isomer information | Observed [M + H]+ |
|---|---|---|---|
| 79 | | Isomer 1 | 1026.5 |
| 80 | | Isomer 2 | 1026.5 |
| 81 | | Isomer 1 | 1024.4 |
| 82 | | Isomer 2 | 1024.4 |

-continued

| ID | Structure | Isomer information | Observed [M + H]+ |
|---|---|---|---|
| 83 | | Isomer 1 | 1023.0 |
| 84 | | Isomer 2 | 1023.0 |
| 85 | | Isomer 1 | 1022.7 |
| 86 | | Isomer 2 | 1022.7 |

| ID | Structure | Isomer information | Observed [M + H]+ |
|---|---|---|---|
| 87 | | Isomer 1 | 1016.5 |
| 88 | | Isomer 2 | 1016.6 |
| 89 | | Isomer 3 | 1016.5 |
| 90 | | Isomer 4 | 1016.5 |
| 91 | | Isomer 1 | 1016.8 |
| 92 | | Isomer 2 | 1016.8 |

| ID | Structure | Isomer information | Observed [M + H]+ |
|---|---|---|---|
| 93 | 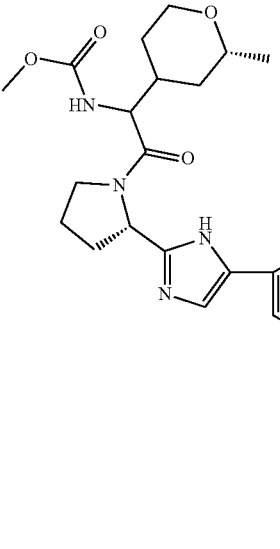 | Isomer 1 | 1012.5 |
| 94 | | Isomer 2 | 1012.5 |

Example 16

Cell-Based HCV Replicon Assays

To measure cell-based anti-HCV activity of compounds of the present invention, two complimentary assays were employed using various replicons. In the first assay ("Replicon Assay A"), replicon cells were seeded at 2000 cells/well in 384-well 384-well flat bottom tissue culture treated clear bottom plate (Corning 3707) in the presence of the test compound. Various concentrations of test compound, typically in 10 serial dilutions, were added to the assay mixture, with the starting concentration ranging from 333.3 nM to 1.667 nM. The final concentration of DMSO was 0.5%. Fetal bovine serum was 5%, in the assay media. Cells were harvested on day 3 by removing media and washing the cells with a suitable wash buffer. The cells were lysed with the addition of 1× Qiagen lysis buffer (Cat #1062731). The replicon RNA level was measured using real time PCR (TaqMan® EZ RT-PCR, Applied Biosystems 403028) with the following primers and probes:

```
Neo Forward:
CCG GCT ACC TGC CCA TTC

Neo Reverse:
CCA GAT CAT CCT GAT CGA CAA G

Neo Probe:
FAM-ACA TCG CAT CGA GCG AGC ACG TAC-Tamra

Cyc probe:
5'JOE-CGCGTCTCCTTTGAGCTGTTTGCA-Tamra-3'

Cyc Forward Primer:
ACGGCGAGCCCTTGG

Cyc Reverse Primer:
TTTCTGCTGTCTTTGGGACCT
```

Cyclophilin RNA was used as endogenous control and was amplified in the same reaction as NS5B (multiplex PCR). The real-time RT-PCR reactions were run on ABI PRISM 7900HT Sequence Detection System using the following program: 50° C. for 2 minutes, 60° C. for 30 minutes, 95° C. for 5 minutes, 40 cycles of 94° C. for 20 sec, 55° C. for 1 minutes.

The amount of HCV replicon RNA per cell was quantified using a linear regression curve for a known nanogram (ng) amount of HCV replicon total RNA. This was established by plotting the Cycle Threshold values (Ct) from the Neo probe and primer set versus the log (ng) for each HCV replicon total RNA standard. The amount of HCV RNA for each replicon sample was calculated by taking the sample's Ct value, minus the line intercept, divided by the slope of the line. Similarly, the amount of Cyclophilin mRNA per cell was also quantified using a linear regression curve for a known nanogram (ng) amount of HCV replicon total RNA. Again, this was established by plotting the Cycle Threshold values (Ct) from the Cyclophilin probe and primer set versus the log (ng) for each HCV replicon total RNA standard.

In an alternate assay ("Replicon Assay B"), 1000 cells were seeded per well in a 384-well collagen coated black plate from Greiner bio-one (Cat #781946) in 5% FBS. Inhibitors of this invention were added at 24 h post-seeding, and the plates were incubated for 3 days. Cells were subsequently lysed with Qiagen lysis buffer (Cat #1062731) to extract the RNA. HCV replicon RNA level was measured by real-time PCR using the RNA-to-CT kit from Applied Biosystem (Cat #4392656) and genotype-specific primers and probes. The amplicon was located within NS5B. The sequence of the PCR primers are as follows: 5B.2F, ATG-GACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCT-GCGG (SEQ. ID NO. 3). To detect genotype 1A the primer 1A F, TGCGGAACCGGTGAGTACA and 1A R, GCGGGTTTATCCAAGAAAGGA were used; the probe sequence was FAM-CGGAATTGCCAGGACGACCGG.

The real-time RT-PCR reactions were run on ABI PRISM 7900HT or Viia7 Sequence Detection System using the following program: 48° C. for 30 minutes, 95° C. for 10 minutes, 40 cycles of 95° C. for 15 sec, 60° C. for 1 minutes. The 50% effective concentration ($EC_{50}$) was the drug concentration necessary to achieve an increase in the cycle threshold ($C_T$) of 1 over the projected baseline $C_T$. The $EC_{90}$ was the drug concentration necessary to achieve an increase in $C_T$ of 3.2 over the projected baseline $C_T$.

Data was obtained for various compounds of the present invention using the methods described in the Example above, and is presented in the table immediately below. $EC_{50}$ data for replicons 1A, 1AY93H and 2B were obtained using Replicon Assay A and $EC_{50}$ data for replicon 1B was obtained using Replicon Assay B.

| CPD | 1A | 1B | 2a | 2B | 1A Y93H |
|---|---|---|---|---|---|
| Racemate of 1 and 2 | 0.0061 | | | 0.260 | 0.716 |
| 1 | 0.0059 | | | 0.468 | 4.130 |
| 2 | 0.0033 | 0.0025 | 0.0019 | 0.096 | 0.136 |
| 3 | 0.0012 | | | 4.549 | 11.970 |
| 4 | 0.0021 | | | 1.597 | 0.352 |
| 5 | 0.0024 | | | 1.273 | 0.130 |
| 6 | 0.0020 | | | 2.375 | 2.014 |
| 7 | 0.0017 | | | 1.594 | 2.177 |
| 8 | 0.0021 | 0.0011 | | 0.041 | 0.038 |
| 9 | 0.0026 | | | 0.772 | 0.949 |
| 10 | 0.0024 | 0.0012 | | 0.041 | 0.039 |
| 11 | 0.0025 | | | 1.391 | 5.702 |
| 12 | 0.0016 | | | 1.900 | 6.732 |
| 13 | 0.0023 | 0.0032 | | 0.144 | 0.106 |
| 14 | 0.0018 | 0.0026 | | 0.163 | 0.119 |
| 15 | 0.0012 | | | 1.313 | 2.150 |
| 16 | 0.0020 | 0.0008 | | 0.038 | 0.031 |
| 17 | 0.0006 | | | 5.212 | 11.840 |
| 18 | 0.0022 | | | 0.252 | 0.052 |
| 19 | 0.0014 | | | 0.767 | 4.195 |
| 20 | 0.0013 | 0.0014 | | 0.040 | 0.067 |
| 21 | 0.0015 | | | 3.559 | 7.110 |
| 22 | 0.0027 | | | 0.930 | 0.162 |
| 23 | 0.0020 | | | 5.165 | 2.622 |
| 24 | 0.0016 | | | 1.773 | 0.282 |
| 25 | 0.0037 | | | 3.828 | 4.666 |
| 26 | 0.0028 | | | 1.408 | 0.344 |
| 27 | 0.0014 | | | 1.481 | 1.085 |
| 28 | 0.0017 | 0.0021 | | 0.105 | 0.032 |
| 29 | 0.0012 | | | 2.905 | 1.846 |
| 30 | 0.0020 | 0.0026 | 0.0002 | 0.093 | 0.017 |
| 31 | 0.0015 | 0.0022 | | 0.098 | 0.322 |
| 32 | 0.0026 | 0.0026 | | 0.003 | 0.010 |
| 33 | 0.0018 | 0.0021 | | 0.114 | 0.598 |
| 34 | 0.0021 | 0.0030 | | 0.005 | 0.008 |
| 35 | 0.0034 | 0.0012 | | 0.258 | 0.061 |
| 36 | 0.0021 | | | 0.416 | 0.426 |
| 37 | 0.1872 | | | | 15.180 |
| 38 | 0.0052 | | | | 6.649 |
| 39 | 0.0017 | 0.0014 | | 0.910 | 3.384 |
| 40 | 0.0021 | 0.0022 | | 0.086 | 0.107 |
| 41 | | | | 4.134 | |
| 42 | | | | | |
| 43 | 0.0022 | 0.0023 | | 0.081 | 0.075 |
| 44 | | | | 4.908 | |
| 45 | 0.0010 | | | 5.281 | 0.120 |
| 46 | 0.0026 | | | 7.708 | 4.127 |
| 47 | 0.0008 | | | 4.317 | 4.519 |
| 48 | 0.0019 | 0.0015 | | 0.382 | 0.033 |
| 49 | 0.0016 | | | 0.817 | 2.439 |
| 50 | 0.0014 | 0.0014 | | 0.036 | 0.060 |
| 51 | 0.0019 | 0.0025 | | 4.772 | 2.127 |
| 52 | 0.0022 | 0.0031 | | 1.671 | 0.454 |
| 53 | | | | 0.379 | |
| 54 | 0.0049 | 0.0024 | | 0.011 | 0.008 |
| 55 | 0.0019 | | | 1.257 | 1.864 |
| 56 | 0.0024 | | | 0.288 | 0.114 |
| 57 | 0.0020 | | | 0.330 | 0.685 |
| 58 | 0.0022 | | | 0.403 | 1.091 |
| 59 | 0.0032 | 0.0027 | | 0.017 | 0.015 |
| 60 | 0.0030 | 0.0031 | | 0.025 | 0.020 |
| 61 | 0.0023 | | | 0.215 | 1.486 |
| 62 | 0.0019 | | | 0.253 | 0.516 |
| 63 | 0.0026 | 0.0020 | | 0.016 | 0.032 |
| 64 | 0.0027 | 0.0040 | | 0.026 | 0.060 |
| 65 | 0.0029 | 0.0018 | | 0.935 | 0.043 |
| 66 | 0.0034 | | | 2.345 | 0.172 |
| 67 | 0.0012 | | | 0.607 | 0.391 |
| 68 | 0.0018 | 0.0023 | | 0.016 | 0.005 |
| 69 | 0.0032 | 0.0035 | | 0.008 | 0.005 |
| 70 | 0.0028 | 0.0027 | 0.0008 | 0.012 | 0.006 |
| 71 | | | | 5.133 | |
| 72 | | | | 3.297 | |
| 73 | 0.0031 | | | 0.791 | 1.359 |
| 74 | 0.0025 | | | 0.234 | 0.091 |
| 75 | 0.0018 | | | 0.296 | 1.274 |
| 76 | 0.0025 | 0.0032 | | 0.004 | 0.012 |
| 77 | 0.0015 | | | 0.099 | 0.496 |
| 78 | 0.0022 | 0.0026 | | 0.004 | 0.009 |
| 79 | 0.0017 | 0.0027 | | 0.007 | 0.006 |
| 80 | 0.0026 | 0.0032 | | 0.006 | 0.024 |
| 81 | 0.0020 | | | 0.270 | 0.188 |
| 82 | 0.0017 | 0.0021 | | 0.004 | 0.003 |
| 83 | 0.0039 | | | 0.160 | 0.594 |
| 84 | 0.0020 | | | 0.193 | 0.674 |
| 85 | 0.0027 | | | 0.070 | 0.575 |
| 86 | 0.0030 | 0.0027 | | 0.007 | 0.028 |
| 87 | 0.0023 | 0.0034 | | 0.133 | 0.528 |
| 88 | 0.0149 | 0.0026 | | 3.114 | 9.934 |
| 89 | 0.0021 | 0.0031 | | 0.015 | 0.017 |
| 90 | 0.0017 | 0.0032 | | 0.157 | 0.047 |
| 91 | 0.0011 | | | 0.123 | 0.893 |
| 92 | 0.0015 | 0.0024 | | 0.006 | 0.006 |
| 93 | 0.0017 | 0.0021 | | 0.112 | 0.671 |
| 94 | 0.0023 | 0.0033 | | 0.004 | 0.006 |

NOTE:
Blank entries denote that data was not available.

Uses of the Chromane-Substituted Tetracyclic Compounds

The Chromane-Substituted Tetracyclic Compounds are useful in human and veterinary medicine for treating or preventing a viral infection in a patient. In one embodiment, the Chromane-Substituted Tetracyclic Compounds can be inhibitors of viral replication. In another embodiment, the Chromane-Substituted Tetracyclic Compounds can be inhibitors of HCV replication. Accordingly, the Chromane-Substituted Tetracyclic Compounds are useful for treating viral infections, such as HCV. In accordance with the invention, the Chromane-Substituted Tetracyclic Compounds can be administered to a patient in need of treatment or prevention of a viral infection.

Accordingly, in one embodiment, the invention provides methods for treating a viral infection in a patient comprising administering to the patient an effective amount of at least one Chromane-Substituted Tetracyclic Compound or a pharmaceutically acceptable salt thereof.

Treatment or Prevention of a Flaviviridae Virus

The Chromane-Substituted Tetracyclic Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Chromane-Substituted Tetracyclic Compounds are useful in the inhibition of HCV replication, the treatment of HCV infection and/or reduction of the likelihood or severity of symptoms of HCV infection and the inhibition of HCV viral replication and/or HCV viral production in a cell-based system. For example, the Chromane-Substituted Tetracyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Chromane-Substituted Tetracyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Chromane-Substituted Tetracyclic Compounds are also useful in the preparation and execution of screening assays for antiviral compounds. For example the Chromane-Substituted Tetracyclic Compounds are useful for identifying resistant HCV replicon cell lines harboring mutations within NS5A, which are excellent screening tools for more powerful antiviral compounds. Furthermore, the Chromane-Substituted Tetracyclic Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Chromane-Substituted Tetracyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Chromane-Substituted Tetracyclic Compound, or a pharmaceutically acceptable salt thereof, and (ii) at least one additional therapeutic agent that is other than a Chromane-Substituted Tetracyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Chromane-Substituted Tetracyclic Compound and an additional therapeutic agent may be present in fixed amounts (dosage amounts) in a single dosage unit (e.g., a capsule, a tablet and the like).

In one embodiment, the at least one Chromane-Substituted Tetracyclic Compound is administered during a time when the additional therapeutic agent(s) exert their prophylactic or therapeutic effect, or vice versa.

In another embodiment, the at least one Chromane-Substituted Tetracyclic Compound and the additional therapeutic agent(s) are administered in doses commonly employed when such agents are used as monotherapy for treating a viral infection.

In another embodiment, the at least one Chromane-Substituted Tetracyclic Compound and the additional therapeutic agent(s) are administered in doses lower than the doses commonly employed when such agents are used as monotherapy for treating a viral infection.

In still another embodiment, the at least one Chromane-Substituted Tetracyclic Compound and the additional therapeutic agent(s) act synergistically and are administered in doses lower than the doses commonly employed when such agents are used as monotherapy for treating a viral infection.

In one embodiment, the at least one Chromane-Substituted Tetracyclic Compound and the additional therapeutic agent(s) are present in the same composition. In one embodiment, this composition is suitable for oral administration.

In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Chromane-Substituted Tetracyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Chromane-Substituted Tetracyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor. In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), GS-7977 (sofosbuvir, Gilead), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716 (ViroChem), GSK-71185 (Glaxo SmithKline), ANA598 (Anadys), GSK-625433 (Glaxo SmithKline) and XTL-2125 (XTL Biopharmaceuticals), and pharmaceutically acceptable salts thereof, and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004), and pharmaceutically acceptable salts thereof.

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125, and pharmaceutically acceptable salts thereof.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus) and IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix), and pharmaceutically acceptable salts thereof.

Further examples of HCV protease inhibitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10): 7461-7469 (1997); Martin et al., *Protein Eng*, 10(5): 607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, grazoprevir (Merck), which has the following structure:

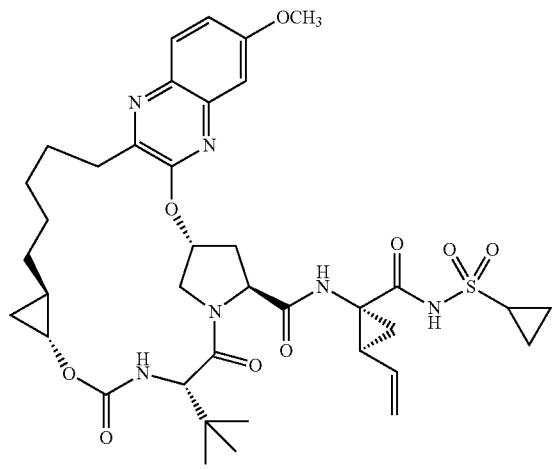 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1]

and the following compounds:

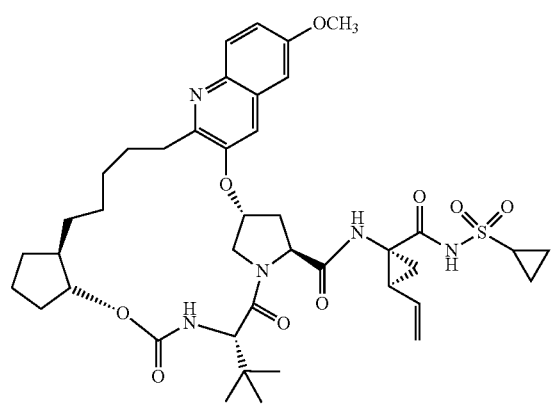

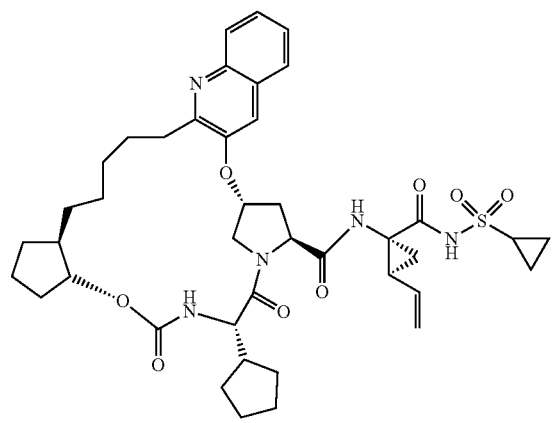

107
-continued
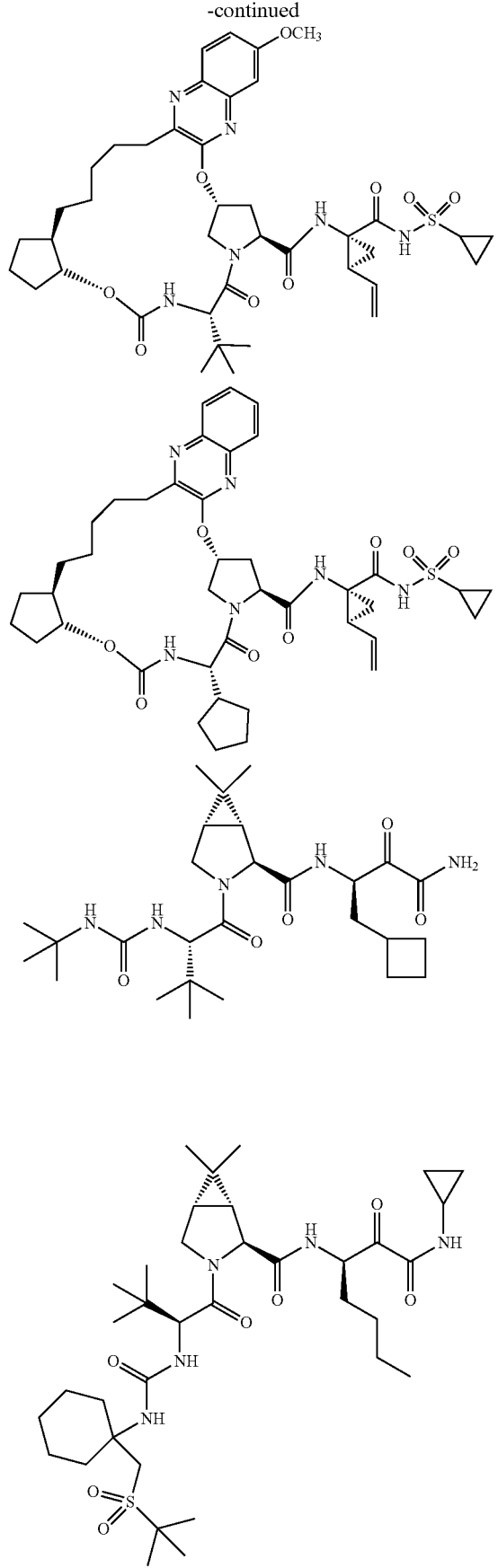
108
-continued
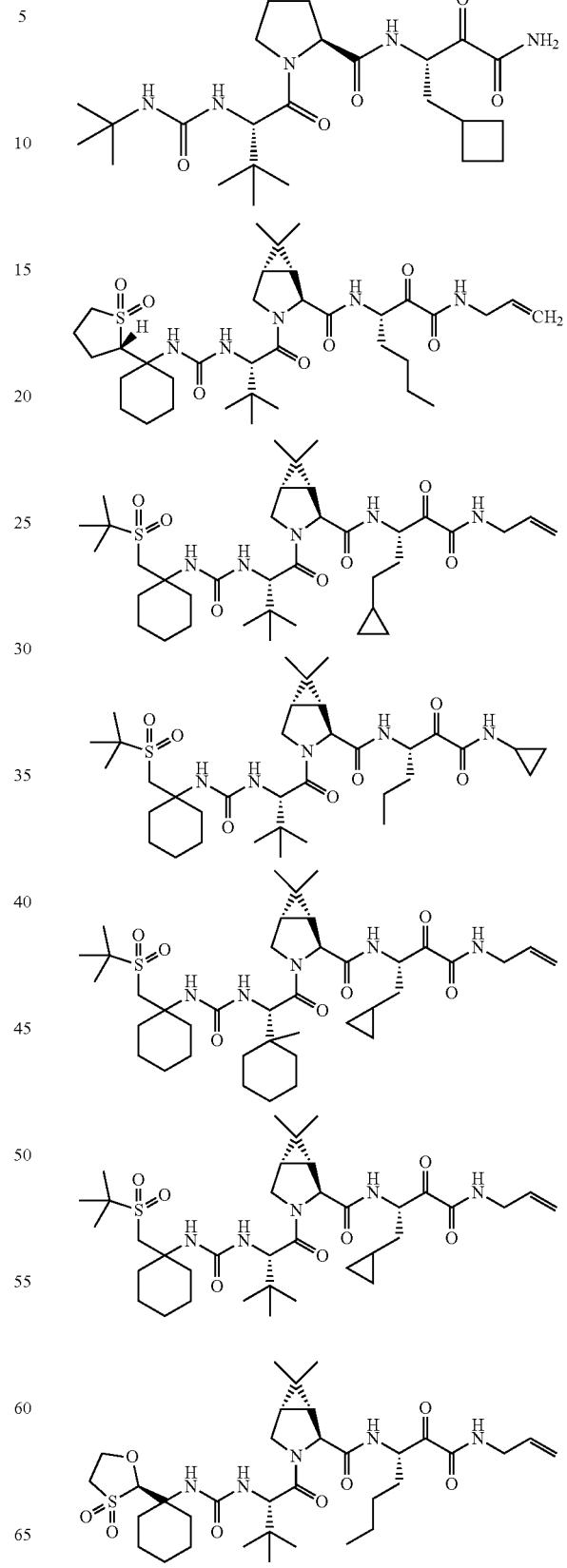

109
-continued
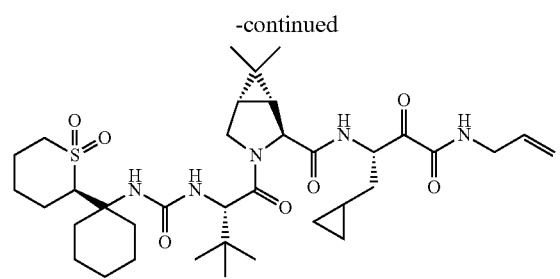
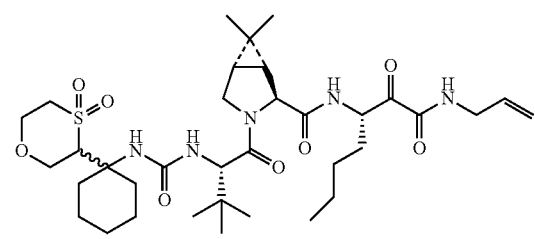
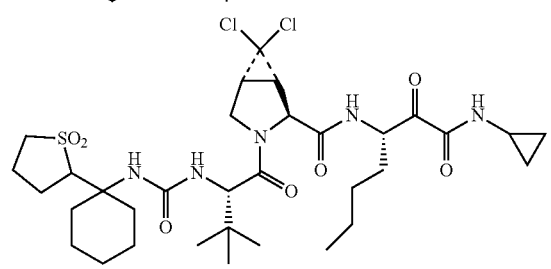
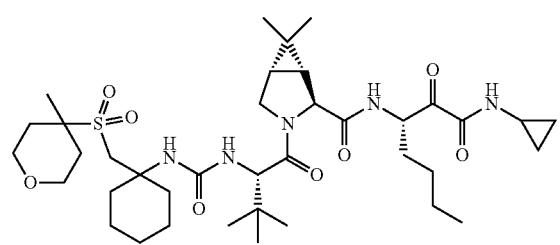
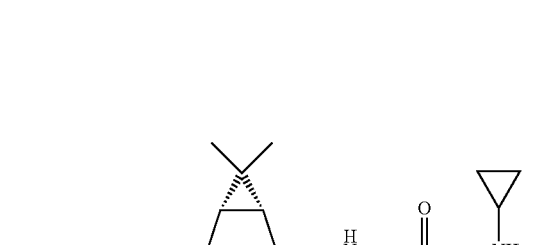
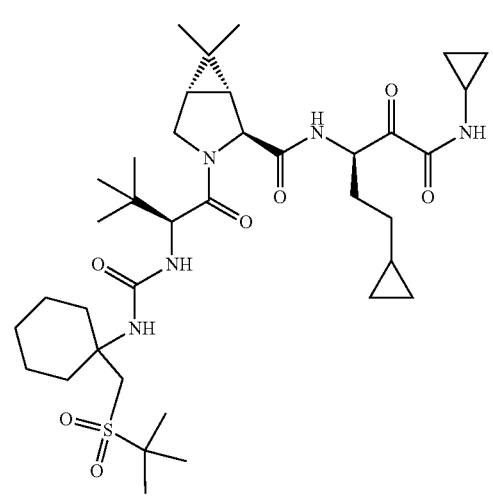
110
-continued
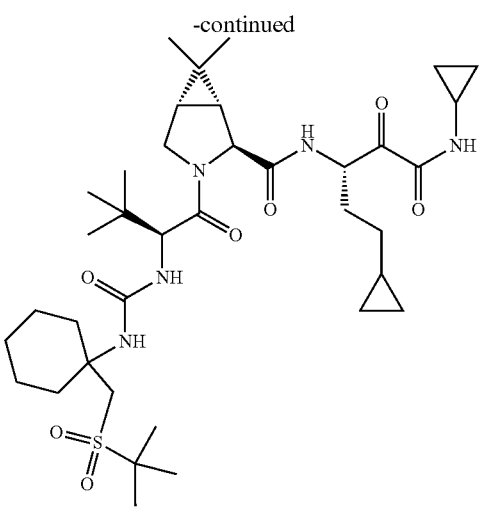
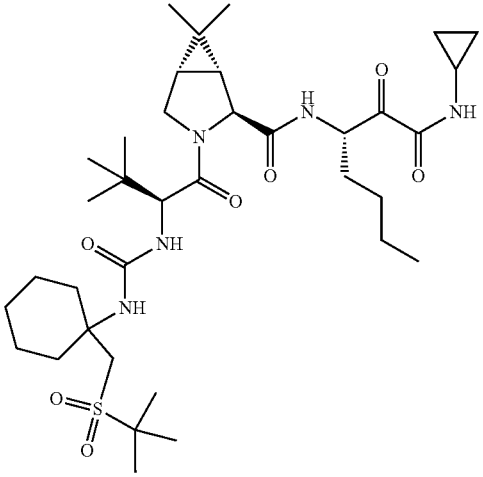
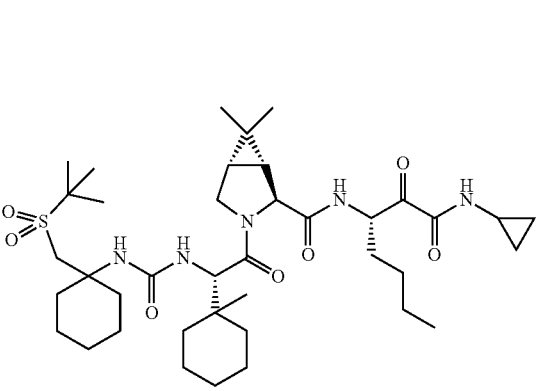
and

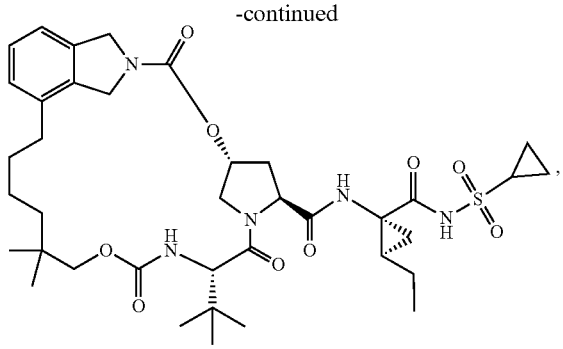

and pharmaceutically acceptable salts thereof.

HCV viral replication inhibitors useful in the present compositions and methods include, but are not limited to, HCV replicase inhibitors, IRES inhibitors, NS4A inhibitors, NS3 helicase inhibitors, NS3 protease inhibitors, NS5A inhibitors, NS5B inhibitors, ribavirin, AZD-2836 (Astra Zeneca), BMS-790052 (Bristol-Myers Squibb, see Gao et al., Nature, 465:96-100 (2010)), viramidine and A-831 (Arrow Therapeutics), an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., N.C.); Alinia (Romark Laboratories), INFORM-1 (a combination of R7128 and ITMN-191); and mycophenolate mofetil (Hoffman-LaRoche, Nutley, N.J.), and pharmaceutically acceptable salts thereof.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Chromane-Substituted Tetracyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside and ribavirin. The combination therapies can include any combination of these additional therapeutic agents.

In another embodiment, one or more compounds of the present invention are administered with one additional therapeutic agent selected from an HCV protease inhibitor and ribavirin.

In still another embodiment, one or more compounds of the present invention are administered with two additional therapeutic agents selected from an HCV protease inhibitor, an HCV replication inhibitor, a nucleoside and ribavirin.

In another embodiment, one or more compounds of the present invention are administered with an HCV protease inhibitor and ribavirin. In another specific embodiment, one or more compounds of the present invention are administered with ribavirin.

In another embodiment, one or more compounds of the present invention are administered with three additional therapeutic agents selected from an HCV protease inhibitor, an HCV replication inhibitor, a nucleoside, a pegylated interferon and ribavirin.

In one embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and ribavirin.

In one embodiment, one or more compounds of the present invention are administered with one additional therapeutic agent selected from an HCV polymerase inhibitor, a viral protease inhibitor, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, and a viral replication inhibitor.

In another embodiment, one or more compounds of the present invention are administered with ribavirin and another therapeutic agent.

In another embodiment, one or more compounds of the present invention are administered with ribavirin and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin and a viral protease inhibitor.

In another embodiment, one or more compounds of the present invention are administered with ribavirin and an HCV protease inhibitor.

In another embodiment, one or more compounds of the present invention are administered with ribavirin and either boceprevir or telaprevir.

In a further embodiment, one or more compounds of the present invention are administered with ribavirin and an HCV polymerase inhibitor.

In another embodiment, one or more compounds of the present invention are administered with ribavirin.

In one embodiment, one or more compounds of the present invention are administered with grazoprevir.

In one embodiment, one or more compounds of the present invention are administered with sofosbuvir.

Compositions and Administration

Due to their activity, the Chromane-Substituted Tetracyclic Compounds are useful in veterinary and human medicine. As described above, the Chromane-Substituted Tetracyclic Compounds are useful for treating or preventing HCV infection in a patient in need thereof.

When administered to a patient, the Chromane-Substituted Tetracyclic Compounds can be administered as a component of a composition that comprises a pharmaceutically acceptable carrier or vehicle. The present invention provides pharmaceutical compositions comprising an effective amount of at least one Chromane-Substituted Tetracyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Chromane-Substituted Tetracyclic Compounds are administered orally.

In another embodiment, the one or more Chromane-Substituted Tetracyclic Compounds are administered intravenously.

In still another embodiment, the one or more Chromane-Substituted Tetracyclic Compounds are administered sublingually.

In one embodiment, a pharmaceutical preparation comprising a Chromane-Substituted Tetracyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Chromane-Substituted Tetracyclic Compound(s) by weight or volume. In various embodiments, the present compositions can contain, in one embodiment, from about 1% to about 70% or from about 5% to about 60% of the Chromane-Substituted Tetracyclic Compound(s) by weight or volume.

The amount and frequency of administration of the Chromane-Substituted Tetracyclic Compounds will be regulated according to the judgment of the attending clinician considering such factors as age, condition and size of the patient as well as severity of the symptoms being treated. Generally, a total daily dosage of the at least one Chromane-Substituted Tetracyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Chromane-Substituted Tetracyclic Compound or a pharmaceutically acceptable salt thereof; (ii) one or more additional therapeutic agents that are not a Chromane-Substituted Tetracyclic Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and two additional therapeutic agents, each of which are independently selected from the group consisting of HCV antiviral agents, immunomodulators, and anti-infective agents.

Kits

In one aspect, the present invention provides a kit comprising a therapeutically effective amount of at least one Chromane-Substituted Tetracyclic Compound, or a pharmaceutically acceptable salt, solvate, ester or prodrug of said compound and a pharmaceutically acceptable carrier, vehicle or diluent.

In another aspect the present invention provides a kit comprising an amount of at least one Chromane-Substituted Tetracyclic Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Chromane-Substituted Tetracyclic Compounds and the one or more additional therapeutic agents are provided in the same container. In one embodiment, the one or more Chromane-Substituted Tetracyclic Compounds and the one or more additional therapeutic agents are provided in separate containers.

What is claimed is:

1. A compound having the formula (I):

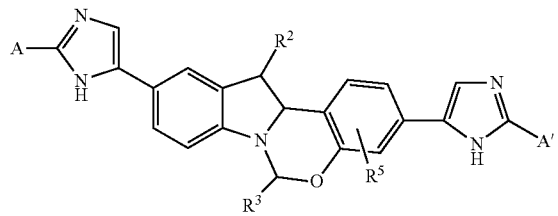

or a pharmaceutically acceptable salt thereof, wherein:

A is:

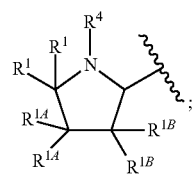

A' is:

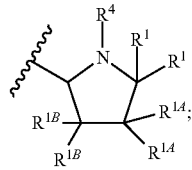

each occurrence of $R^1$ is H;

each occurrence of $R^{1A}$ is independently selected from H and halo, or one $R^{1A}$ group and an $R^1$ group that are attached to same ring, together with the ring carbon atoms to which they are attached, can combine to form a fused $C_3$-$C_7$ cycloalkyl group;

each occurrence of $R^{1B}$ is independently selected from H—;

$R^2$ is selected from H and halo;

$R^3$ is selected from:

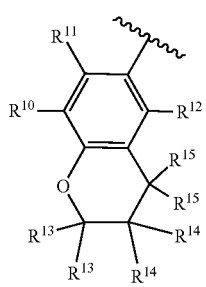 and 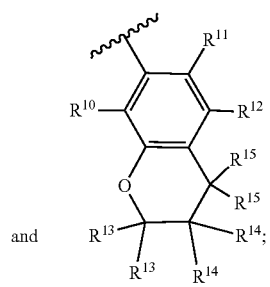

each occurrence of $R^4$ is independently selected from
—C(O)—C($R^7$)$_2$NHC(O)O—$R^8$;

$R^5$ represents up to 3 optional substituents, each independently selected from halo;

each occurrence of $R^7$ is independently selected from H, $C_1$-$C_6$ alkyl, $C_1$-$C_6$ haloalkyl, phenyl, and 4 to 8-membered monocyclic heterocycloalkyl, wherein said 4 to 8-membered monocyclic heterocycloalkyl group, can be optionally substituted with up to 5 groups, each independently selected from $C_1$-$C_6$ alkyl;

each occurrence of $R^8$ is independently selected from $C_1$-$C_6$ alkyl;

$R^{10}$ is H;
$R^{11}$ is H;
$R^{12}$ is H;

each occurrence of $R^{13}$ is independently selected from H, and $C_1$-$C_6$ alkyl, or both $R^{13}$ groups and the common carbon atom to which they are each attached, can combine to form a spirocyclic $C_3$-$C_7$ cycloalkyl group;

each occurrence of $R^{14}$ is independently selected from H, $C_1$-$C_6$ alkyl, and halo; or both $R^{14}$ groups and the common carbon atom to which they are each attached, join to form a spirocyclic $C_3$-$C_7$ cycloalkyl group; or an $R^{14}$ group and $R^{13}$ group, together with the carbon atoms to which they are each attached, join to form a fused $C_3$-$C_7$ cycloalkyl group; or an $R^{14}$ group and $R^{15}$ group, together with the carbon atoms to which they are each attached, can combine to form a fused $C_3$-$C_7$ cycloalkyl group; and each occurrence of $R^{15}$ is independently selected from H, $C_1$-$C_6$ alkyl, and halo, or both $R^{15}$ groups and the common carbon atom to which they are each attached, can combine to form a spirocyclic $C_3$-$C_7$ cycloalkyl group.

2. The compound of claim 1, wherein each occurrence of $R^4$ is independently —C(O)CH($R^7$)NHC(O)OCH$_3$, or a pharmaceutically acceptable salt thereof.

3. The compound of claim 1 having the formula:

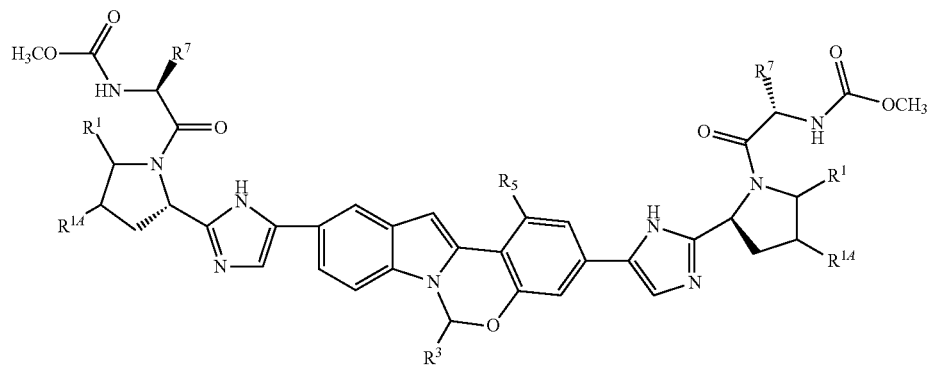

(Ia)

or a pharmaceutically acceptable salt thereof, wherein:

each $R^1$ is H;

each $R^{14}$ is independently H or F, or an $R^{14}$ group and an $R^1$ group that are attached to same ring, together with the ring carbon atoms to which they are attached, can combine to form a fused cyclopropyl group;

$R^3$ is selected from:

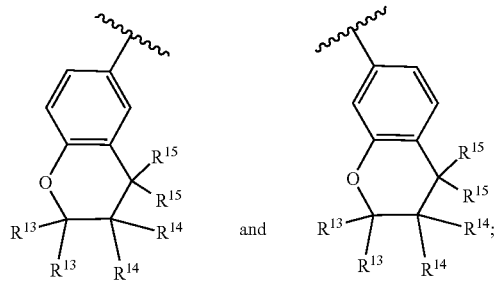

$R^5$ is H, F or methyl;

each occurrence of $R^7$ is independently selected from $C_1$-$C_6$ alkyl, $C_1$-$C_6$ haloalkyl, phenyl and 4 to 6-membered monocyclic heterocycloalkyl, wherein said 4 to 6-membered monocyclic heterocycloalkyl group can be optionally substituted with up to 2 groups, each independently selected from $C_1$-$C_6$ alkyl;

each occurrence of $R^{13}$ is independently selected from H and $C_1$-$C_6$ alkyl, or both $R^{13}$ groups and the common carbon atom to which they are each attached, join to form a spirocyclic $C_3$-$C_7$ cycloalkyl group;

each occurrence of $R^{14}$ is independently selected from H, halo and $C_1$-$C_6$ alkyl; or both $R^{14}$ groups and the common carbon atom to which they are each attached, join to form a spirocyclic $C_3$-$C_7$ cycloalkyl group; or an $R^{14}$ group and $R^{13}$ group, together with the carbon atoms to which they are each attached, join to form a fused $C_3$-$C_7$ cycloalkyl group; or an $R^{14}$ group and $R^{15}$ group, together with the carbon atoms to which they are each attached, join to form a fused $C_3$-$C_7$ cycloalkyl group; and each occurrence of $R^{15}$ is independently selected from H, $C_1$-$C_6$ alkyl and halo, or both $R^{15}$ groups and the common carbon atom to which they are each attached, join to form a spirocyclic $C_3$-$C_7$ cycloalkyl group.

4. The compound of claim 1, wherein A and A' are each independently selected from:

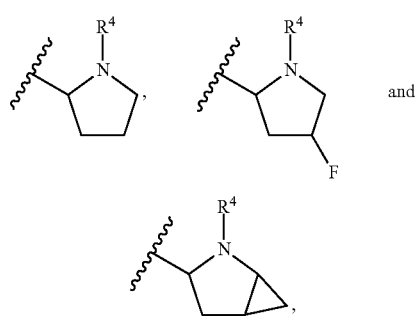
or a pharmaceutically acceptable salt thereof.
5. The compound of claim 1, wherein $R^3$ is selected from:
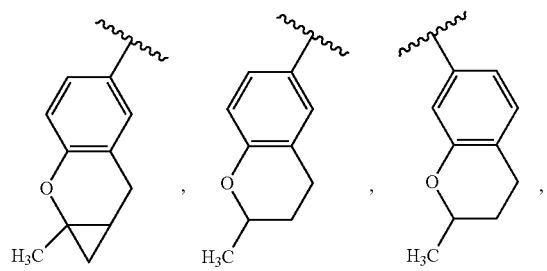
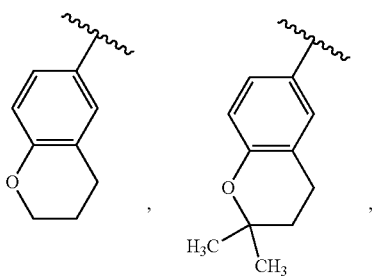
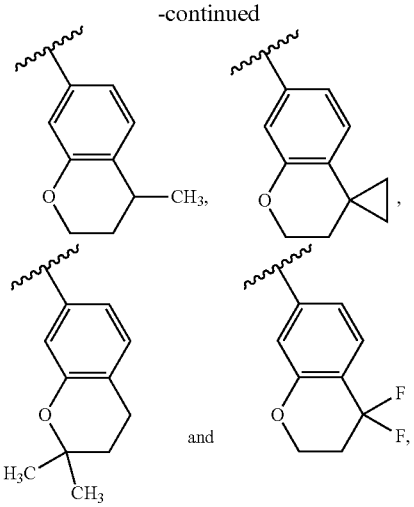
or a pharmaceutically acceptable salt thereof.
6. The compound of claim 1, wherein each occurrence of $R^7$ is independently selected from isopropyl, —CF(CH$_3$)$_2$,
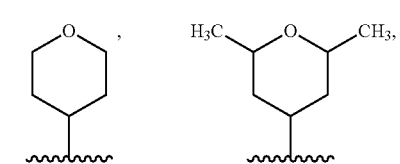
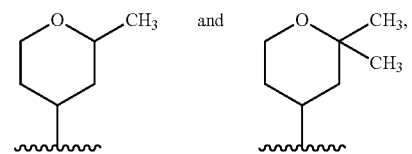
or a pharmaceutically acceptable salt thereof.
7. A compound having the structure:
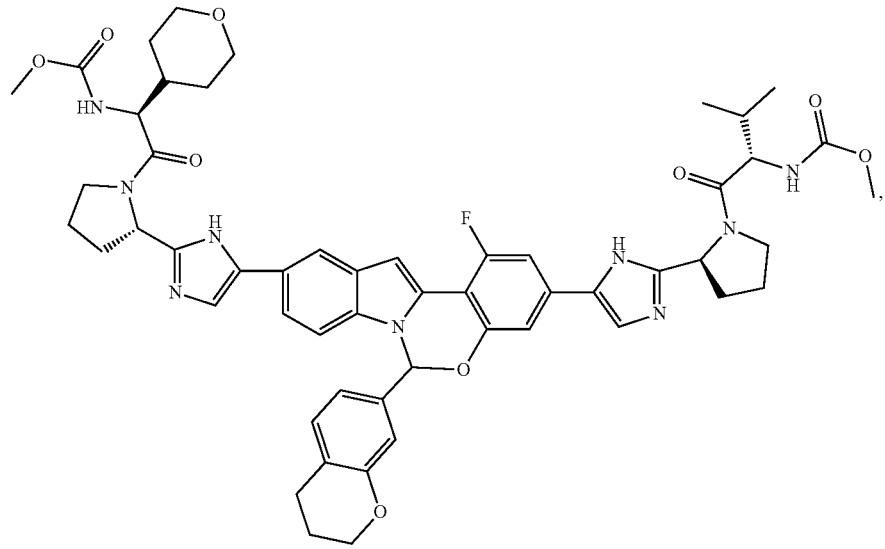

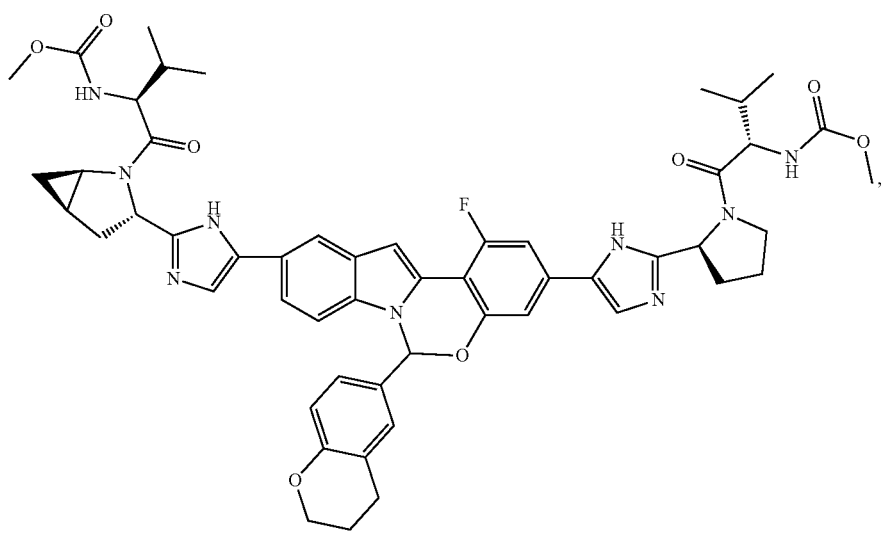
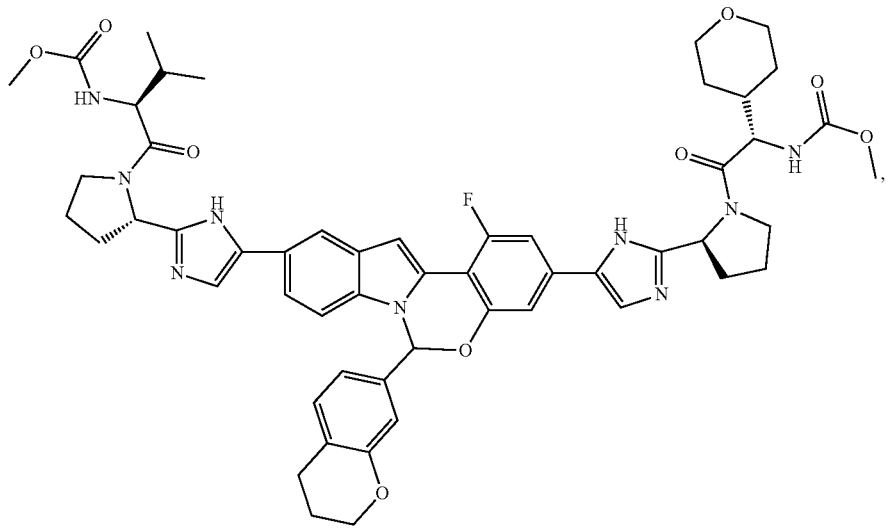
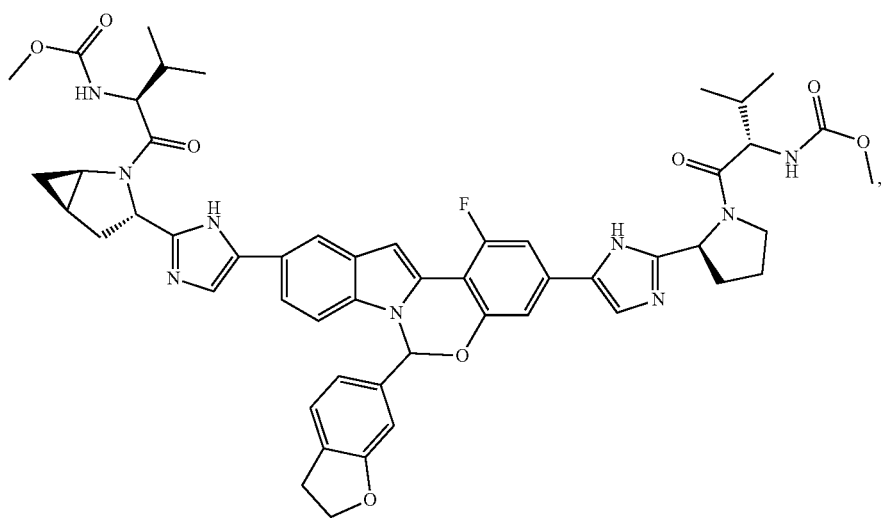

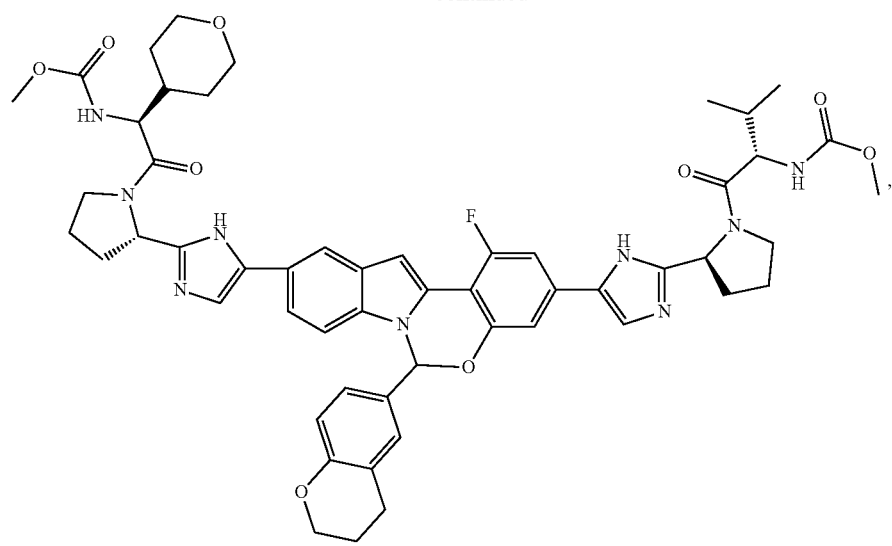
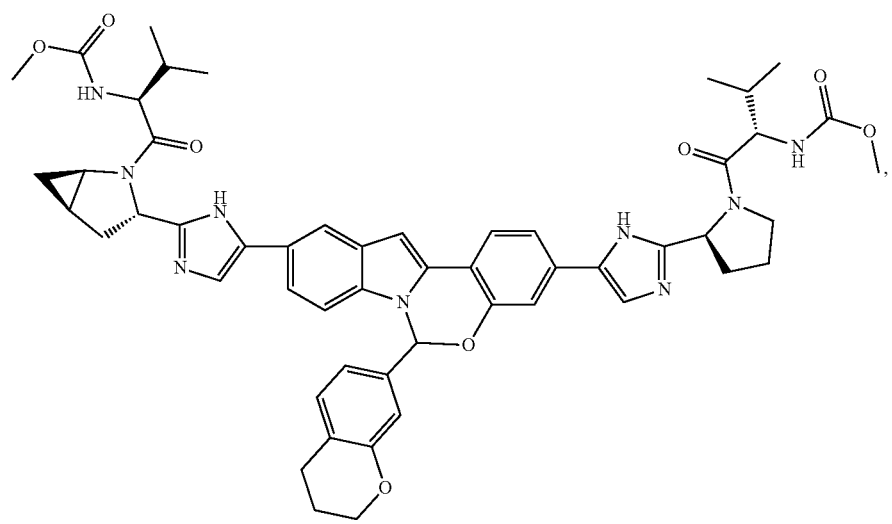
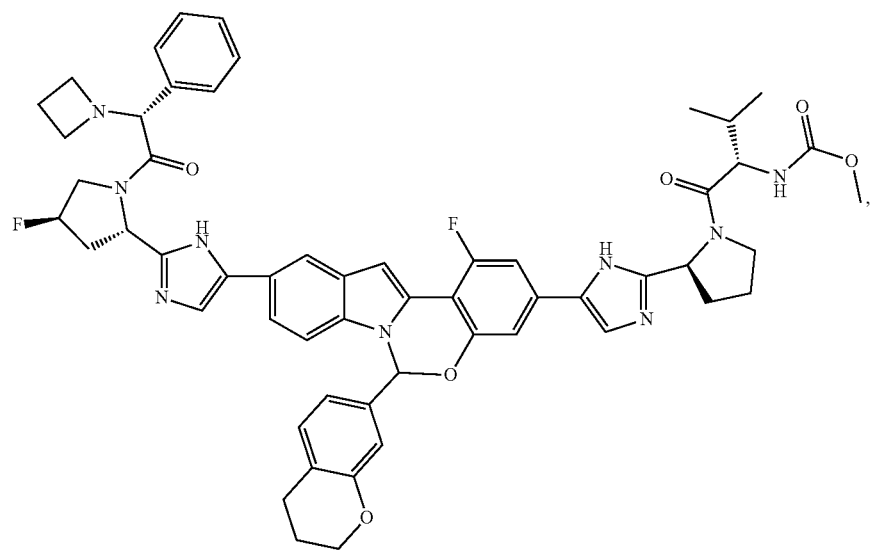

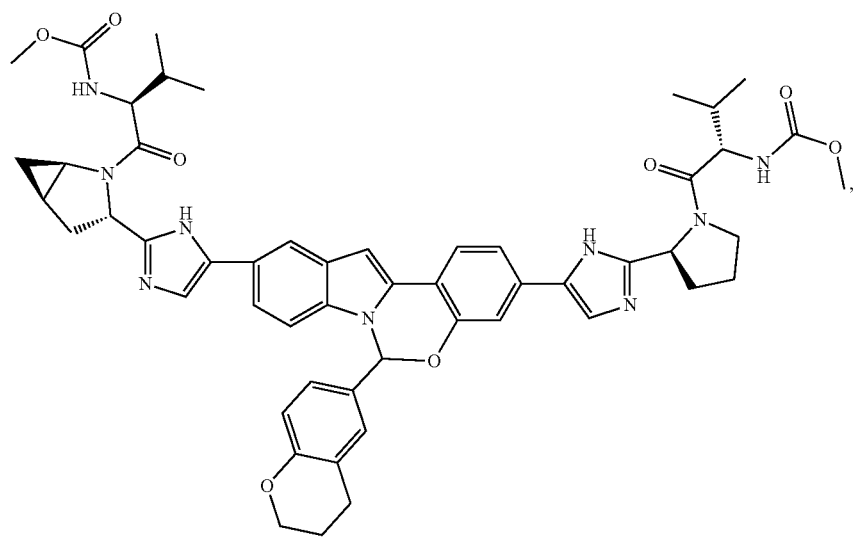
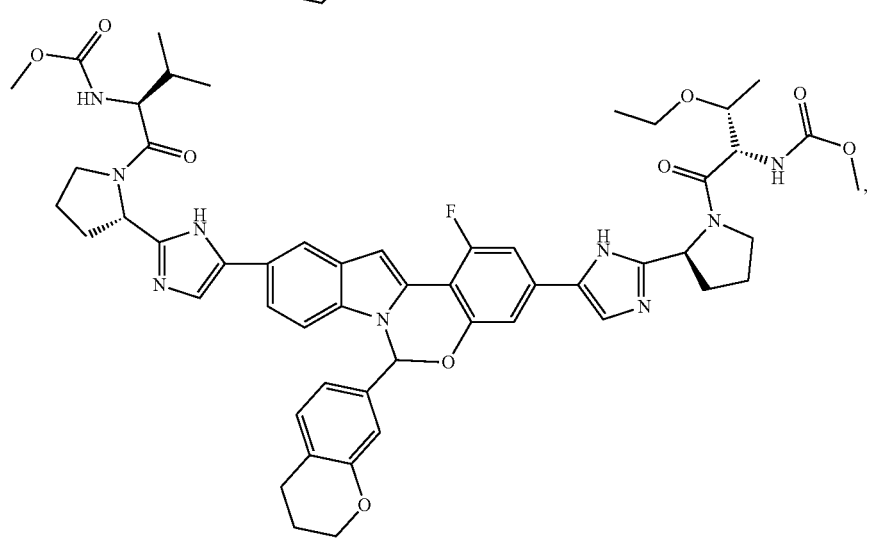
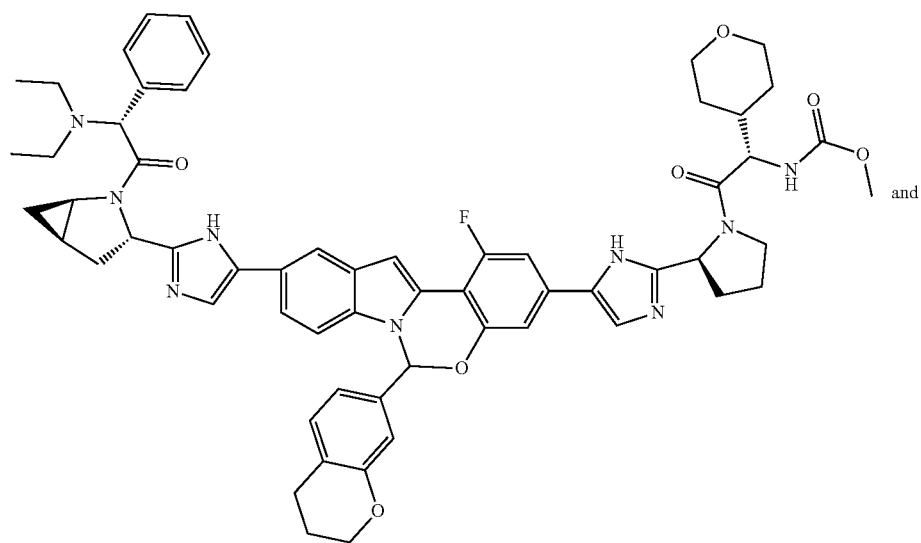

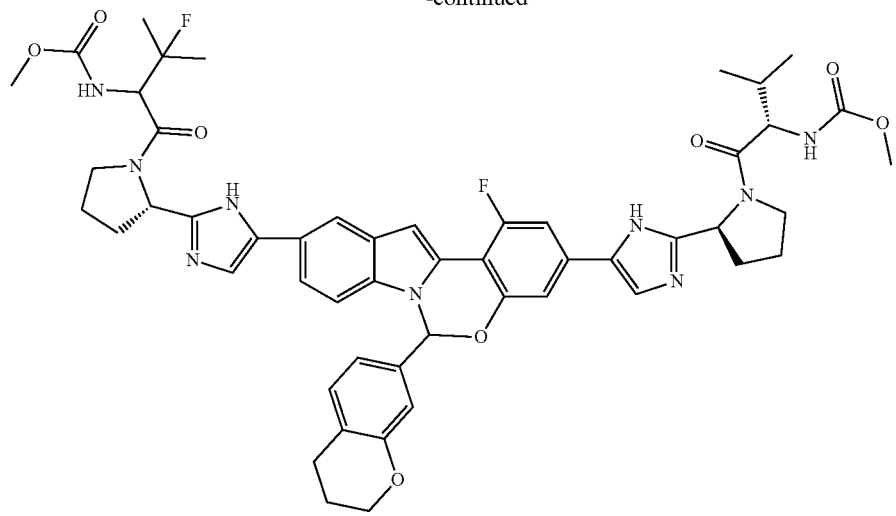

or a pharmaceutically acceptable salt thereof.

8. A pharmaceutical composition comprising an effective amount of the compound of claim 1, or a pharmaceutically acceptable salt thereof, and a pharmaceutically acceptable carrier.

9. The pharmaceutical composition according to claim 8 further comprising a second therapeutic agent selected from the group consisting of HCV antiviral agents, immunomodulators, and anti-infective agents.

10. The pharmaceutical composition according to claim 9, further comprising a third therapeutic agent selected from the group consisting of HCV protease inhibitors, HCV NS5A inhibitors and HCV NS5B polymerase inhibitors.

11. A method of treating a patient infected with HCV comprising the step of administering an amount of the compound according to claim 1, or a pharmaceutically acceptable salt thereof, effective to treat infection by HCV in said patient.

12. The method according to claim 11, further comprising administering a second additional therapeutic agent to said patient, wherein said second additional therapeutic agent is independently selected from HCV protease inhibitors, HCV NS5A inhibitors and HCV NS5B polymerase inhibitors.

13. The method according to claim 12, further comprising administering a third additional therapeutic agent to said patient, wherein said third additional therapeutic agent is independently selected from HCV protease inhibitors, HCV NS5A inhibitors and HCV NS5B polymerase inhibitors.

14. The method according to claim 12, wherein said second additional therapeutic agent is grazoprevir.

* * * * *